United States Patent [19]
Comer et al.

[11] Patent Number: 5,925,568
[45] Date of Patent: Jul. 20, 1999

[54] RELEASE AND MOBILIZATION OF HAEMATOPOIETIC CELLS

[75] Inventors: Michael Berisford Comer; Matthew John McCourt; Lars Michael Wood; Michael George Hunter; Richard Mark Edwards, all of Oxford, United Kingdom

[73] Assignee: British Biotech Pharmaceuticals Limited, Oxford, United Kingdom

[21] Appl. No.: 08/545,587

[22] PCT Filed: Jun. 15, 1994

[86] PCT No.: PCT/GB94/01284

§ 371 Date: Jan. 16, 1996

§ 102(e) Date: Jan. 16, 1996

[87] PCT Pub. No.: WO94/28916

PCT Pub. Date: Dec. 22, 1994

[30] Foreign Application Priority Data

Jun. 15, 1993 [GB] United Kingdom .................... 9312343
Nov. 25, 1993 [GB] United Kingdom .................... 9324252
Feb. 4, 1994 [GB] United Kingdom .................... 9402188

[51] Int. Cl.$^6$ ................................ C12N 5/00; C07K 1/00
[52] U.S. Cl. ............................................ 435/378; 530/350
[58] Field of Search ................... 514/2, 44; 424/93.1, 424/93.2, 93.21; 530/350

[56] References Cited

FOREIGN PATENT DOCUMENTS

WO 8910133  11/1989  WIPO.
WO 9104274   4/1991  WIPO.

OTHER PUBLICATIONS

Pragnell et al. From clone to clinic—a stem cell inhibitory cytokine with clinical potential. Leukemia, vol. 7, No. 5, pp. 777–778, May 1993.

Dunlop et al. Demonstration of stem cell inhibition and myeloprotective effects of SCI/rhMIP1–alpha in vivo. Blood, vol. 79, No. 9, pp. 2221–2225, May 1, 1992.

Lord et al. MIP–1–alpha protects CFU–S from the cytotoxic effects of hydroxyurea in vivo. 18th Meeting of the European study group for Cell proliferation, May 6–9, 1992. Cell Proliferation, vol. 25, No. 5, p. 503, May 1992.

Zwierzina, H. Practical aspects of cytokine therapy. Stem Cells, vol. 11, No. 3, pp. 143–153, May 1993.

*Primary Examiner*—Brian R. Stanton
*Assistant Examiner*—Deborah J. R. Clark
*Attorney, Agent, or Firm*—Hale and Dorr LLP

[57] ABSTRACT

Stem cell inhibitors such as murine and human macrophage inflammatory protein-1alpha (muMIP-1alpha and huMIP-1alpha/LD78) and their analogues and variants enhance the release and mobilization of haematopoietic cells. This property makes them useful in enhancing responses against infection and in cell harvesting.

10 Claims, 38 Drawing Sheets

SEQUENCE LISTING

```
(1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 222 base pairs
        (B) TYPE: nucleic acid
        (C) STRANDEDNESS: double
        (D) TOPOLOGY: linear (ii) MOLECULE TYPE: DNA (genomic)

(iii) ANTI-SENSE: NO (ix) FEATURE:
        (A) NAME/KEY: CDS
        (B) LOCATION: 1..222
        (D) OTHER INFORMATION: /codon_start= 1
            /product= "LD78 SYNTHETIC GENE"

(xi) SEQUENCE DESCRIPTION: SEQ ID NO:1:
```

-continued

```
AGC TTG GAT AAA AGA TCC TTG GCT GCT GAC ACT CCA ACC GCT TGT TGT         48
Ser Leu Asp Lys Arg Ser Leu Ala Ala Asp Thr Pro Thr Ala Cys Cys
 1           5                   10                  15

TTC TCT TAC ACC TCT AGA CAA ATT CCA CAA AAT TTC ATT GCT GAC TAC         96
Phe Ser Tyr Thr Ser Arg Gln Ile Pro Gln Asn Phe Ile Ala Asp Tyr
            20                  25                  30

TTT GAA ACT TCT TCT CAA TGT TCC AAG CCA GGT GTC ATC TTC TTG ACT        144
Phe Glu Thr Ser Ser Gln Cys Ser Lys Pro Gly Val Ile Phe Leu Thr
        35                  40                  45

AAG CGC TCG AGA CAA GTC TGT GCT GAC CCA TCT GAA GAA TGG GTT CAA        192
Lys Arg Ser Arg Gln Val Cys Ala Asp Pro Ser Glu Glu Trp Val Gln
    50                  55                  60

AAA TAT GTT TCT GAC TTG GAA TTG TCT GCC                                222
Lys Tyr Val Ser Asp Leu Glu Leu Ser Ala
 65                     70
```

(2) INFORMATION FOR SEQ ID NO:2:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Leu Ala Ala Asp Thr Pro Thr Ala Cys Cys Phe Ser Tyr Thr Ser
 1           5                  10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala
65
```

RELEASE AND MOBILIZATION OF HAEMATOPOIETIC CELLS

This invention relates to te use of stem cell inhibitors (SCIs), including wild-type molecules and variants (both naturally occurring and engineered), as agents to promote the release and mobilisation of haematopoietic cells from the marrow. Such agents are useful in enhancing immune responses and in cell harvesting.

The various mature blood cell types are all ultimately derived from a single class of progenitor cell known as haematopoietic stem cells. True stem cells are both pluripotent—that is they can give rise to all cell types—and capable of self-renewal. This is defined by their ability to repopulate am whose haematopoietic system has been destroyed by radiation. Stem cells represent a very small percentage of bone marrow cells, and are normally quiescent. When stimulated to divide, they give rise to more committed, differentiated daughter cells with greater proliferative potential. The term stem cell is often also applied to these so-called "early progenitors" cells. Sequential rounds of division and differentiation give rise to an enormous amplification of cell numbers, necessary for the production of mature blood cells. This process of division and differentiation is subject to regulation at many levels to control cell production. Thus positive factors such as the Colony Stimulating Factors (CSFs) act to promote division of early progenitors and differentiation down particular lineages, for example G-CSF drives neutrophil production whilst erythropoietin promotes formation of erythrocytes. More recently, it has been recognised that negative factors may also play an important role in regulating haematopoiesis.

Leukocytic, haematopoietic cells are important in maintaining the body's defence against disease. For example, macrophages and lymphocytes are involved in potentiating the body's response to infection and tumours; granulocytes (neutrophils, eosinophils and basophils) are involved in overcoming infection, parasites and tumours.

Other cell types derived from haematopoietic stem cells include platelets and erythrocytes. Platelets form an important element in the haemostatic mechanism through initiating thrombus formation by their adhesion to each other and to damaged surfaces, and by the release of factors which assist in the formation of the fibrin clot. Eryrocytes are mainly involved in the transport of oxygen.

Purified populations of cells are increasingly being used therapeutically and it would therefore be advantageous to be able to increase the number of circulating blood cells. It is also useful to be able to harvest haematopoietic cells prior to chemotherapy or radiotherapy, thus protecting them from the effects of this therapy; after therapy, the cells can be returned to the patient. It would therefore be highly beneficial to provide an agent which promoted the release and mobilisation of a number of haematopoietic cells. Such an agent would be useful for enhancing the responses to infection.

A number of cytokines have been implicated in causing chemokinesis of haematopoietic cells; for example IL-8 (a member of the C-X-C family of chemokines) is chemotactic for neutrophils but not for monocytes, whereas LD78 (a member of the C-C family of chemokines) is chemotactic for monocytes but not for neutrophils. Chemokinesis is an in vitro phenomenon, reflecting the ability of cells to move towards a stimulus. It is, however, distinct from the release and mobilisation of cells, which is an in vivo phenomenon in which cells leave one tissue compartment and enter the bloodstream. If there is a relationship between chemokinesis and release/mobilisation, it is unclear what its nature is.

Neutrophils, along with other granulocytes, are an essential component of the body's cellular defences against infection. This is illustrated by the fact that individuals with a leukocyte dysfunction such as LAD (leukocyte adhesion deficiency) are very prone to infection. Neutrophils are continuously produced in large numbers from myeloid precursors in the bone marrow. Neutrophils are released into the circulation from where they can enter the tissues in response to chemotactic signals released locally during infection or tissue damage. This extravasation is critically dependent on adhesive interactions between the vessel wall and the neuerophil, and involves activation of the neutrophil and upregulation of the avidity of its $\beta2$-integrins. The activated neutrophil can then attack the infective agent by release of enzymes and free-radicals, as well as by phagocytosis. Circulating and tissue neutrophils have a short half-life of about 2 hr. This means that a high rate of neutrophil production in the marrow is essential if the ability of the body to defend itself against infection is not to be compromised.

An important consequence of this high turnover rate is that neutrophil numbers drop very rapidly when the bone marrow is damaged. This can occur during some viral infections, but clinically the most important cause is chemotherapy or radiotherapy used to treat malignant disease. Such treatments destroy dividing cells within the tumour, but also devastate other highly proliferative cell populations such as the bone marrow and gut epithelial cells. The bone marrow toxicity kills haematopoietic precursors indiscriminately, but the major impact on nature cell numbers is seen with neutrophils and to a lesser extent platelets because of the short half-life of these cells. The neutropaenia resulting from chemotherapy occurs within two or three days of treatment, and leaves the patient vulnerable to infection for up to 2 weeks until the haematopoietic system has recovered sufficiently for neutrophil counts to recover.

One way to minimise the impact of ts neutropaenia has been to use colony stimulating factors such as G-CSF and GM-CSF to enhance the neutrophil recovery rate by stimulating the division and differentiation of neutrophil precursors. Such an approach can shorten the period of neutropaenia but not abolish it.

An alternative and complementary approach is to use negative regulators of haematopoiesis such as SCIs to protect early progenitors by causing them to go out of cell-cycle during the period of exposure to the cytotoxic agent. Such cells, when held out of cycle, are more resistant to the toxic effects of chemotherapy.

Leukocyte depletion, or leukopaenia, occurs in a number of conditions, and neutropaenia is one important aspect of leukopaenia generally.

Stem cell inhibitor protein, also known as MIP-1α (macrophage inflammatory protein) and huMIP-1α or LD78 (for the human form), is a peptide of about 69 amino acids and is a member of a growing family of molecules with homologous structure—the chemokine or intercrine family. Other notable members of this family include IL-8 and platelet factor 4. MIP-1α is unusual in that it has remarkable self-assembly properties. Under physiological conditions, it can form ordered multimers with molecular weights in excess of 250kDa, a property it shares with the closely related protein MIP-1β.

MIP-1α was originally isolated as a macrophage product with inflammatory properties (Wolpe et a., *J. Exp. Med.*, 167 570–581 (1988)). However, it now seems that at least some of the original suggestions of the functions and properties of the molecule were wrong. For example, it now appears, somewhat surprisingly, that the protein, when produced as a homogeneous product from recombinant sources, is not particularly inflammatory and the highly purified protein is not pyrogenic.

A more important role for MIP-1α emerged when it was discovered that it was the same molecule as a factor purified from bone marrow some years earlier (Graham et at., *Nature* 344 442–444 (1990)). This factor, stem cell inhibitor protein, was defined by its ability to put early haematopoietic progenitor ceils (stem cells) out of cycle. Because stem cells are needed for repopulation of the bone marrow, there is a great deal of interest in the use of this protein as a marrow protective agent during cancer chemotherapy. A number of routes for the production of the wild-type molecule as well as engineered variants with improved physicochemical properties are described in WO-A-9313206.

It has now surprisingly been found that SCIs promote release and mobilisation of haematopoietic cells, and that this occurs extremely rapidly; more particularly, they promote leukophilia (by which is meant an elevated circulating white blood cell count). The discovery arose from the initial observation that administration of SCI in a murine model of chemotherapy-induced neutropaenia induced a rapid and profound rise in the circulating neutrophil count. This acute neutrophilia was too large (8–10 fold increase) to be explained by simple demargination of neutrophils in the circulation. The most likely explanation is that the agent is causing release of newly formed neutrophilia from the bone marrow in addition to simple demargination. The neutrophilia is induced within 5 minutes of administrating the SCI protein, and typically decays to normal levels within about 24 hr. Subsequent readministration of SCI causes a similar effect. The effect is seen following both i.v. and s.c. administration.

The neutrophilic activity is all the more surprising given the discovery that LD78 is neither pyrogenic nor particularly inflammatory. The observed neutrophilic effect of SCIs cannot therefore be easily rationalised by analogy with the neutrophilic activity of pyrogenic and inflammatory molecules such as FMLP (f-Met-Leu-Phe) and IL-8 (interleukin-8).

In addition to its inhibitory effects on stem cells and early progenitor cells, the SCI protein also has stimulatory effects on the division of later, more committed, progenitors. These effects, however, are not currently thought to be as important as the role of SCI in regulating the proliferation of stem cells and other early progenitors.

However, it has not previously been shown that SCI administration promotes the release and mobilisation of haematopoietic stem cells and other early progenitor cells. It has now surprisingly been shown that administration of SCIs gives rise to a rapid and prolonged increase in the circulating CFU-S cell population. The most likely explanation is that the agent is causing release of stem cells and more committed progenitors from the bone marrow.

SCIs therefore promote the release of mature cells such as neutrophils and early progenitor cells such as CFU-S: SCIs have an effect on marrow cells at a wide variety of stages of maturation.

According to a first aspect of the invention there is provided the use of a stem cell inhibitor (SCI) in the preparation of an agent for promoting an elevated circulating haematopoietic cell count, particularly by the release and mobilisation of haematopoietic cells. The invention is thus useful in a method of inducing the release of haematopoietic cells from the marrow of an animal, the method comprising administering to the animal an effective dose of a stem cell inhibitor.

Any form of stem cell inhibitor protein can be used to indue the release of haematopoietic cells. The invention encompasses the use of the various naturally occurring stem cell inhibitors that have been described, including the murine protein (muMIP-1α) and the human protein(s) (huMIP-1α or LD78 SEQ ID NO.2), as well as natural or protein engineered forms which may have improved biophysical or biological properties ("varants" and "analogues"). Wild-type murine or human MIP-1α SEQ ID NO.2 may be prepared as described in WO-A-9104274 or WC-A-9205198. More preferable, however, is the use of a variant of murine or human MIP-1α SEQ ID NO.2 containing one or more amino acid substitution to control the higher order association of the molecule (as described in WO-A-9313206 U.S. Ser. Nos. 07/982,759 (pending) and 08/450, 905 (now allowed), which corresponds to pending U.S. Ser. No. 07/982,759, filed Mar. 8, 1993).

The term "variant" (or its synonym for present purposes "analogue") is used, broadly, in a functional sense. As a practical matter, though, most variants will have a high degree of homology with the prototype molecule if biological activity is to be substantially preserved. It will be realised that the nature of changes from the prototype molecule is more important that the number of them. As guidance, though, at the amino acid level, it may be at (in increasing order of preference) at least 40, 50, 60, 65, 67 or 68 of the residues will be the same as the prototype molecule; at the nucleic acid level, nucleic acid coding for an analogue may for example hybridise under stringent conditions (such as at approximately 35° C. to 65° C. in a salt solution of approximately 0.9 molar) to nucleic acid coding for the prototype molecule, or would do so but for the degeneracy of the genetic code.

Molecules useful in the present invention can be prepared from natural or recombinant sources. The preferred form of the natural molecule is a 69 amino acid form of LD78 described by Obaru et al *J. Bichem.* 99 885–894 (1986). Given the low amounts of SCI present in natural sources, its production by a recombinant route is greatly preferred. In view of the tendency of SCI to multimerise to form large macromolecular complexes, it is also preferred to use an engineered variant of the molecule that does not associate beyond a tetramer. Such variants, and their production, are the subject of WO-A-9313206 which corresponds to pending U.S. Ser. No. 07/982,759, filed Mar. 8, 1993. The variants preferred for use in that application are similarly preferred for use in this application.

There are in principle four stages in the association mechanism at which it is possible to prevent the formation of large multimers (and therefore aggregates) of SCIs. Inhibition of each of these stages could be influenced by a mutation in a different region of the SCI molecule.

First, further association of tetramers can be inhibited. Secondly, if the SCI dimers are prevented from associating to tetramers, then fer multimerisation will be inhibited. Thirdly, SCI monomers may be prevented from dimerising. Fourthly, further association of dodecamers to higher order multimers can be inhibited. Any of these options can be implemented by specific mutation of residues involved in promoting and/or stabilising the association events. A further option would be to use a combination of mutations simultaneously to block two or all of the association events.

The following amino acid residues are preferred for modification:
  (i) amino acid residues which could be involved in stabilising the interaction between two dimers; and
  (ii) amino acid residues at surface regions, on the external faces of the tetramer, which could act as sites for higher order association.

Radical mutation of individual or combinations of key residues stabilising the association of dimers into tetramners will yield a dimeric recombinant SCI variant or analogue molecule. Simliarly, mutation of residues at the sites of association of tetramers to multimers will yield a tetrameric SCI variant or analogue molecule. The amino acid modification preferably involves a substitution, although deletions and additions are contemplated within the scope of the invention.

The types of mutation preferred for producing the desired effects are:

(i) charge repulsions (successfully used to produce monomeric insulin; Dodson, *Prospects in Protein Engineering Meeting Abstracts*, 49–53, (1989));

(ii) hydrophobic to hydrophilic charges;

(iii) neutral/hydrophobic to charged.

It is generaly better not to substitute very hydrophobic residues into the protein in order to avoid contributing to the hydrophobic effect in association. Equally, it is preferred to avoid mutations which significantly disrupt secondary structural elements of the protein: so, for example, known β-breakers are preferably not introduced into β-sheet regions.

Certain types of mutation are most effective in producing desirable changes within the SCI molecule. These are:

charge reversal;

charged residue to neutral;

hydrophobic to hydrophilic.

For optimum results substitutions should be made at particular sites within the molecule. The residues which should be altered are dependent on the level of multimerisation which is to be prevented.

The following discussion of preferred sites for mutation deals primarily with LD78, the proposed structure of which is shown in FIG. 1b of WO-A-9313206 which corresponds to pending U.S. Ser. No. 07/982,759, filed Mar. 8, 1993. In FIG. 1b of that application, the ribbon traces the predicted path of backbone atoms for the LD78 monomer. The labelled residues define the putative secondary structure elements. β-sheet strand 1 runs from Phe23 to Thr30; β-sheet strand 2 runs from Lys35 to Thr43; β-sheet strand 3 runs from Ser46 to Pro53; and the C-terminal helix runs from Trp57 to Ala69. Analogous secondary structural elements may be inferred for other SCIs, including MIP-1α, for example using the amino acid alignment shown in FIG. 1a of WO-A-931320 which corresponds to pending U.S. Ser. No. 07/982,759, filed Mar. 8, 1993.

It is apparent that some faces of the monomer are involved in more than one part of the multimerisation pathway. The extent of disruption/inhibition of self-association in those faces is related to the nature of the amino acid substitution.

Inhibition of monomer to dimer formation can be achieved by one or more mutations, for example at residue 19 (H1e) or 39 (Val). Either residue may be changed to Ala.

Dimer to tetramer formation is affected by mutations in residues projecting away from the surface of the dimer in strand 1 of the, β sheet, and/or in the turn between strands 2 and 3 of the β sheet. Examples of the first region are amino acids 24–29 of LD78 SEQ ID NO.2 and of the second region are amino acids 43–47 of LD78 SEQ ID NO.2. In particular, Phe23>Ala, Ile24>Asn, Tyr27>Asn, Phe28>Glu, Glu29>Arg, Lys44>Glu (especially with Arg45>Gln) and Arg 45>Glu are preferred.

Tetramer to dodecamer formation can be inhibited or disrupted by mutations of the nature described above in either the residues which form a chain N-terminal to the turn into strand 1 of the sheet (where two changes are preferred), particularly residues 16–21, especially 17–19 or at position 4, 12, 26, 44, 48, 56 or 66 of LD78 SEQ ID NO.2. In particular, Ala4>Glu, Phe22>Asp, Arg17>Ser, Asp26>Ala (especially with Gln18>Glu), Arg17>Glu (again especially with Gln18>Glu), Asp26>Ala, Lys44>Ser, Gln48>Glu (especially with Phe28>Glu) Glu56>Ser and Glu66>Ser are preferred.

Dodecamer to higher order multimer formation is prevented or disrupted by mutations at positions 12 to 21, especially positions 12, 18 and 21, of LD78 SEQ ID NO.2, or at position 65. In particular, Phe12>Gln, Gln18>Glu, Glu21>Ser and Leu65>Ala are preferred.

Generally preferred LD78 SEQ ID NO.2 analogues of the invention include molecules which comprise a sequence substantially corresponding to LD78 SEQ ID NO.2, but with a mutation at one or more (but preferably no more than two) of the following amino acid residues: Ser1, Leu2, Ala3, Ala4, Asp5, Thr6, Ala9, Phe12, Ser13, Tyr14, Ser16, Arg17, Gln18, Ile19, Pro20, Gln21, Phe23, Ile24, Asp26, Tyr27, Phe28, Ser31, Ser32, Gln33, Ser35, Lys36, Pro37, Gly38, Val39, Ile40, Leu42, Thr43, Lys44, Arg45, Ser46, Arg47, Gln48, Asp52, Glu55, Glu56, Gln59, Lys60, Tyr61, Val62, Asp64, Leu65, Leu67, Glu66, Ser68, and Ala69.

Preferred LD78 SEQ ID NO.2 analogues in accordance with the invention include Lys44>Glu (with Arg45>Gin), Arg47>Glu, Phe28>Glu, Phe28>Glu (with Gln48>Glu), Phe28>Glu (with Arg47>Glu), Arg17>Ser (with Gln18>Glu), Phe12>Ala, Val39>Ala, Ile40>Ala, Asp26>Ala (with Glu29>Arg and Arg47>Glu). More preferred LD78 SEQ ID NO.2 analogues in accordance with the invention include Arg17>Ser, Glu29>Arg, Gln18>Glu, Asp26>Ser, Glu48>Ser, Thr15>Ala, Gln21>Ser, Phe23>Ala, Ser32>Ala, Ala51>Ser, Ala4>Glu, Phe12>Asp, Asp26>Gln, Lys36>Glu, Lys44>Glu, Arg45>Glu, Glu56>Ser, Glu66>Gin. The most preferred LD78 SEQ ID NO.2 analogues in accordance with the invention are Phe12>Gln, Lys44>Ser, Arg17>Glu (with Gln18>Glu) and, especially, Asp26>Ala and Glu66>Ser. Generally preferred mu-MIP-1α analogues of the invention include molecules which comprise a sequence substantially corresponding to muMIP-1α, but with a mutation at one or more (but preferably not more than two) of the following amino acid residues: Ala1, Pro2, Tyr3, Gly4, Ala5, Asp6, Thr7, Ala10, Phe13, Ser14, Tyr15, Ser16, Arg27, Lys18, Ile19, Pro23, Arg21, Phe23, Ile24, Asp26, Phe28, Glu29, Ser31, Ser32, Glu33, Ser35, Gln36, Pro37, Gly38, Val39, Ile42, Leu42, Thr43, Lys44, Arg45, Asn46, Arg47, Gln48, Asp52, Glu55, Thr56, Gln59, Glu60, Tyr61, Ile62, Asp64, Leu65, Glu66, Leu67, Asn68 and Ala69.

Preferred muMIP-1α analogues of the invention correspond to the preferred LD78 analogues described above.

Molecules in accordance with the invention will for preference be free of N-terminal extensions preceding Ser-1 (in the case of LD78) or Ala-1 (in the case of MIP-1α).

Engineered or natural variants containing an amino acid substitution at one or more of the aspartic acid or glutamic acid side-chains are especially preferred in the present invention. Examples include LD78(Asp26>Ala), LD78 (Glu56>Ser), LD78(Phe12>Gln), LD78(Arg17>Ser), LD78 (Glu66>Ser), LD78(Asp26>Ser) and LD78(Phe23>Ala) according to LD78 SEQ ID NO.2.

The invention is particularly useful in inducing leukophilia, for example neutrophilia, in various disease states. For example neutropaenia may arise as a result of microbial (such as bacterial) infection; the neutropaenia can be addressed by inducing neutropheilia. Other diseases of which neutropaenia is a symptom or cause may also be treated by means of the invention, possibly in conjuction with cytotoxic agents. Such diseases are exemplified by, but not limited to, the following:

congenital neutropaenias such as Kostmann's syndrome and Schwachman-Diamond syndrome;

childhood and adult cyclic neutropaenia;

post-infective neutropaenia;

myelo-dysplastic syndrome; and neutropaenia associated with chemotherapy and radiotherapy.

The observation described above is surprising because there is no report in the literature of SCI proteins having acute effects on mature neutrophils. Most of the reports relate to the effects of SCI in inhibiting the proliferation of early haematopoietic progenitors, or stimulating division of later more committed progenitors. The acute effects of SCI have been examined using a number of myeloid cell lines; for example, it has been shown that $Ca^{2+}$ influx is triggered by SCI in the monocyte-like line THP-1. However, such studies were not related to likely in vivo effects. Such cell lines are of limited utility as models of mature cell function, and cannot be used to predict in vivo effects of an agent.

A number of other agents such as FMLP, IL-8 and LPS are known to induce neutropilic responses similar to those we observe with SCIs (Jagels and Hugli, *J. Immunol.* 148 1119–1128 (1992)). These molecules were investigated because of their known role as potent inflammatory mediators. However, LD78 appears to exert its neutropil effect independent of any inflammatory action.

The invention is useful in inducing the release of mature cells and committed progenitor cells of the myeloid lineage. Committed progenitors are formed by division of the true stem cells. These more differentiated, but not fully differentiated, daughter cells have greater proliferative potential in the true stem cell, but can only differentiate into specific cell types. Mature myeloid cells include granulocytes (comprising neutrophils, eosinophils and basophils), macrophages and lymphocytes. An increase in the circulating number of macrophages and lymphocytes may be particularly useful in potentiating the body's response to infection and tumours. Such an increase may also be important in the treatment of severe chronic neutropaenia. Macrophages are involved in the acute inflammatory response, and in the response to bacteria and parasites. An increase in granulocytes may help fight acute or chronic microbial, fungal and parasite infection, and tumours; for example, eosinophilia is a marked feature of the immune response to helminthic infection.

The invention is also useful in inducing the release of haematopoietic stem cells. This may be particularly relevant in the harvesting of cells before chemotherapy, to protect the cells from the harmful effects of the treatment. Until the present invention, G/GM-CSF have been used to release stem cells from marrow so that they can be harvested before chemotherapy. This treatment generally takes 4 to 7 days but can take up to 12 days, and the timing of the appearance of cells in the blood is unpredictable. It is therefore highly beneficial to the patient to be able to use SCI treatment which releases a significant percentage of the marrow cells in a predictable fast time, for example about 30 minutes.

It is particularly surprising that SCIs, while biting stem cell proliferation, should also be involved in the mobilisation and release of these cells from the marrow. This invention is the first observation of the release of haematopoietic stem cells from the marrow by chemokine administration.

The potential utility of SCI as a stimulator of the release of haematopoietic cells from bone marrow appears hitherto to have been overlooked, possibly because of the overriding interest in its role as a negative regulator.

Finally, SCIs have now been shown to have an enhanced effect when co-administered with colony-stimulating factors. Co-administration of SCI with G-CSF causes the enhanced mobilisation of a number of cell types, for example neutrophilis, monocytypes, eosinophils, lymphocytypes and basophils. This is particularly surprising as we have shown that G-CSF alone has no effect on the release of eosinophils or basophils after 2 days administration. Similiar effects may be observed when other agents such as (GM-CSF, f-Met-Leu-Phe or IL-8 are co-administered with SCI.

The invention thus has a clear clinical indication as a replacement for, or adjunct to, the use of CSFs in peripheral blood cell transplantation. Peripheral blood cell transplantation is an important procedure in the treatment of cancer patients with high dose chemotherapy. In such treatments, patients are treated to induce clinical remission of their cancers; then during the remission, successive treatments with CSF, for example by priming with cyclophosphamide then administration of G-CSF, cause eventual mobilisation of cells from the bone marrow to the peripheral circulation for harvesting of leucophoresed blood; then the patient is given high dose chemotherapy or radiotherapy and the result bone marrow failure is compensated for by infusion of the stored blood or cells collected previously. The foregoing procedure may be modified by omission of the initial induction of remission, and whole blood may be collected rather than leukophoresed blood. According to the invention, the mobilisation effects of SCIs makes them candidates both to replace CSF's in such cancer treatment regimes, and also to complement the mobilisation effects of CSFs injoint CSF/SCI treatments. Mobilisation of stem cells, progenitors and neutrophils from the marrow occurs more rapidly with SCI than with CSFs, and SCIs synergise with CSFs to produce a predictable, fast and enhanced yield of stem cells, progenitors and neutropils, potentially obviating the need for repeated aphoresis. In summary, SCIs offer the following advantages: (i) they reducee need for CSF and/or priming chemotherapy; (ii) they give enhanced yields of stem cells, progenitors and leucophils; and (iii) they offer a more predictable and manageable regime for peripheral blood cell tansplantation.

The effect of SCIs in inducing leukophilia will find clinical and veterinary application in all utilities where the raising of haematopoietic cell levels is important. For example, SCIs may be used to enhance immune responses against chronic infections, particularly parasitic and bacterial infections. They may also have a role in promoting wound healing. The haematopoietic stem cells released and harvested in the manner described above may also be useful for subsequent in vitro, or at least ex vivo, manipulation to deliver gene products in gene therapy. Co-administration with cytotoxic drugs is another endpoint.

Co-administration with an immunogen could likewise lead to enhanced immune responses and thus better acquired immunity. The augmentation of the immune response may be either qualitative, for example an enhanced CTL response or antibody response, or a redirection of responses from Th1 to Th2 type responses or vice versa where appropriate.

Therefore, according to a second aspect of the invention there is provided a prophylactic or immunotherapeutic vaccine formulation having stem cell inhibition activity and immunogenic activity. The formulation may comprise a stem cell inhibitor and an immunogen.

The stem cell inhibitor, which will generally be proteinaceous, may simply be in admixture with the immunogen. However, it may be administered separately. According to a third aspect of the invention, therefore, there is provided a product comprising a stem cell inhibitor and an immunogen for separate, simultaneous or sequential administration in immunotherapy or prophylaxis.

The immunogen may correspond to a sequence derived from or associated with an aetiological agent or a tumour. The aetiological agent may be a microorganism such as a virus, bacterium, fungus or parasite. The virus may be: a retrovirus, such as HIV-1, HIV-2, HTLV-I, HTLV-II, HTLV-III, SIV, BIV, LAV, ELAV, CIAV, murine leukaemia virus, Moloney murine leukaemia virus or feline leukaemia virus; an orthomyxovirus, such as human influenza A, B or C, or horse or cat influenza; a paramyxovirus, such as parainfluenza virus, mumps, measles, RSV or Sendai virus; a papovavirus, such as HPV; an arenavirus, such as LCMV of human or mice; a hepadnavirus, such as Hepatitis B virus; or a herpes virus, such as HSV, VZV, CMV, or EBV. The tumour-associated or derived antigen may for example be a proteinaceous human tumour antigen, such as a melanoma-associated antigen, or an epithelial-tumour associated antigen such as from breast or colon carcinoma, or an oncogene product such as the raf tumour gene.

The antigenic sequence may be also derived from a bacterium, such as of the genus Neisseria, Campylobacter, Bordetella, Listeria, Chlamydia, especially *C. trachomatis*, Mycobacterium or Leishmania, or a parasite, such as from the genus Trypanosoma, Schizosoma, Plasmodium, especially *P. falciparum*, or from a fungus such as from the genus Candida, Aspergillus, Cryptococcus, Histoplasma or Blastomyces.

Preferred antigenic sequences correspond to epitopes from a retrovirus, a paramyxovirus, an arenavirus or a hepadnavirus, or from a human tumour cell. Examples include epitopes from:

1) HIV (particularly HIV-1) gp120,
2) HIV (particularly HIV-1) p24,
3) VZV gpI, gpII and gpIII,
4) LCMV nucleoprotein,
5) influenza virus nucleoprotein,
6) Influenza matrix protein, haemagglutonin or neuraminidase,
7) HPV L1 and L2 proteins,
8) Human papilloma virus E5 and E7,
9) Malaria CSP or RESA antigens,
10) Mycobacterium p6,
11) GA 733-2 epithelial tumour-associated antigen,
12) MUC-1 repeat sequence from epithelial tumour-associated antigen,
13) Melanoma MZ2-E antigens and
14) Melanoma p97 associated antigen.

Vaccine formulations will generally be adapted for parenteral administration and be sterile. An aqueous carrier such as water for infections, physiological saline or phosphate-buffered saline (PBS) will generally be present. The use of PBS is preferred if a demultimerised form of SCI is to be used. One or more appropriate adjuvants (apart from the stem cell inhibitor itself, if that is functioning as an adjuvant) may also be present. Examples of suitable adjuvants include muramyl peptide compounds such as prototype muramyl dipeptide, aluminium hydroxide and saponin. Other diluents and/or adjuvants and if desired other active ingredients may additionally be present. Non-vaccine formulations would generally be formulated similarly.

The active ingredient may be administered parenterally in a sterile medium. Depending on the vehicle and concentration used, the drug can either be suspended or dissolved in the vehicle. Advantageously, adjuvants such as a local anesthetic, preservative and buffering agents can be dissolved in the vehicle.

Therapeutic or prophylactic administration of SCI proteins can be by injection, preferably via i.v. i.p. i.m. or s.c. routes. Other routes such as transdermal, oral, intranasal or by inhalation may also be possible.

Dosage of stem cell inhibitors in accordance with any aspect of the invention will be such as to be effective and will be under the control of the physician or clinician. As general but not exclusive guidance, though, where the SCI is not being administered with an immunogen, doses may be in the range of from 0.031 to 1 mg/kg, preferably from 0.01 to 0.2 mg/kg. Doses may be administered repeatedly, for example from 1 to 6 times per day, preferably from 1 to 3 times per day.

For use as an adjuvant, the SCI can be administered as described above, but preferably by the s.c. or i.m route at a site remote from the primary immunisation. The dose may be in the range of from 0.001 to 1 mg/kg, preferably from 0.01 to 0.2 mg/kg. Preferably only a single dose will be given, at the time of immunisation.

The acute leukophilia observed on administration of SCIs is a very convenient way to monitor the in vivo activity of the molecule. According to a fourth aspect of the invention, therefore, there is provided a method of detecting or assaying in vivo activity of a stem cell inhibitor molecule, the method comprising administering the molecule to an experimental animal and observing a haematopoietic response.

Preferred features for each aspect of the invention are as for each other aspect, mutatis mutandis.

The invention will now be illustrated by the following examples. The examples refer to the accompanying drawings, in which.

Figure 25:
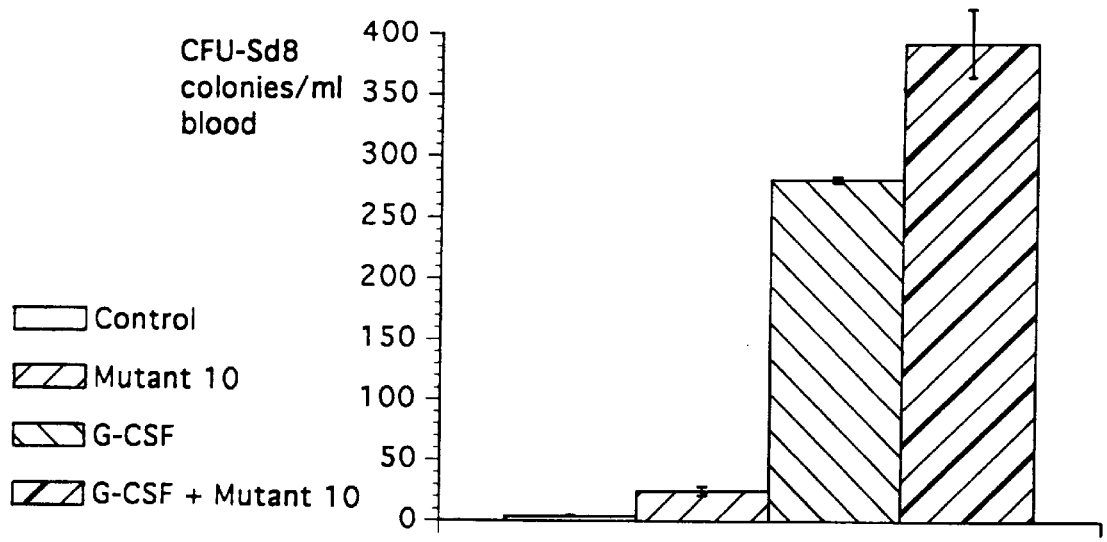

FIG. 25 shows the effect of sequential use of G-CSF (100ug/Kg b.i.d. s.c. for 2 days) and mutant 10 (100ug/Kg s.c.) on the mobilisation of colony forming units spleen day 8 (CFU-Sd8).

Figure 26:
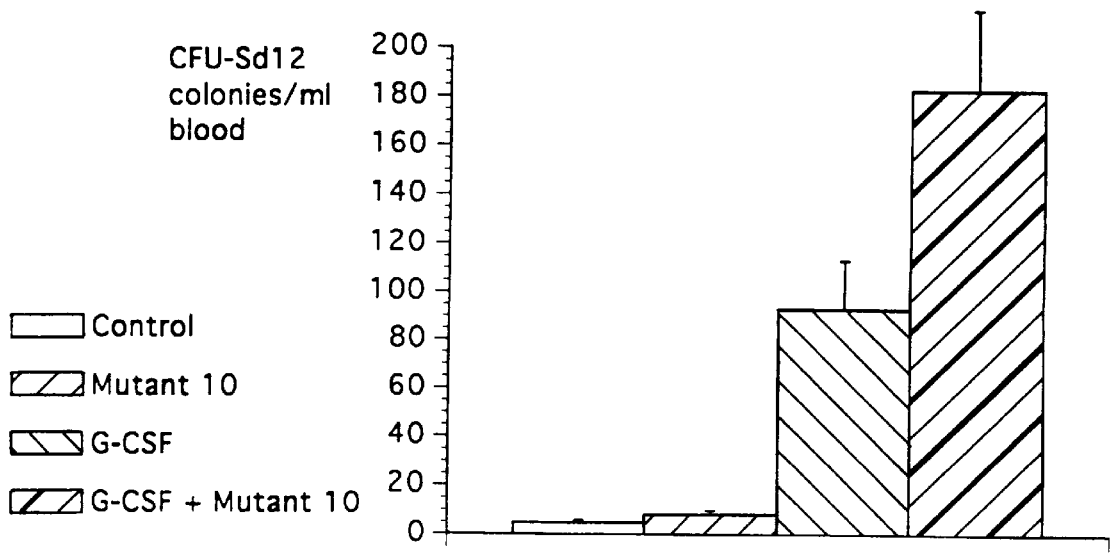

FIG. 26 shows the effect of sequential use of G-CSF ((100ug/Kg b.i.d. s.c. for 2 days) and mutant 10 (100ug/Kg s.c.) on the mobilisation of colony fong units spleen day 12 (CFU-Sd12).

Figure 27:
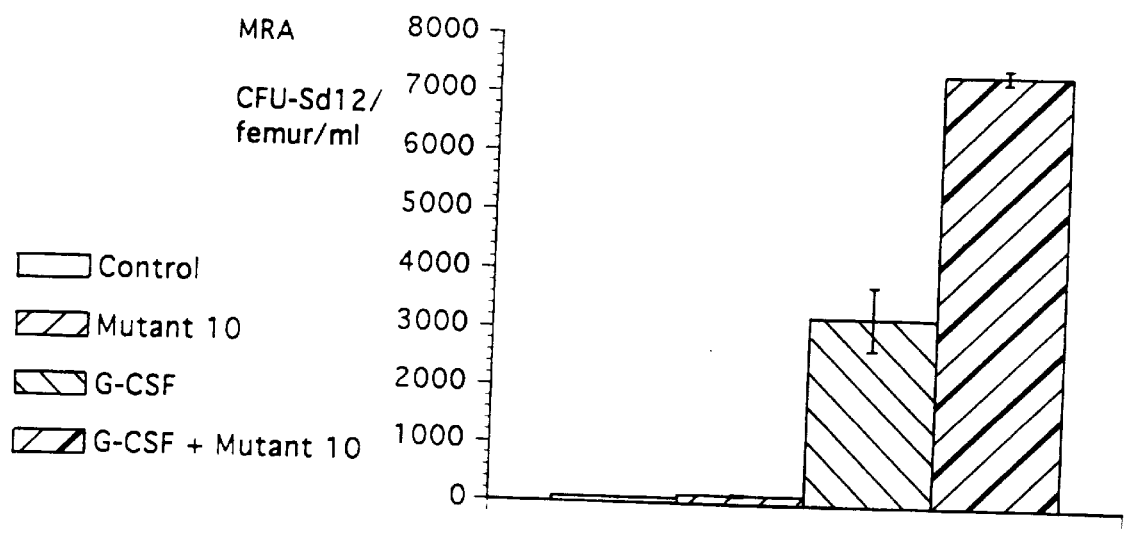

FIG. 27 shows the repopulating ability of the peripheral blood mobilised CFU-S after the sequential use of G-CSF (100ug/Kg b.i.d. s.c. for 2 days) and mutt 10 (10 ug/Kg s.c.).

Figure 28:
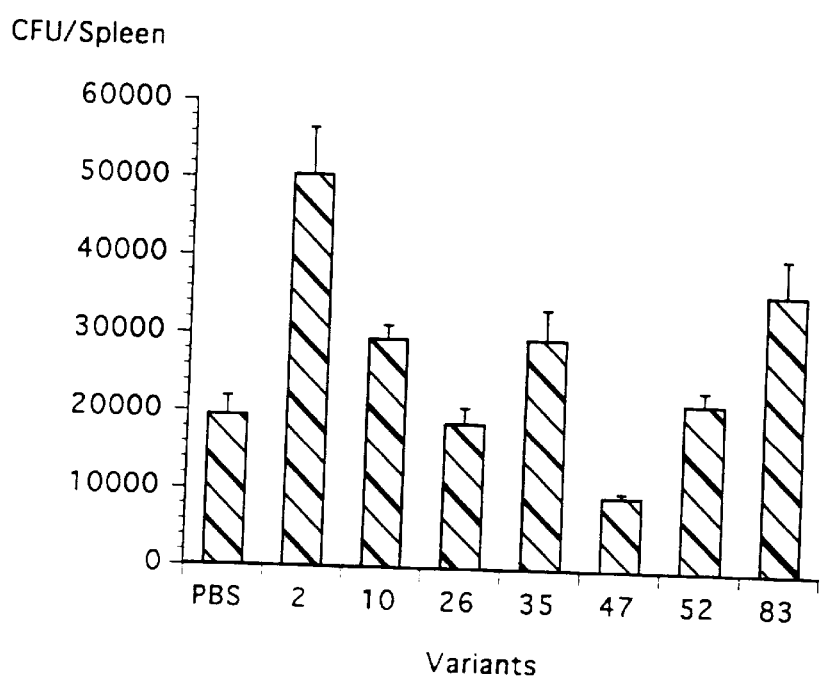

FIG. 28 shows the mobilisation of multipotent progenitors by variants of LD78.

Figure 29:
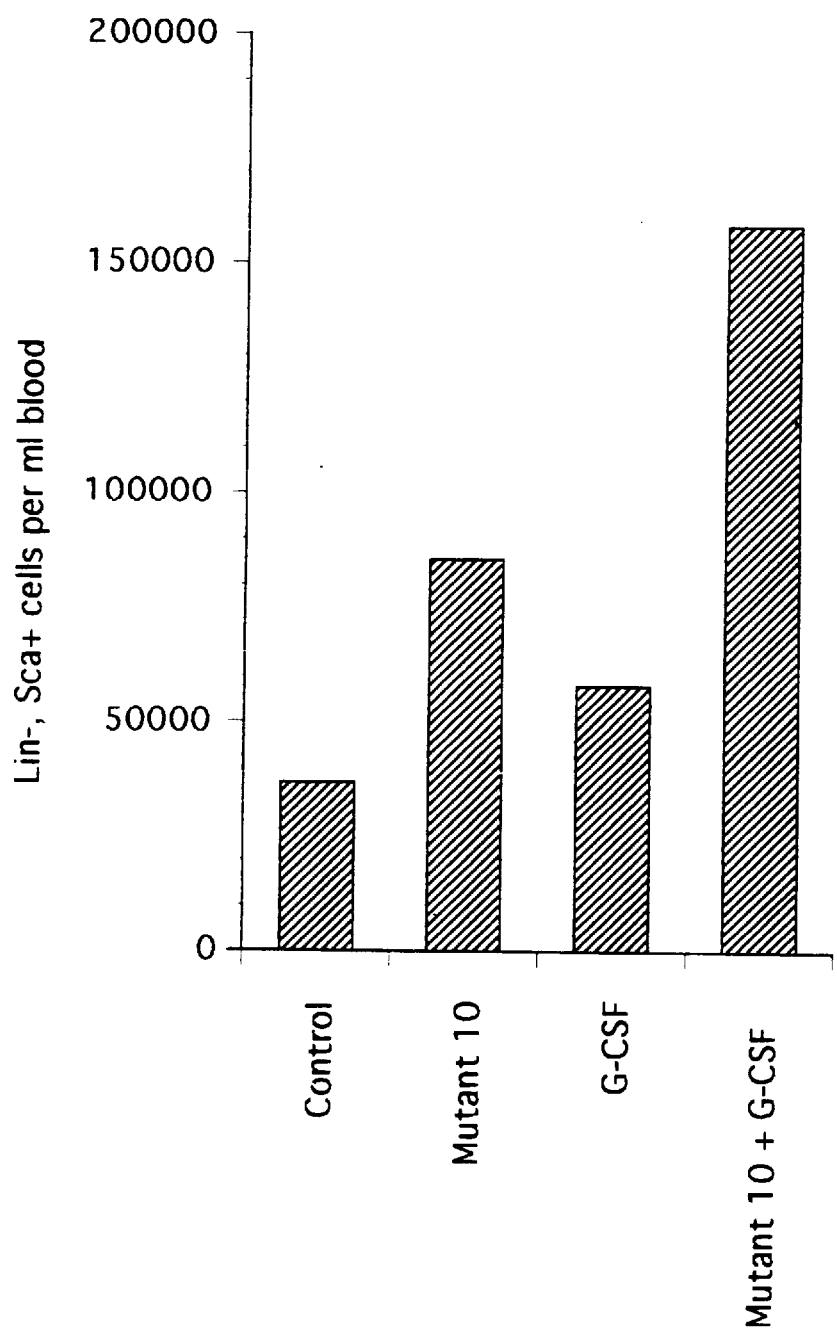

FIG. 29 shows the effect of sequential use of G-CSF and SCI's on the mobilisation of very early progenitors expressing Sca-1+ but not Lin+ cell surface markers.

Figure 30:
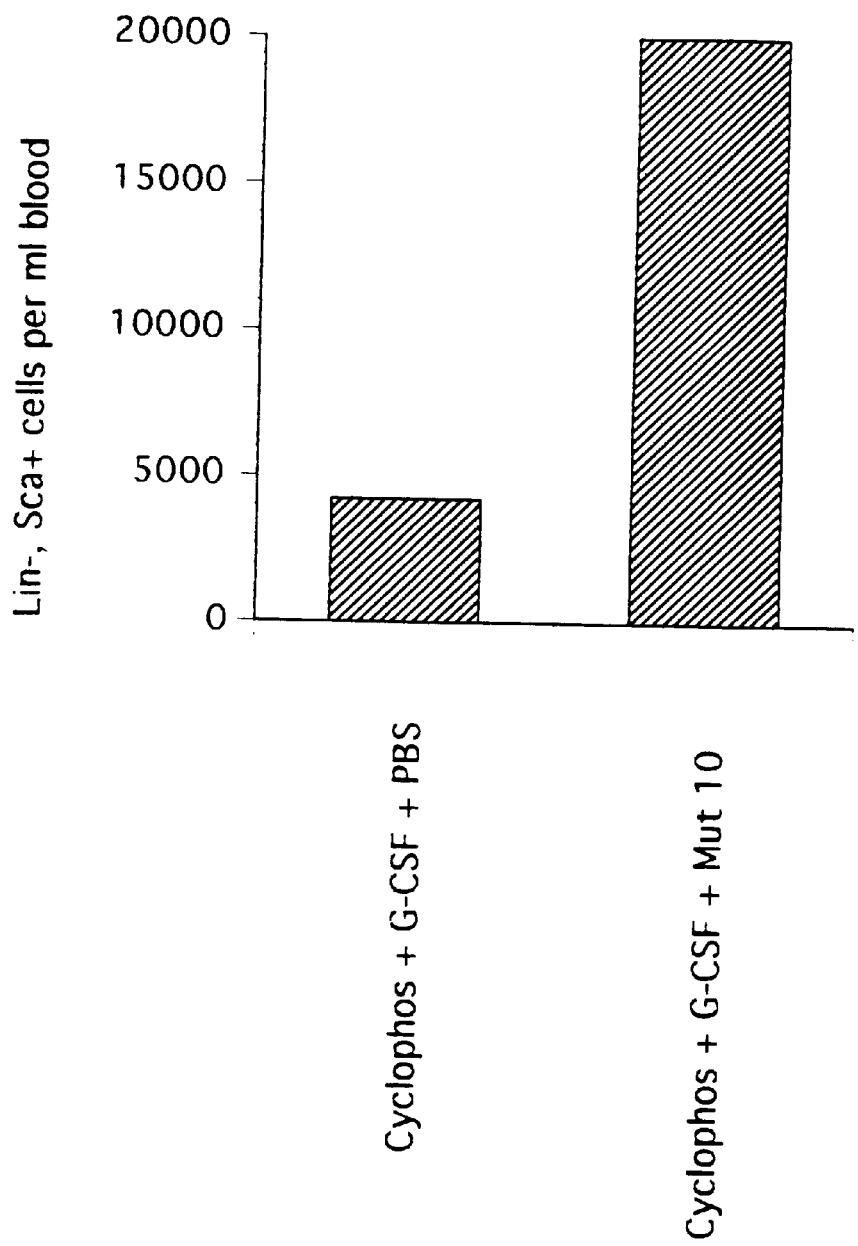

FIG. 30 shows the effect of mutant 10 on the mobilisation of very early progenitors from cyclophosphamide and G-CSF primed mice.

Figure 31:
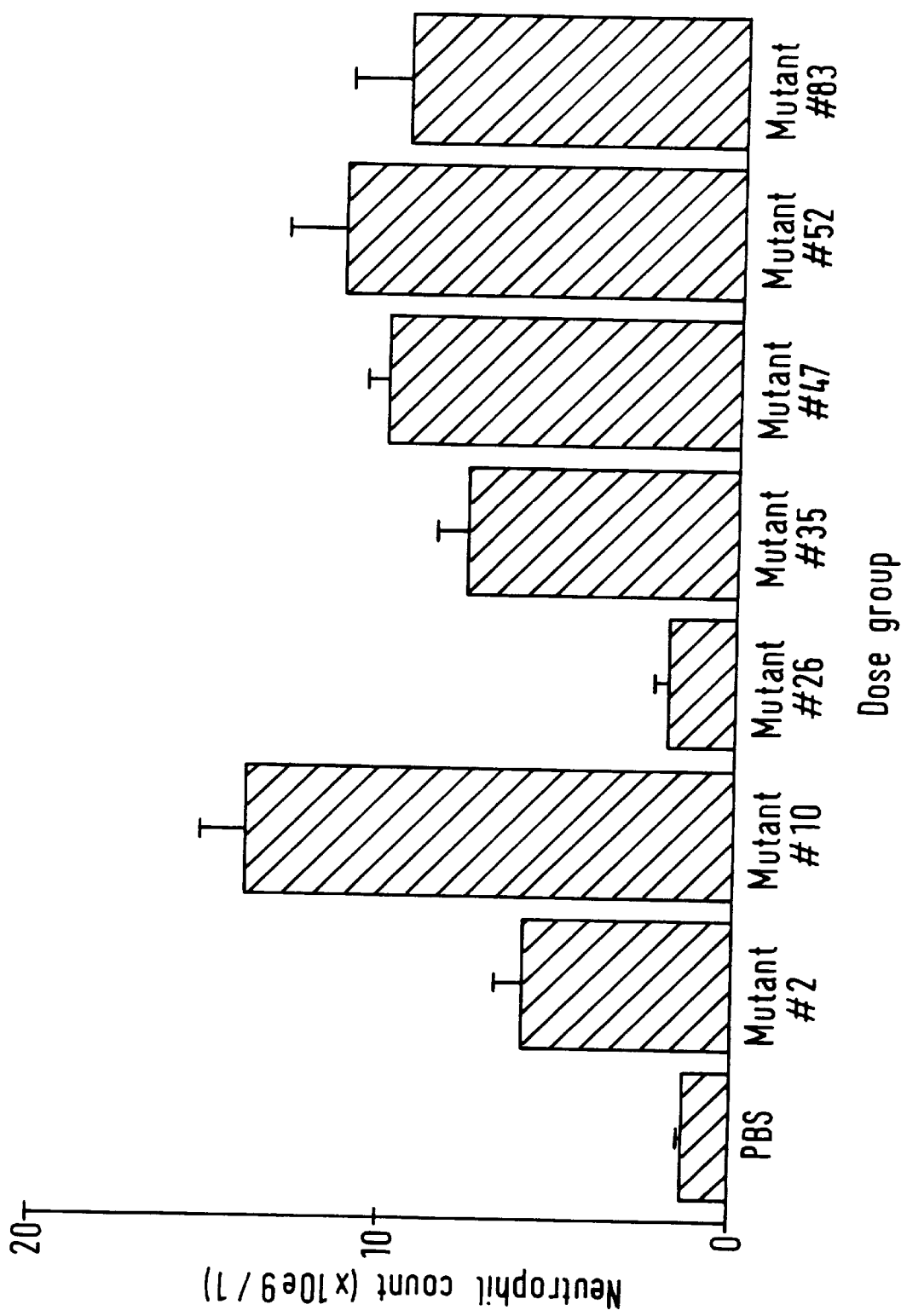

FIG. 31 shows the effect of LD78 variants, 100 µg/kg s.c. on neutrophil count on 2 day G-CSF pre-treated C57BL/6J mice.

Figure 32:
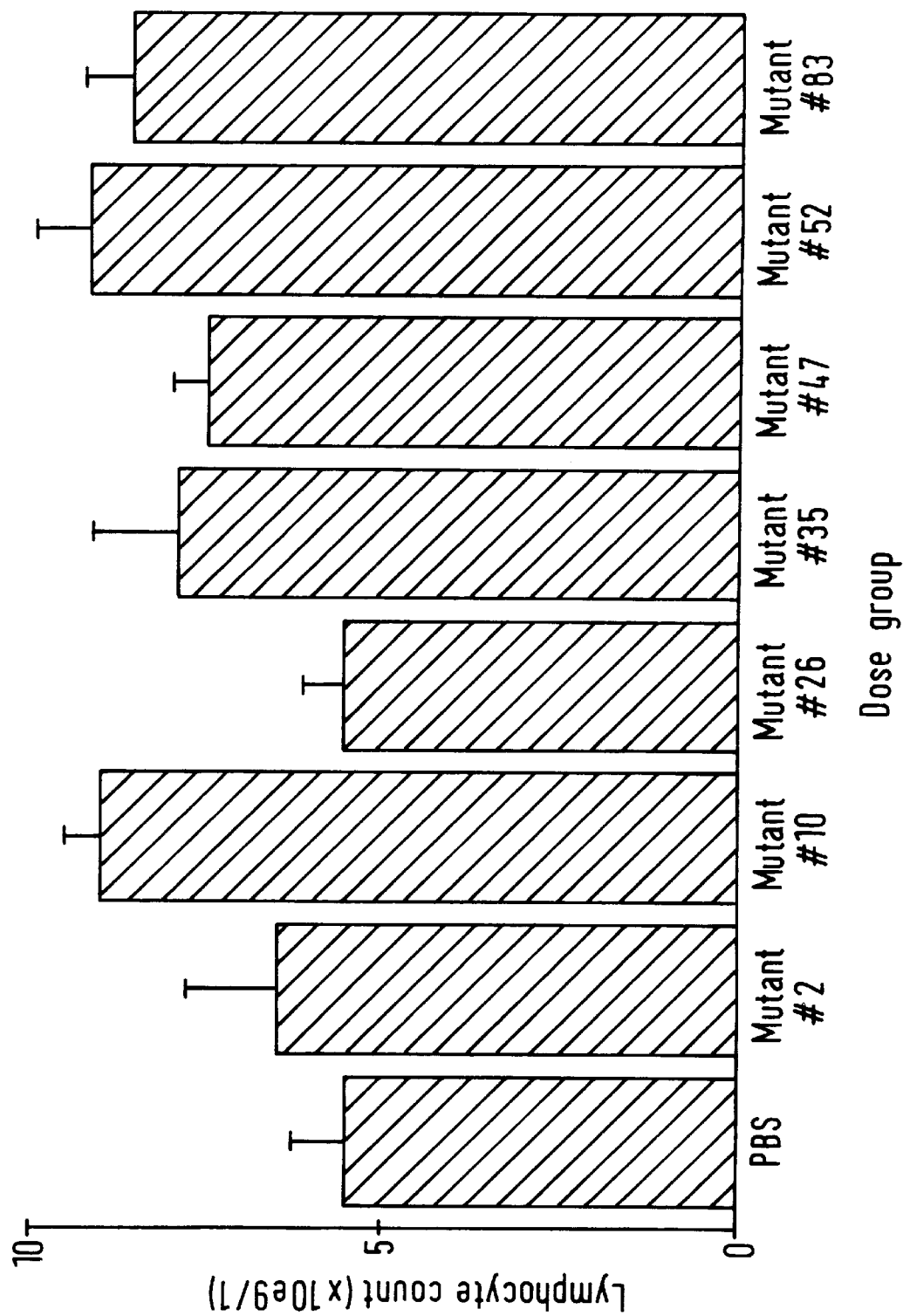

FIG. 32 shows the effect of LD78 variants, 100 82 g/kg s.c. on lymphocyte count on 2 day G-CSF pre-treated C57BL/6J mice.

Figure 33:
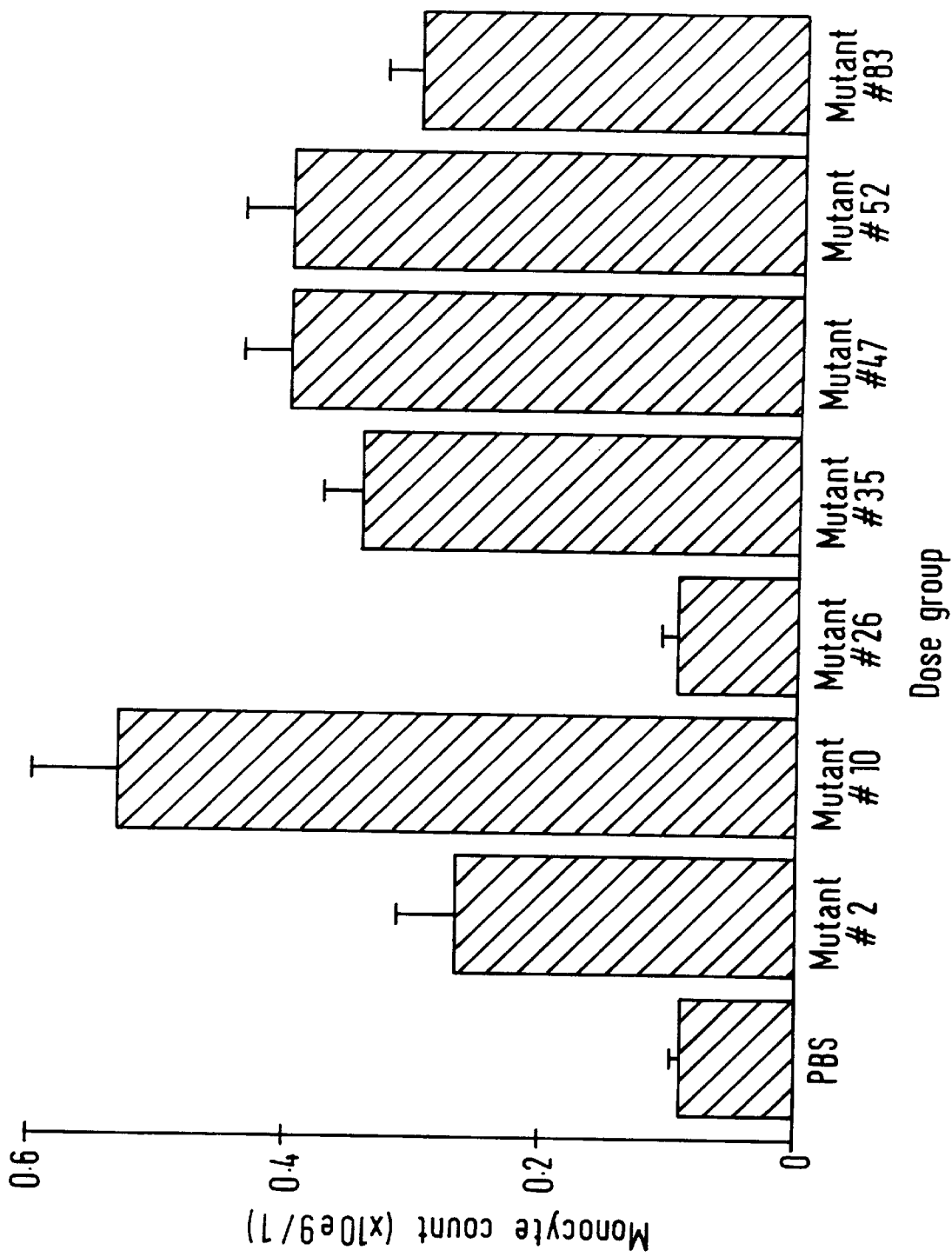

FIG. 33 shows the effect of LD78 variants, 100 µg/kg s.c. on monocyte count on 2 day G-CSF pre-treated C57BL/6J mice.

Figure 34:
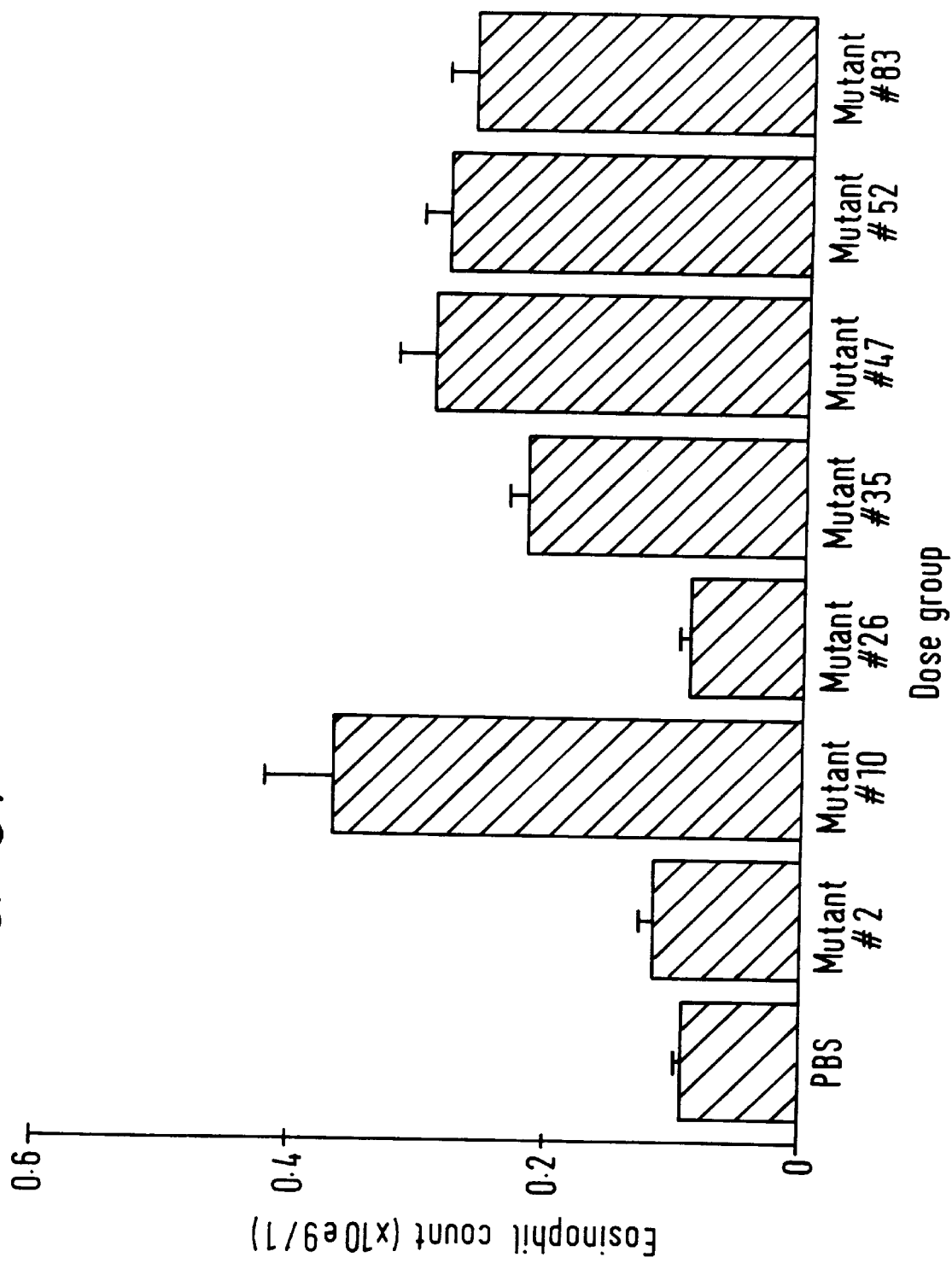

FIG. 34 shows the effect of LD78 variants, 100 µg/kg s.c. on eosinophil count on 2 day G-CSF pre-treated C57DBL/6J mice.

Figure 35:
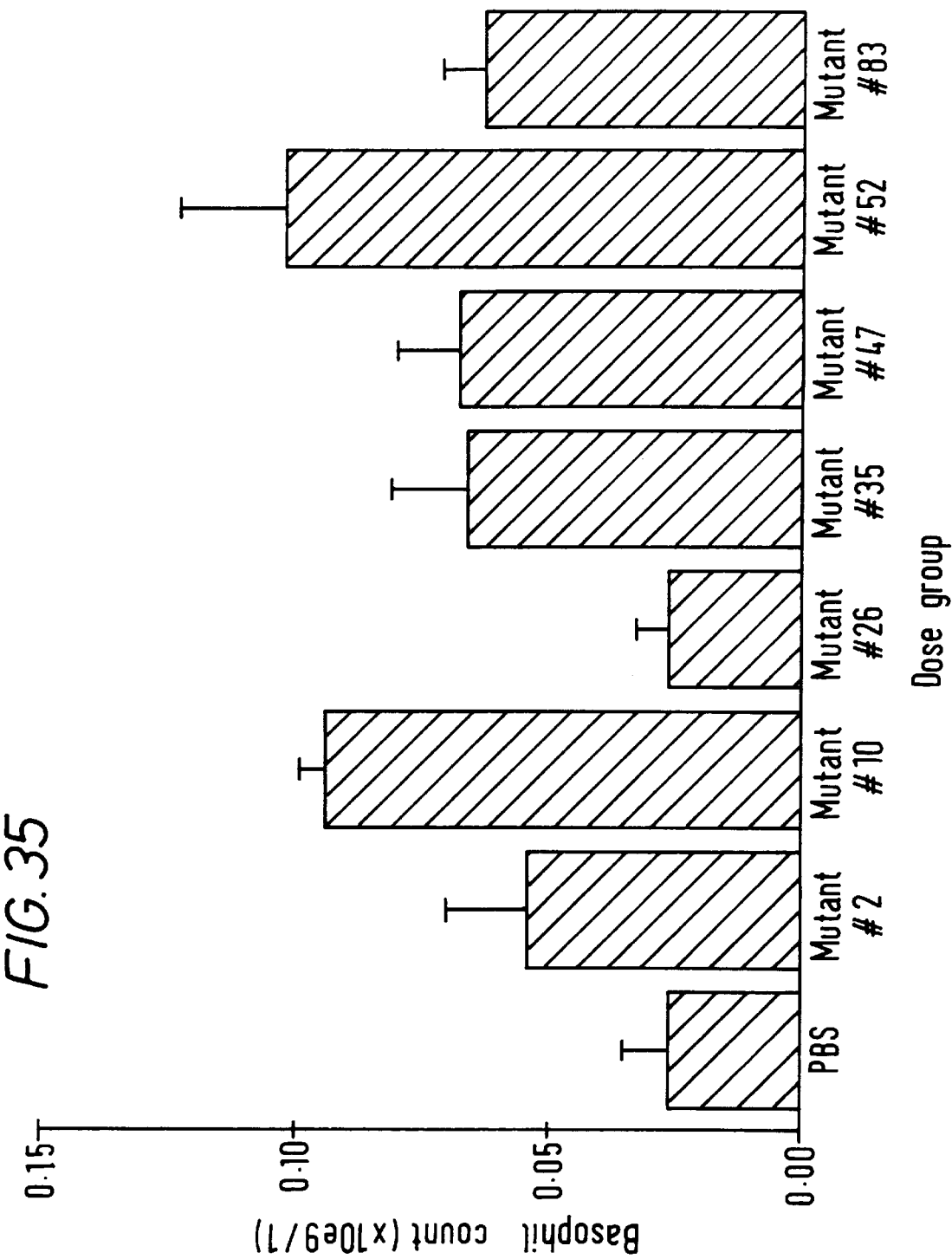

FIG. 35 shows the effect of LD78 variants, 100 µg/kg s.c. on basophil count on 2 day G-CSF pre-treated C57BL/6J mice.

Figure 36:
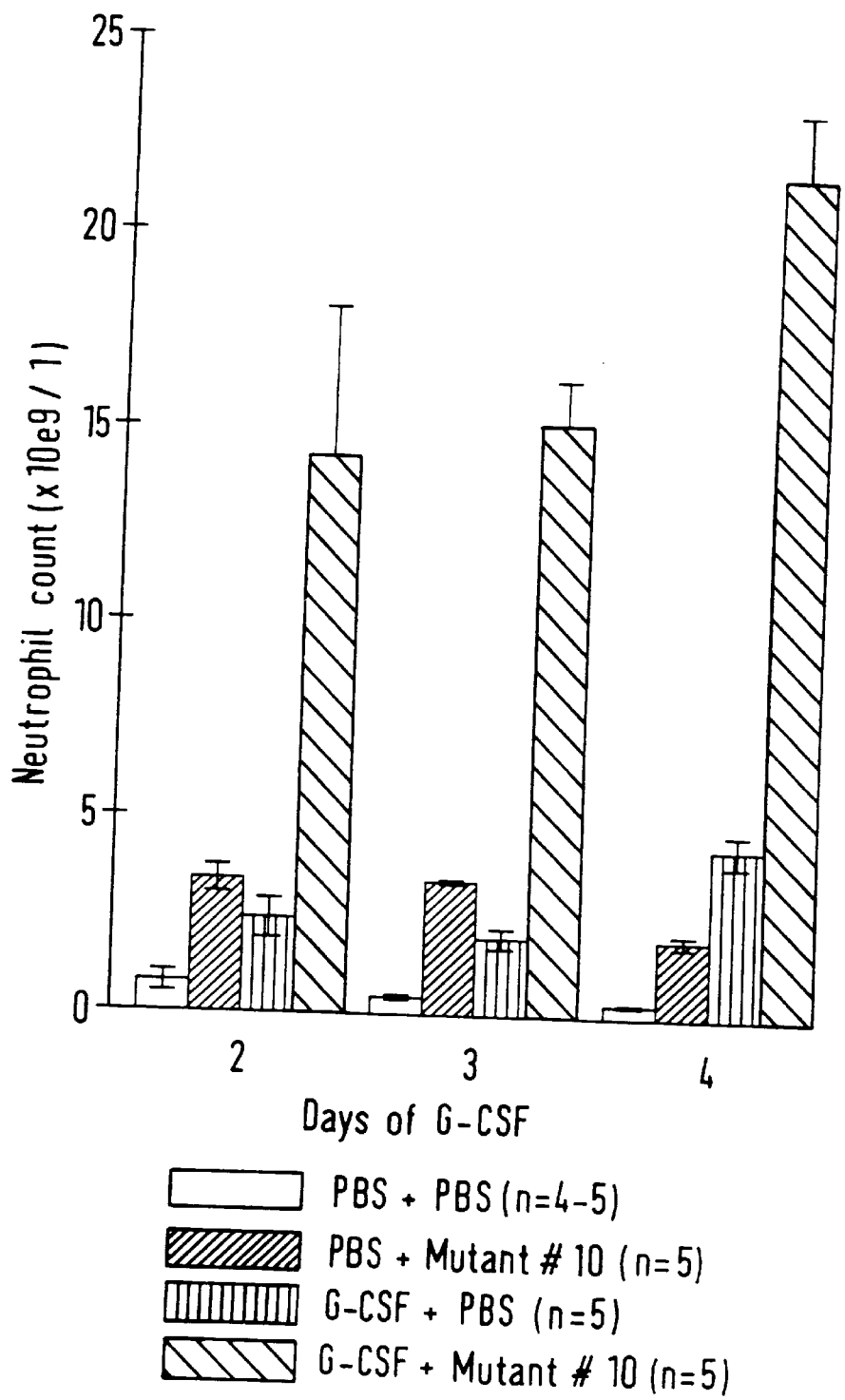

FIG. 36 shows the effect of mutant 10, 100 µg/kg s.c., 30 min prior to sampling on the neutrophil count of G-CSF treated C57BL/6J mice.

Figure 37:
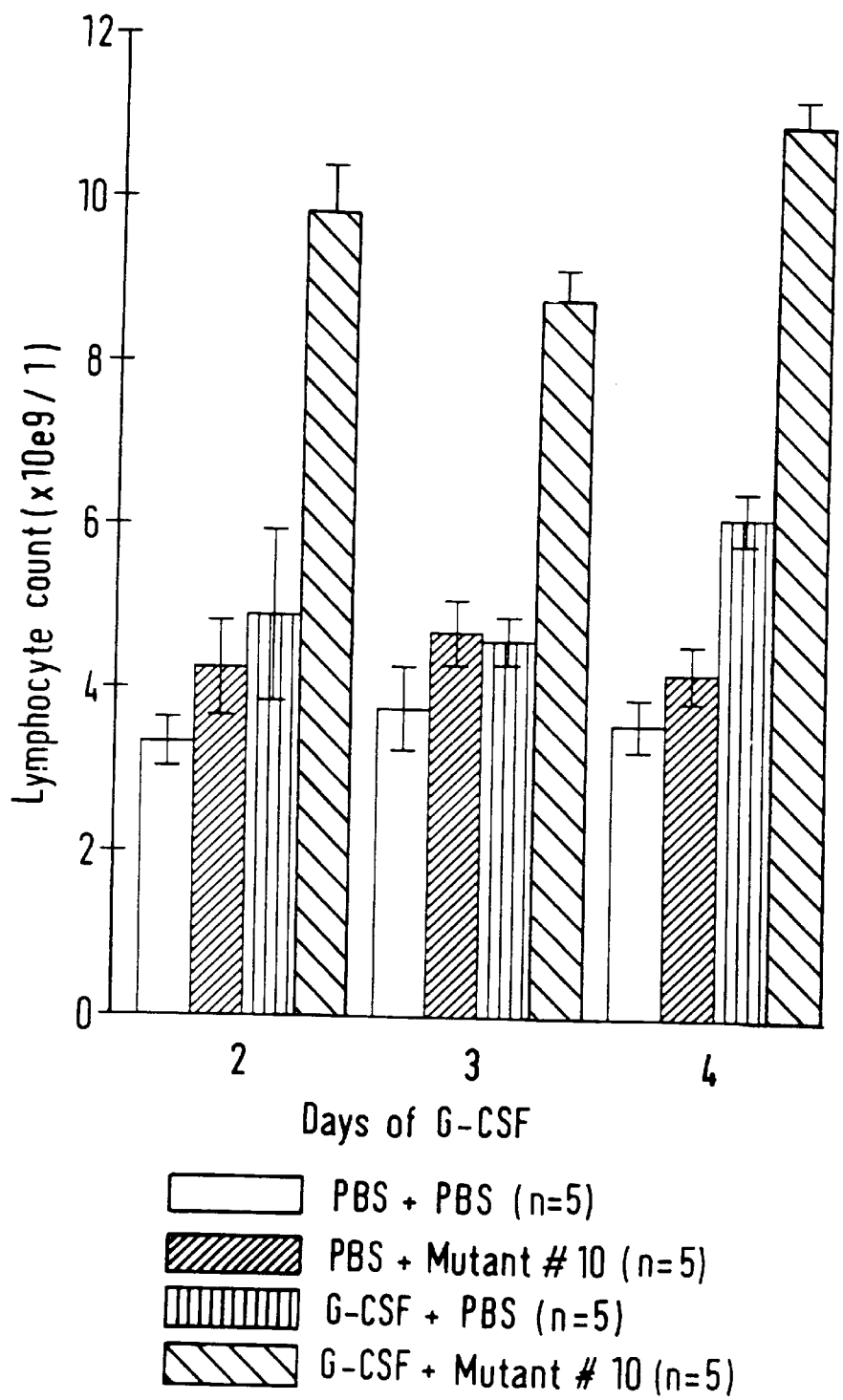

FIG. 37 shows the effect of mutant 10, 100 µg/kg s.c., 30 min prior to sampling on the lymphocyte count of G-CSF treated C57BL/6J mice.

Figure 38:
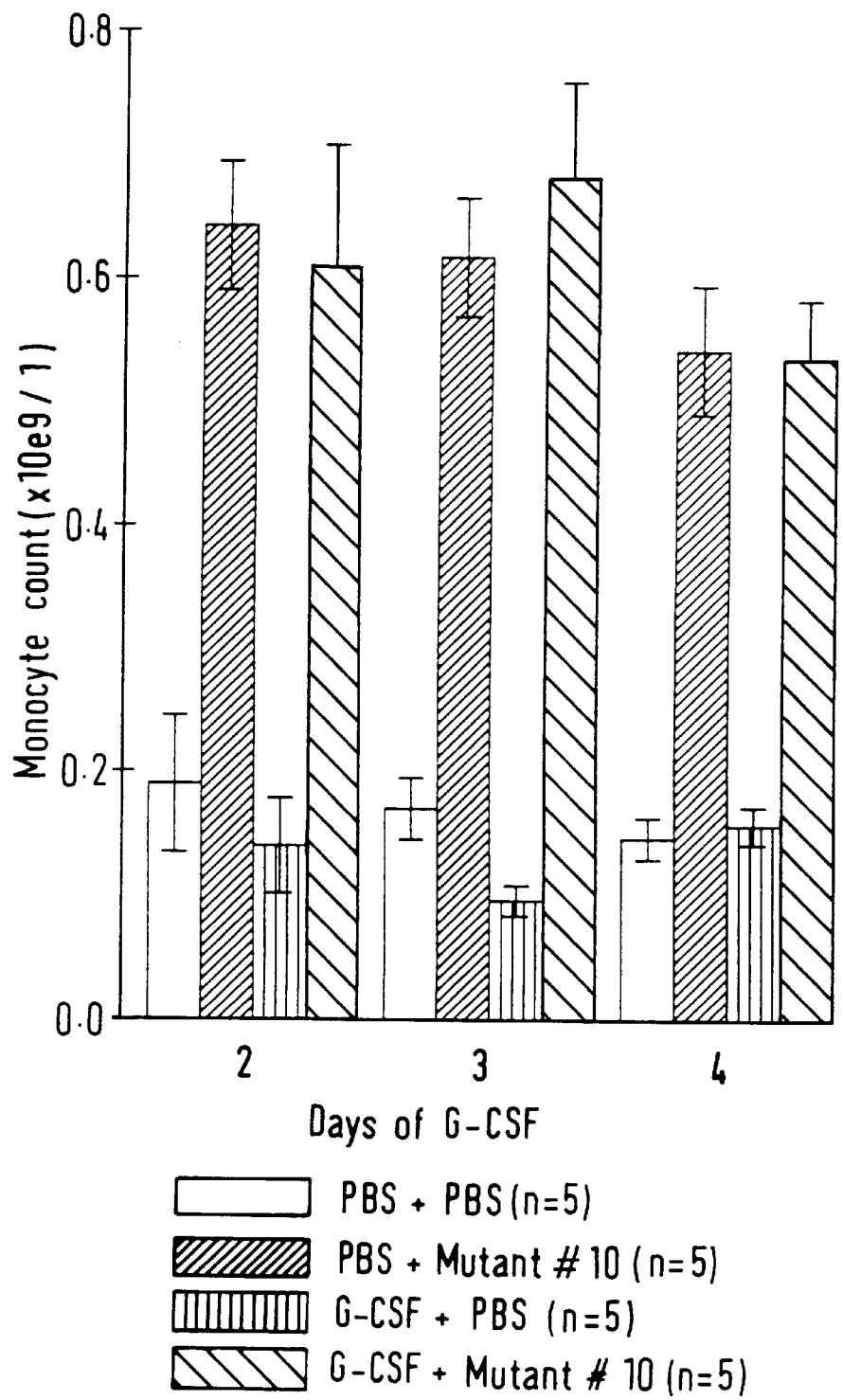

FIG. 38 shows the effect of mutant 10, 100 µg/kg s.c., 30 min prior to sampling on the monocyte count of G-CSF treated C57BL/6J mice.

Figure 39:
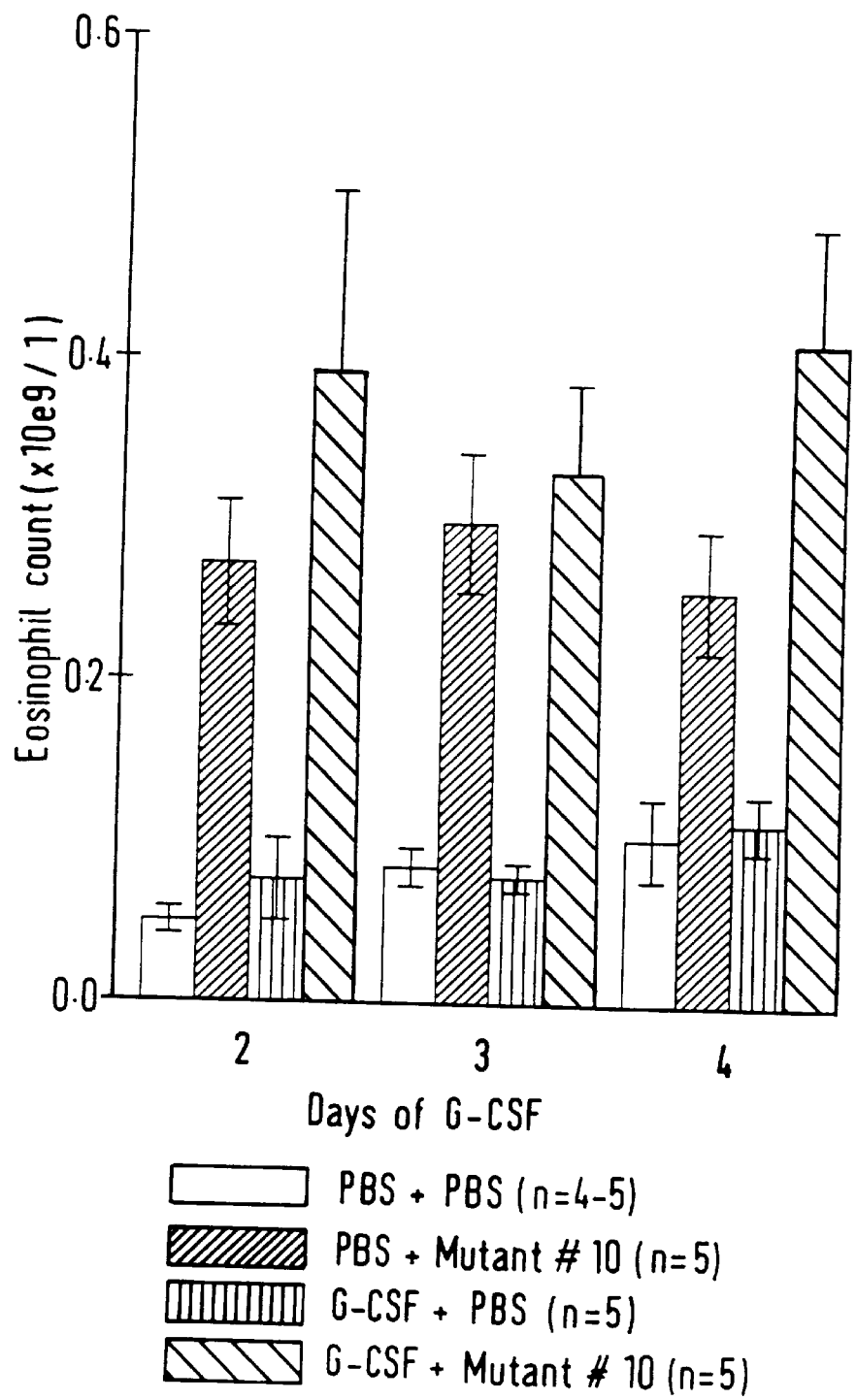

FIG. 39 shows the effect of mutant 10, 100 µg/kg s.c., 30 min prior to sampling on the eosinophil count of G-CSF treated C57BL/6J mice.

Figure 40:
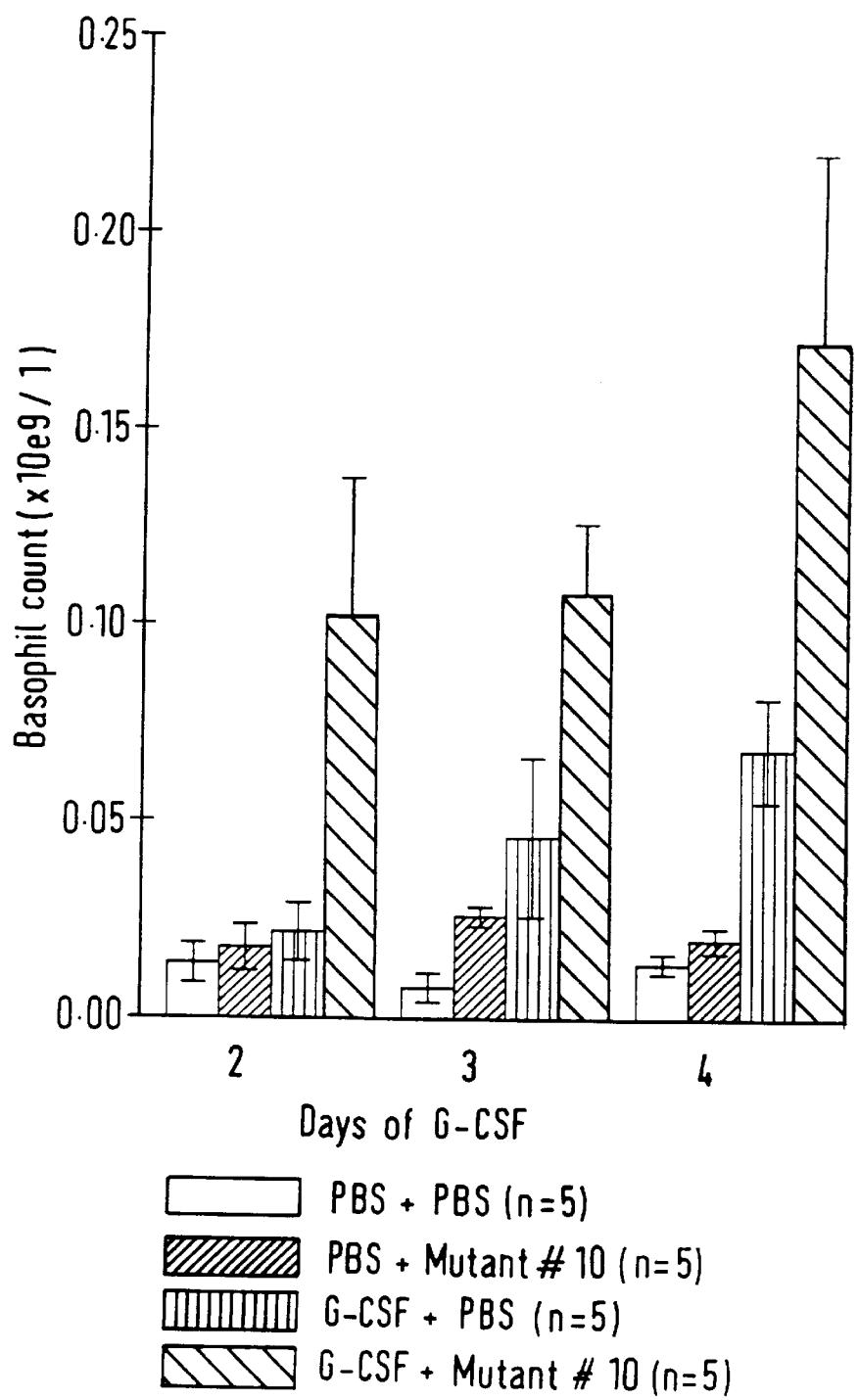

FIG. 40 shows the effect of mutant 10, 100 µg/kg s.c., 30 min prior to sampling on the basophil count of G-CSF treated C57BL/6J mice.

Figure 41:
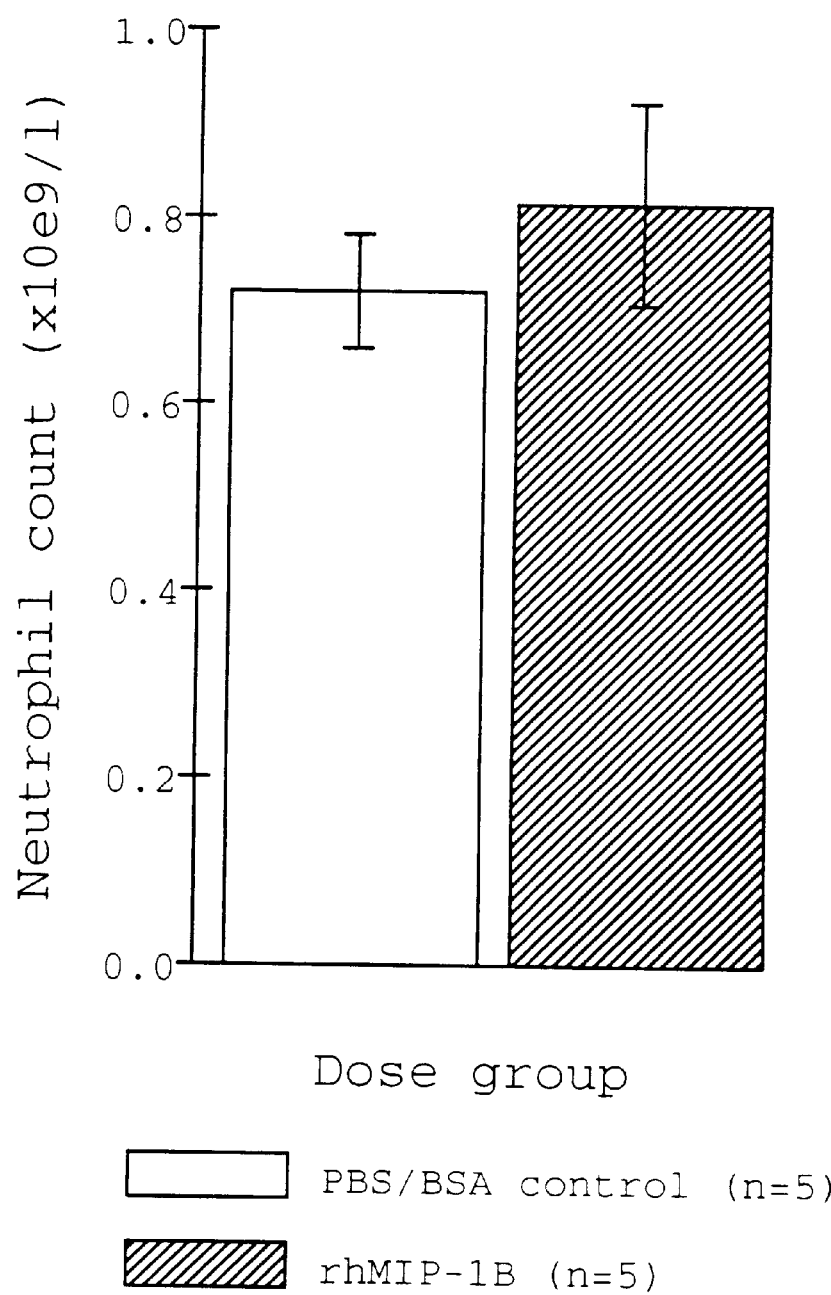

FIG. 41 shows the effect of rhMIP-1α, 100 µg/kg s.c., on the neutrophil count of the BALB/c mouse 30 minutes post dosing.

Figure 42:
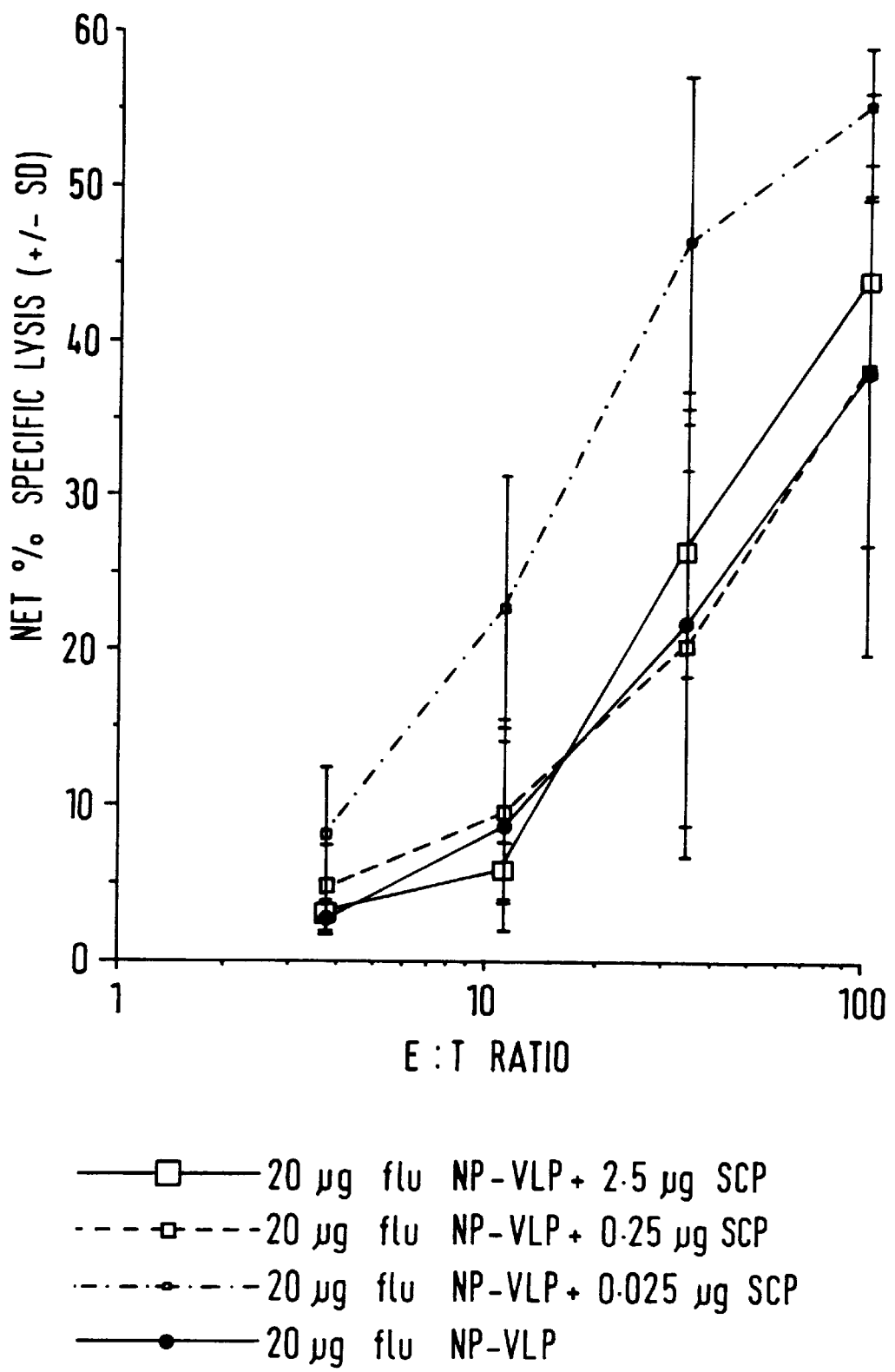

FIG. 42 shows the effect of murine MIP-1α (SCP) on flu specific CTL induction.

Figure 43:
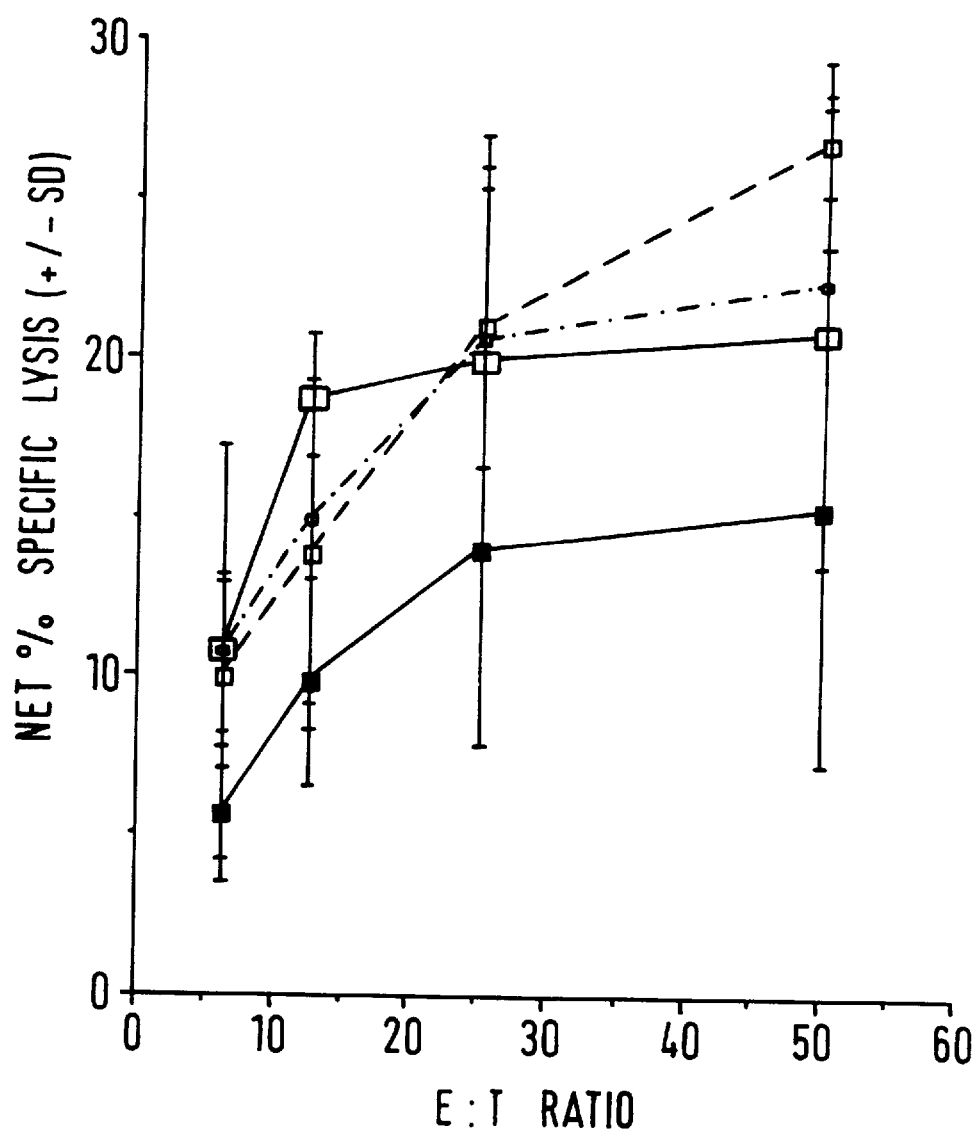

FIG. 43 shows the effect of murine MIP-1α (SCP) on malaria specific CTL induction.

EXAMPLE 1

Effect of LD78 on Neutrophil Recovery Kinetics in a Murine 5-FU Model of Neutropaenia 5-fluorouracil (5-FU) was chosen for study because it is a powerful marrow ablating agent. A model of 5-FU induced neutropaenia was established and the effect of LD78 on neutrophil recovery was examined. A single dose of 5-FU, 150 mg/kg i.p., was given to all mice on day 0 at time 2 hr. Mice were treated with LD78 or placebo (phosphate buffered saline—PBS). LD78 was dosed at 1 mg/kg and 3 mg/kg s.c. at 0 and 7 hr respectively on days −1 to +3 (volume 40 µl); placebo treated mice were similarly treated but with 40 µl PBS.

Blood samples from both groups and an untreated control group were taken by cardiac puncture at time 1 hr on days +1 to +15 under terminal halothane anaesthesia (n=4–5 per group per day). Blood samples were anticoagulated with EDTA, neutrophil and platelet counts were performed on a TECHICON™ H1 blood cell analyser (Bayer Diagnostics).

Figure 1:
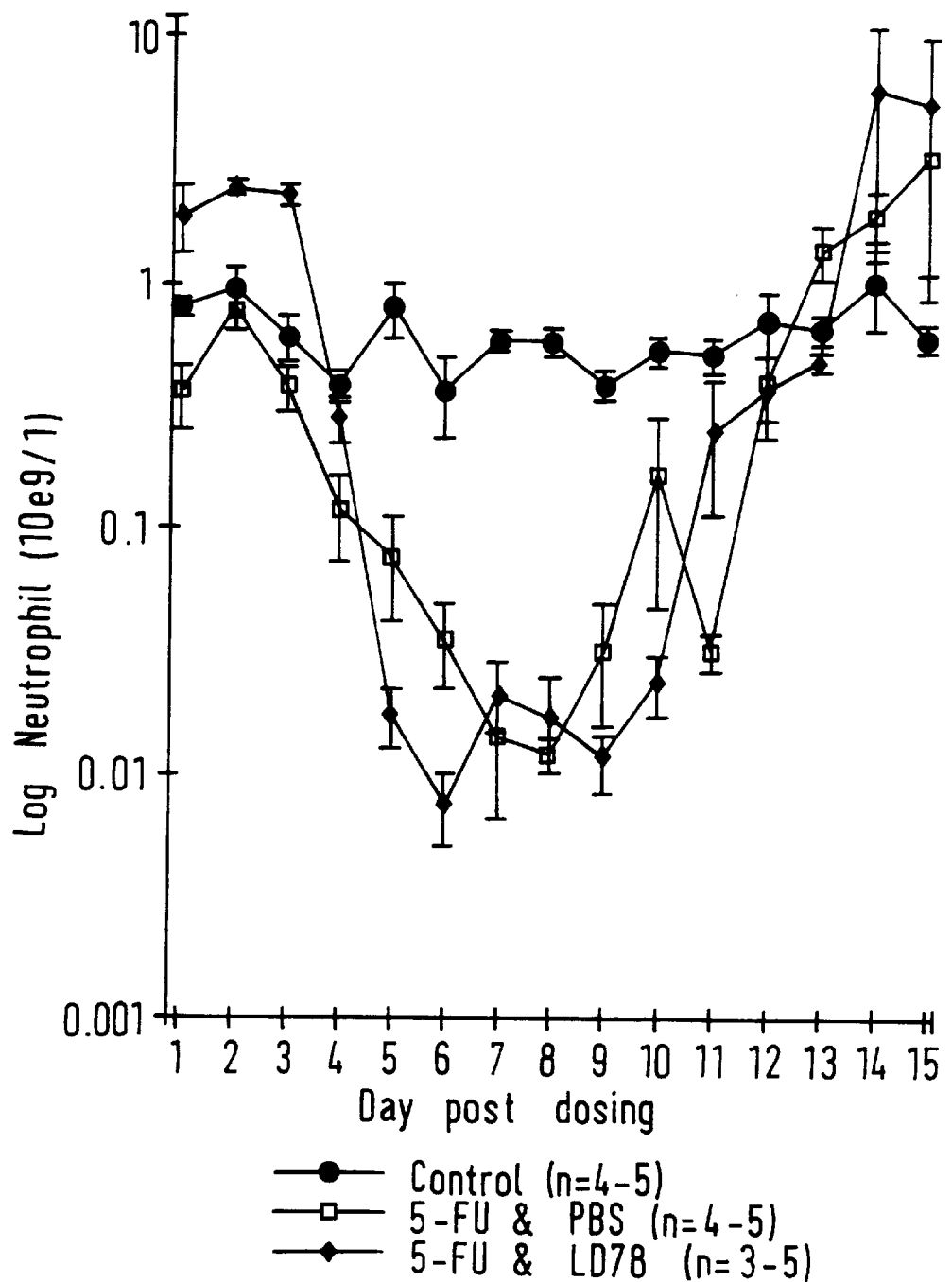
FIG. 1 is a graph showing the neutrophilic effect of L1D78 on 5-FU-treated mice.

Transient neutrophilia was unexpectedly detected in the LD78 treated group on days −2 to +3. The neutrophilia decayed to a 5-FU-induced neutropaenia similiar in depth and duration to the placebo treated group (FIG. 1).

EXAMPLE 2

Effect of LD78 on Neutrophil Recovery Kinetics in a Murine Ara-C Model of Neutropaenia A model of neutropaenia using cytosine arabinoside (Ara-C) was also investigated. This agent was used in the only reported study of the effect of LD78 on neutrophil recovery (Dunlop et al., Blood 79 2221–2225 (1992)). LD78 was dosed at 1 mg/kg and 3 mg/kg s.c. at 0 and 7 hr respectively on days −5 to +2 (volume 40 µl); placebo treated mice were dosed with 40 µl PBS. Ara-C 100 mg/kg i.p. was given to all mice at time-1 hr and 6 hr on days −5, −1 and 0.

For neutrophil and platelet counts, blood samples were taken from both groups and an untreated control group on days −4 to +10 by cardiac puncture at time 1 hr under terminal halothane anaesthesia (n=4–5 per group per day). Blood cell counts were analysed on a TECHNICON" H1 blood cell analyser (Bayer diagnostics).

Figure 2:
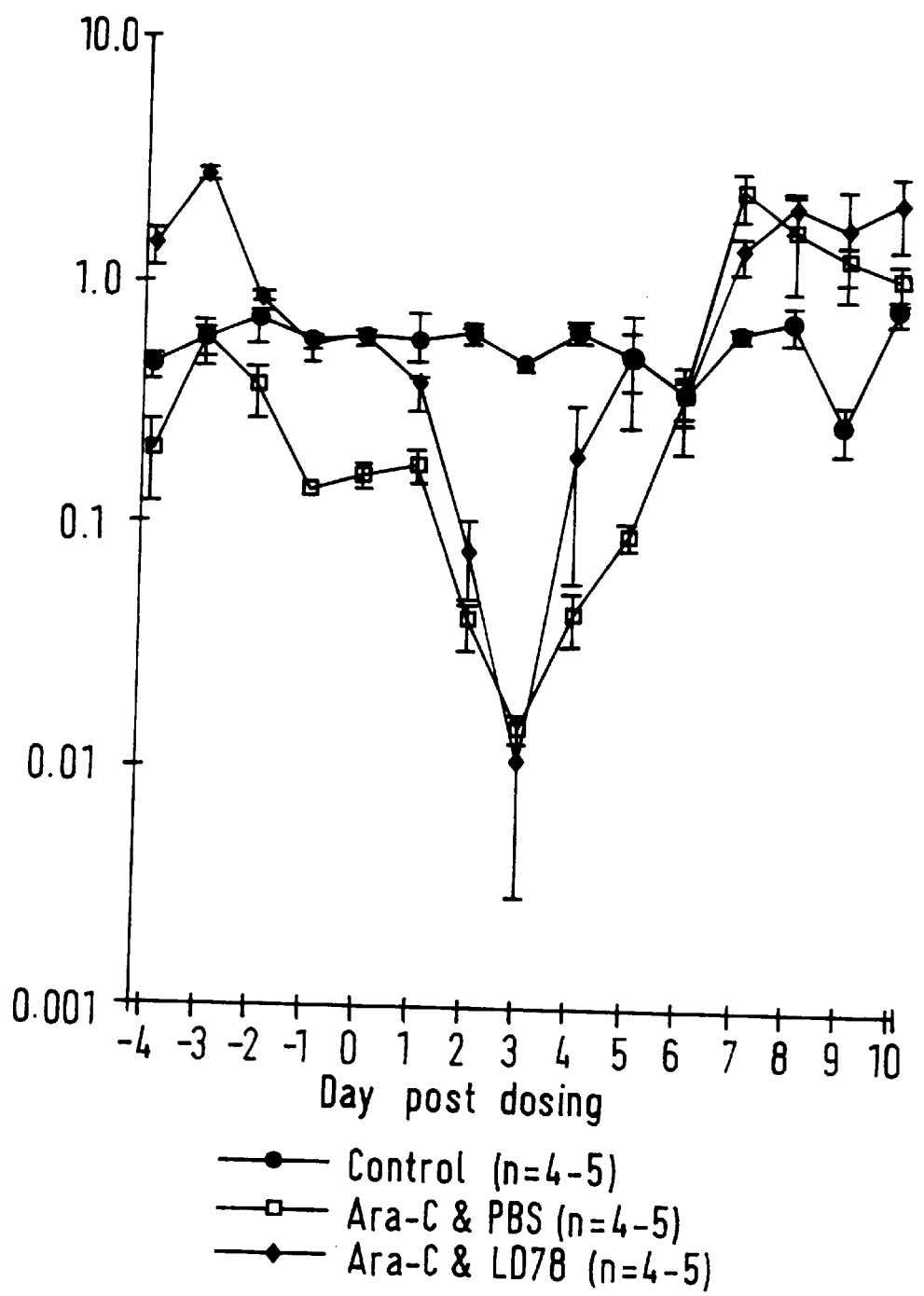
FIG. 2 is a graph showing the neutrophilic effect of LD78 on ara-C-treated mice.

A transient neutrophilia was again observed in the LD78 treated group on days −4 and −3. The neutrophilia was followed by a neutropaenia whose nadir was the same as the placebo treated group. Neutrophil recovery was faster in the LD78 treated group, with recovery seen on day +5 compared to day +7 in the placebo treated group (FIG. 2). LD78 could be detected in the samples at concentrations between 100–150ng/ml up to day 0, dropping to <500pg/ml on day +3, one day afer the last dose with LD78.

The LD78 treatment clearly enhanced neutrophil recovery, since the neutrophil count had returned to normal values on days +5 and +6 post dosing in the LD78-treated group, compared to day +7 in the placebo treated group. The maximum degree of neutropaenia was not affected. Overall, the duration of neutropaenia was reduced by 4 days in the LD78 treated group, although at least 2 days of is reduction can be accounted for by the acute neurophilic effects of the LD78 treatment.

Figure 3:
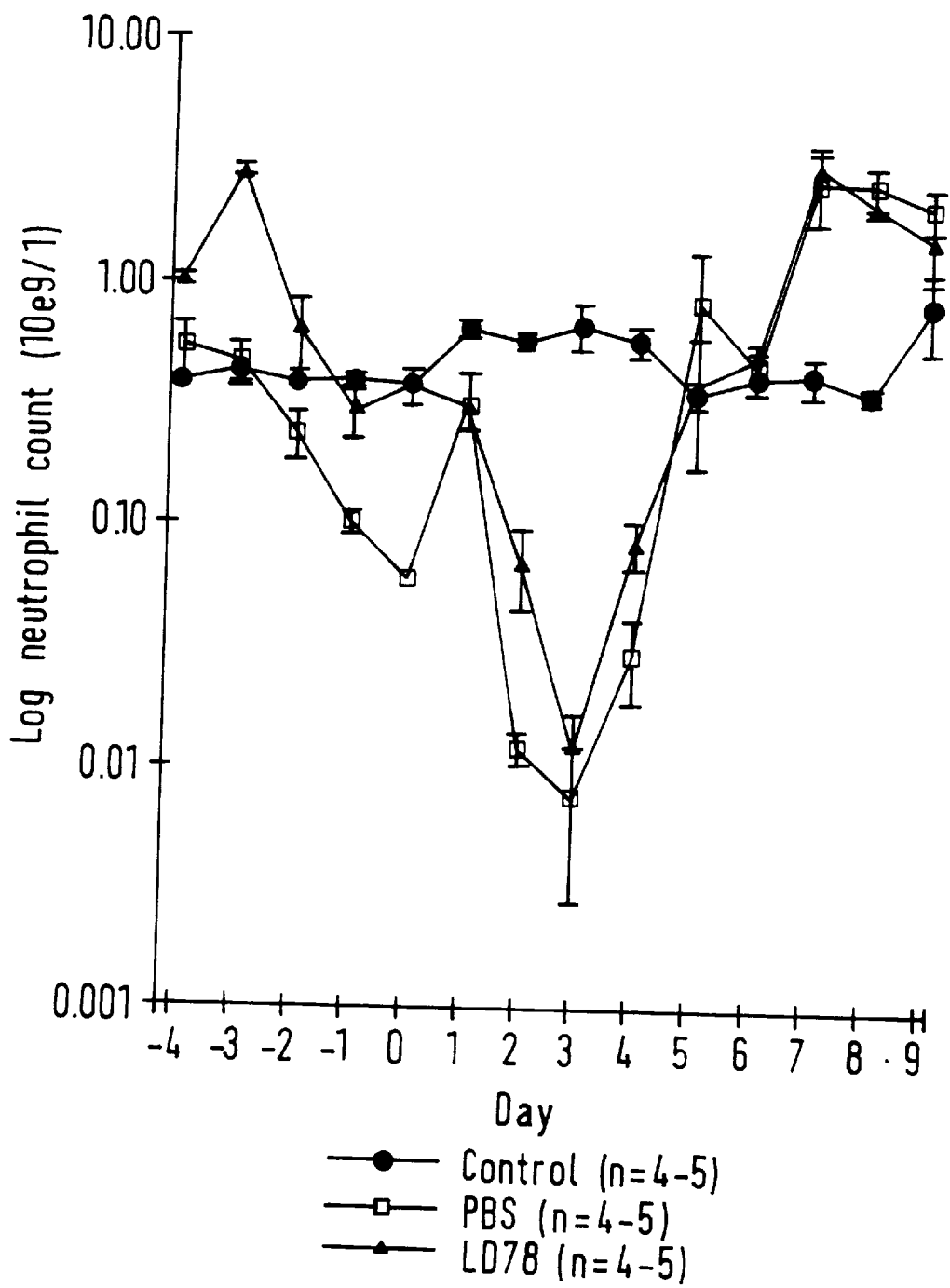
FIG. 3 is a further graph showing the neutrophilic effect of huMIP-1α (LD78) on ara-C-treated mice.

In a direct repeat of the above study, transient neutrophilia was also observed on days −4 and −3. However, the duration of the neutropaenia in the LD78 treated group and the placebo treated group were not significantly different in the second study. This result was due in part to the neutrophil count on day +5 of the placebo group which had recovered to control levels compared to day +7 in the first study (FIG. 3). The neutrophil recovery rate appears to be greater in the LD78 treated group.

Taken together, these two studies indicate that LD78 is having an effect on netrophil recovery rates. The observation that LD78 induces an acute neutrophilia was unexpected, and has provided a number of potential clinical indications for this molecule.

EXAMPLE 3

Neutrophilia Studies in BALB/c Mice by Subcutaneous Injection

In order to investigate further the acute neutrophilia described above, the effect of LD78 as set forth in SEQ ID NO.2 was compared with that obtained using two LD78 variants or mutants. Mutant #10 carries a single Asp26>Ala substitution which discourages the molecule from associating beyond a tetramer and may be designated LD78 (Asp26>Ala). Mutant #26 carries a single substitution (Phe12>Glu) and forms a homogeneous population of dimers; it may be designated LD78(Phe12>Glu). The biological properties of Mutant #10 are essentially wildtype with respect to receptor binding and its ability to induce $Ca^{2+}$ responses in THP-1 cells. Mutant #26, in contrast, is essentially inactive and was included as a control.

BALB/c mice were dosed with either LD78 at 1, 10, 30, 100 and 1,000 µg/kg s.c.; mutant #10 at 1, 10 and 30 µg/kg s.c.; or mutant #26 at 30, 100 and 1000 µg/kg s.c. (all 40 µl volume in PBS). Blood samples were taken at 30 min post-dosing by cardiac puncture under terminal halothane anaesthesia. Blood samples were anticoagulated with EDTA and neutrophil counts were performed using a TECHNICON" H1 blood counter (Bayer).

Figure 4:
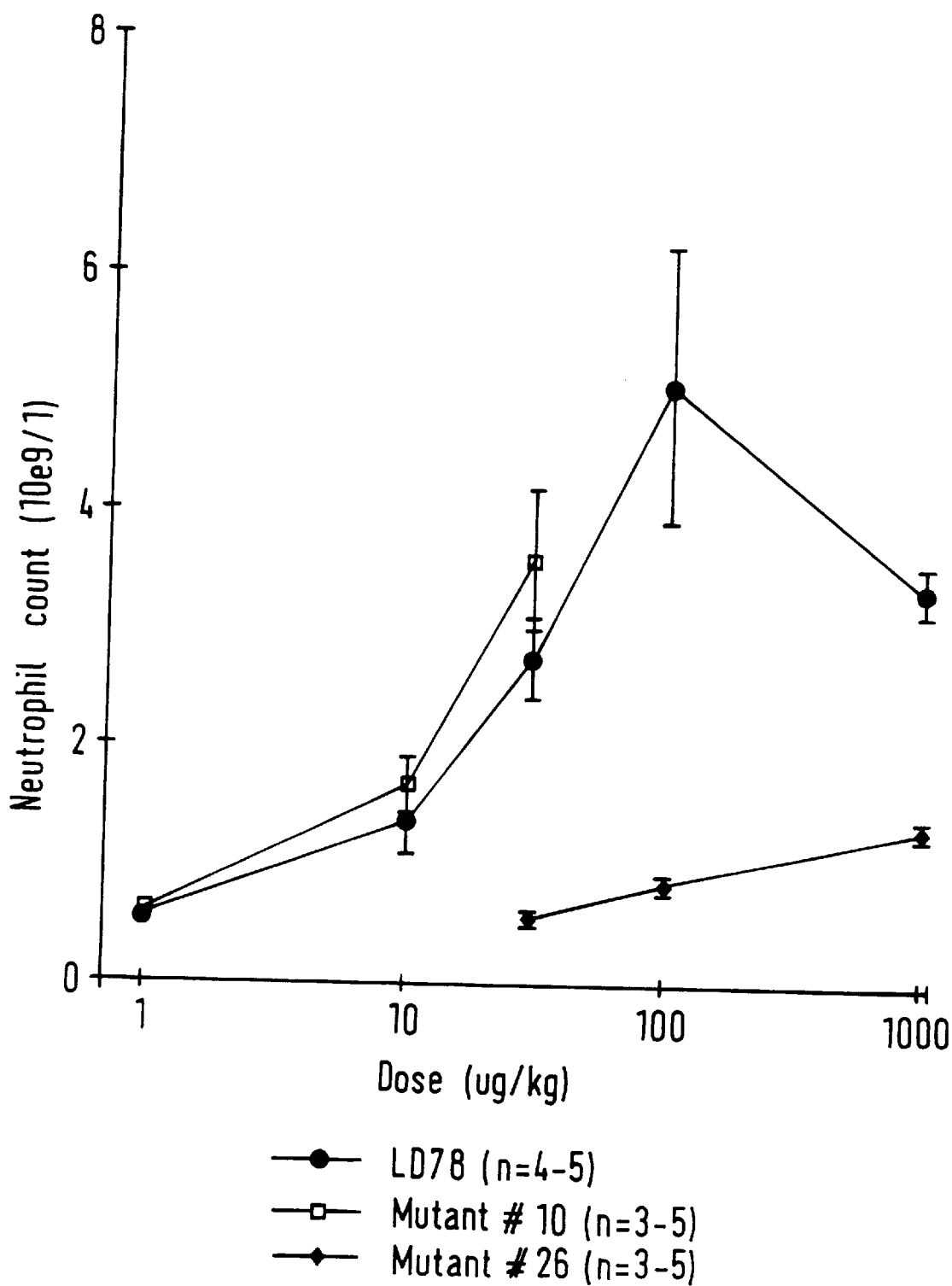
FIG. 4 shows the neutrophilic effect of LD78 and mutant #10 (LD78) (Asp26>Ala)) SEQ ID NO.2.
Figure 5:
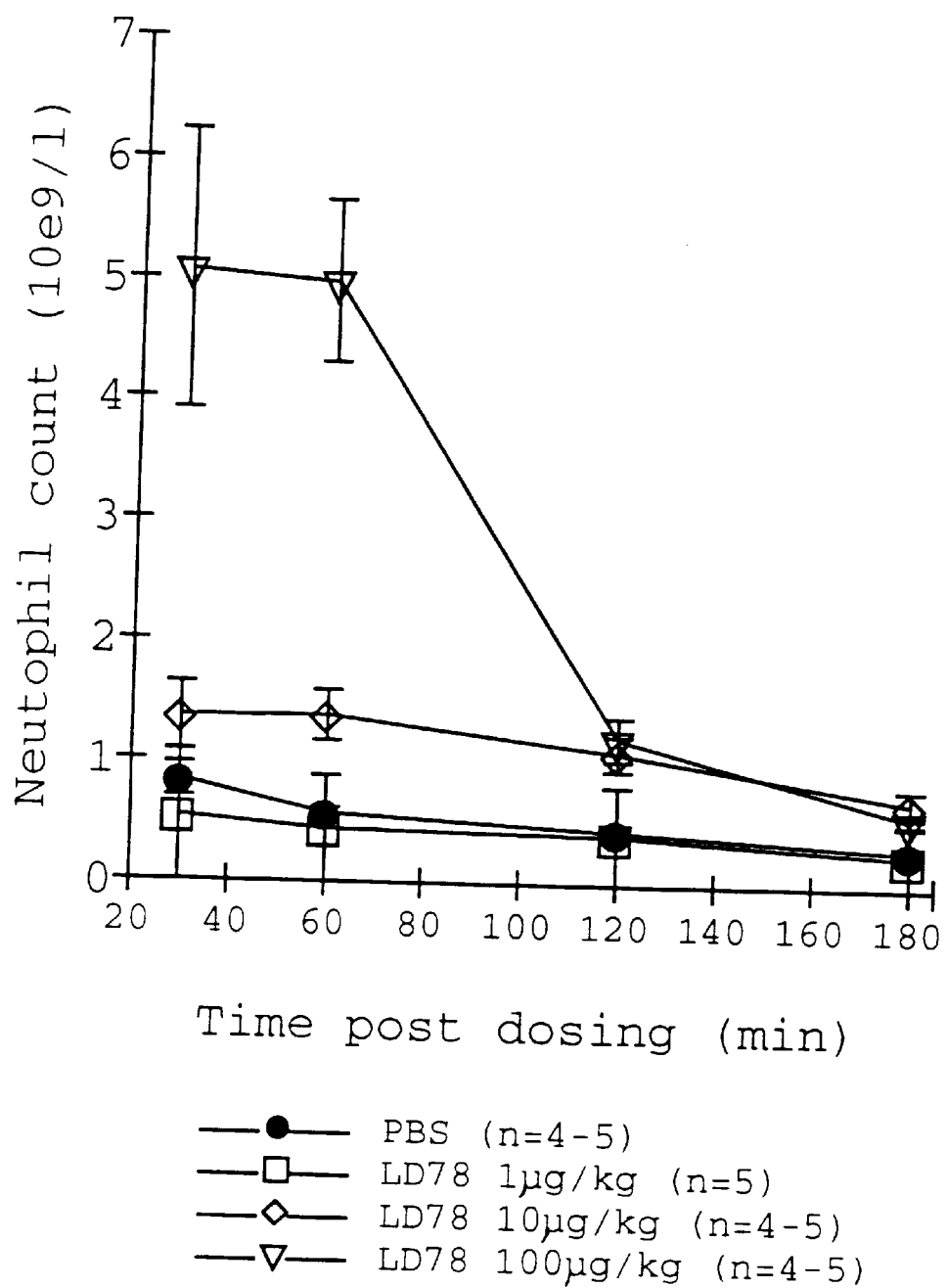
FIG. 5 shows the neutrophilic effect of different s.c. doses of LD78.
Figure 6:
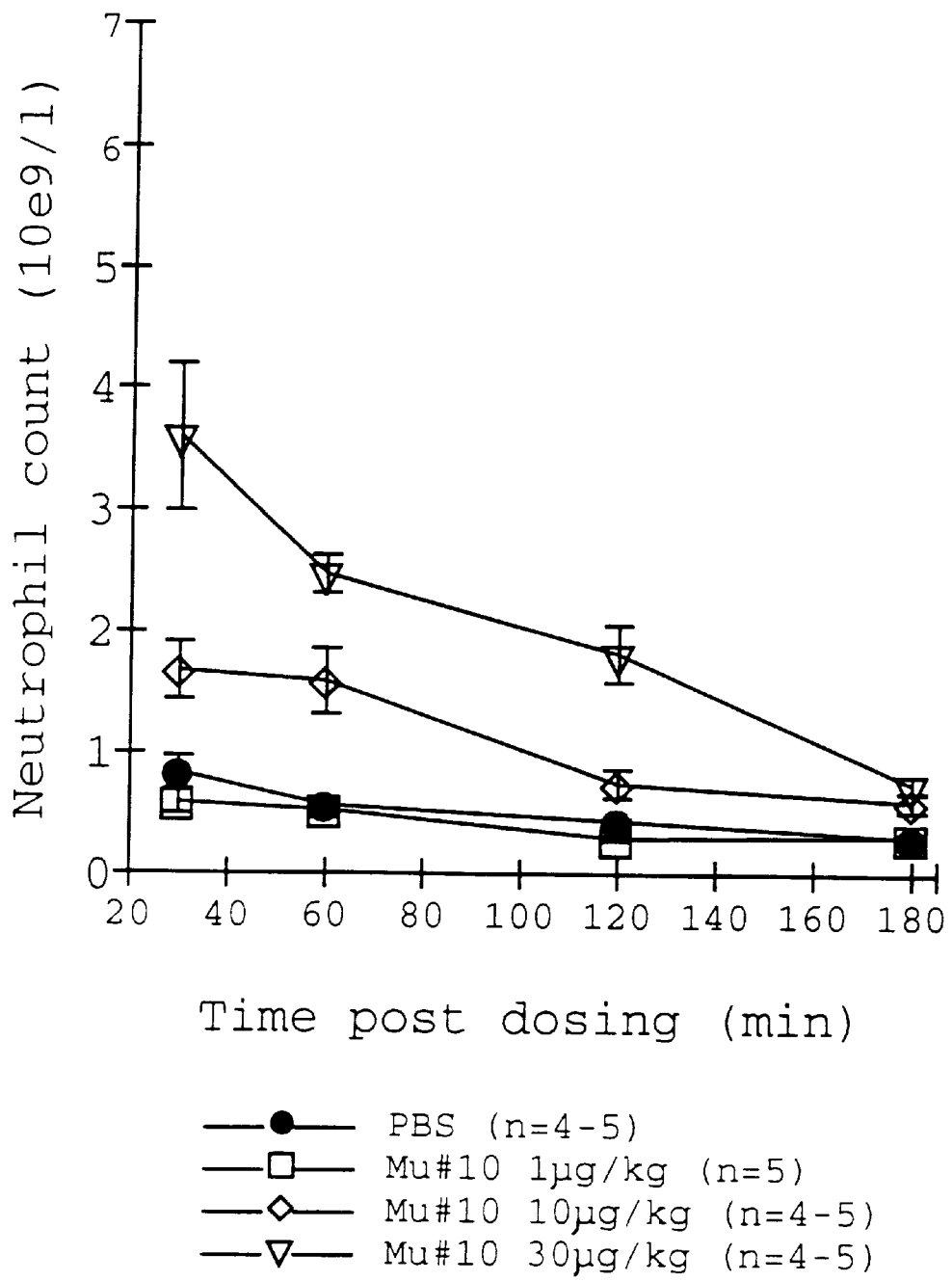
FIG. 6 shows the neutrophilic effect of different s.c. doses of mutant #10 (LD78(Asp26>Ala)) SEQ ID NO.2.

A dose-dependent increase of neutrophil counts was seen in LD78 treated animals with doses up to 100 µg/kg; no further increase was seen at 1,000 µg/kg. Mutant #10 at the doses tested showed similiar increases in neutrophil counts to LD78. However, mutant #26 showed only marginal increases in neutrophil counts post-dosing at 1,000 µg/kg (FIG. 4). The time course of the neutrophil count post-dosing at various levels s.c. is shown for LD78 in FIG. 5 and for mutant #10 in FIG. 6.

EXAMPLE 4

Neutrophilia Studies in BALB/c Mice by Intravenous Injection

Figure 7:
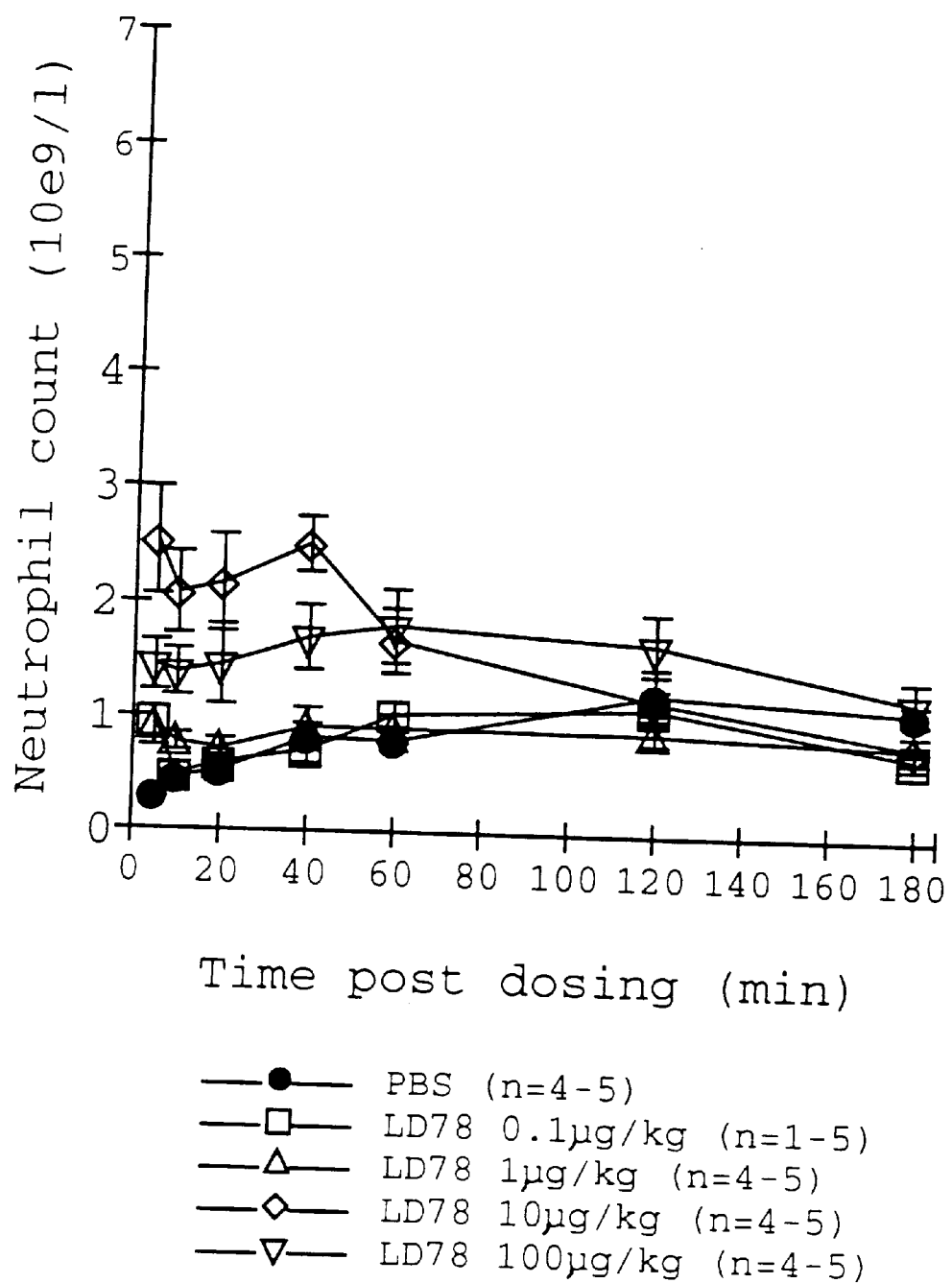
FIG. 7 shows the neutrophilic effect of different i.v. doses of LD78.
Figure 8:
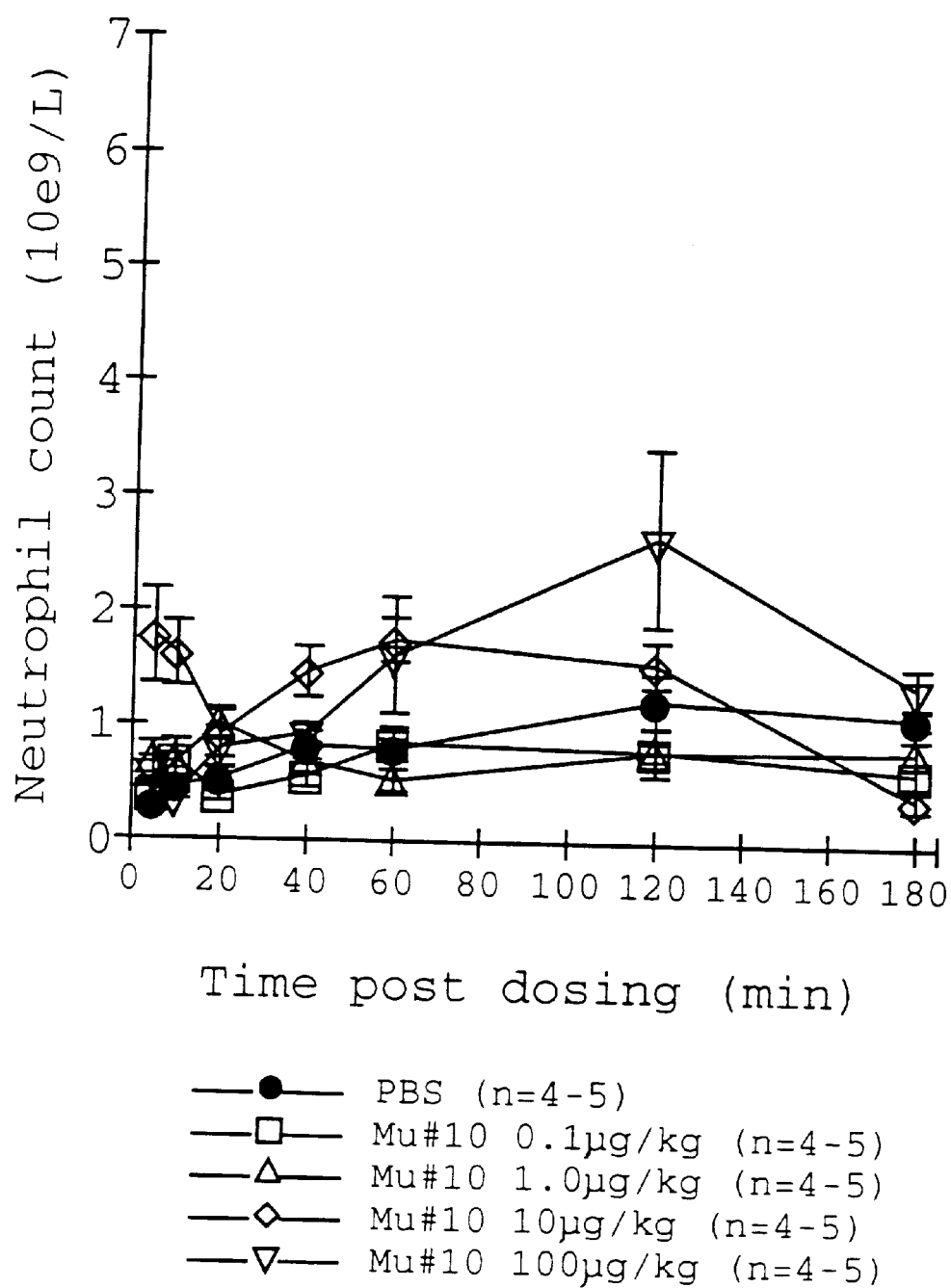
FIG. 8 shows the neutrophilic effect of different i.v. doses of mutant #10 (LD78(Asp26>Ala)) SEQ ID NO.2.
Figure 9:
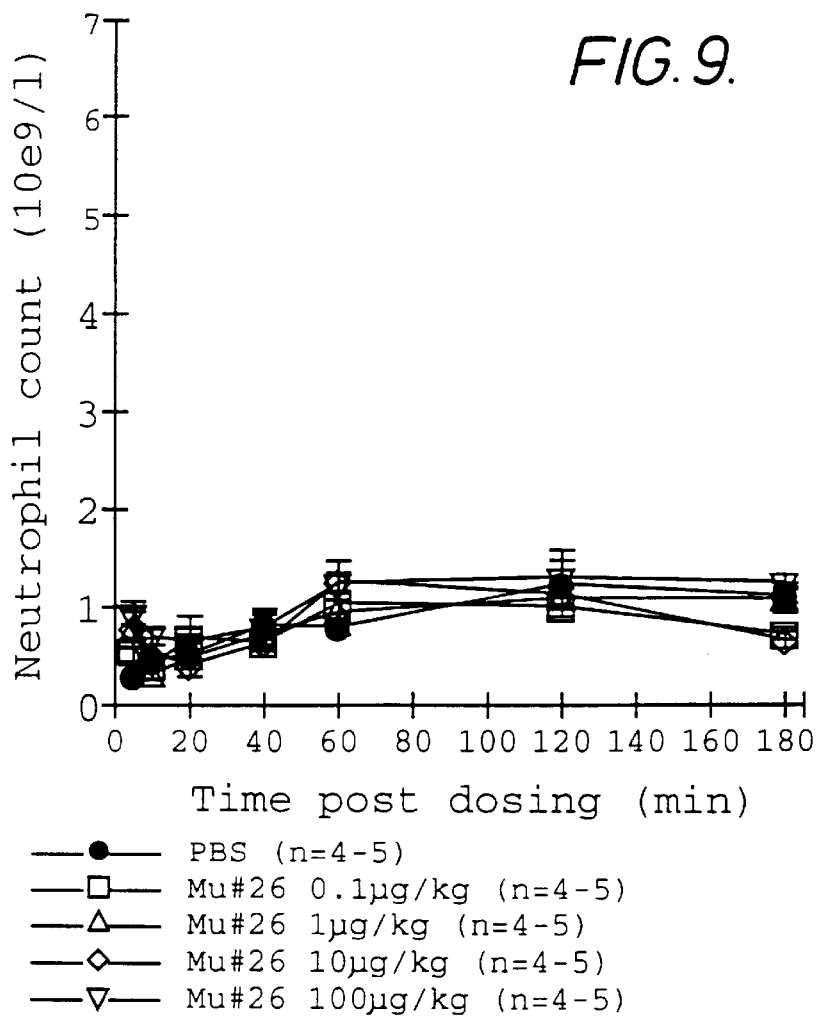
FIG. 9 shows theneutrophilic effect of different i.v. doses of mut #26 (LD78(Phe12>Glu)) SEQ ID NO.2.

The procedure of Example 3 was repeated, except that the active compound was administered i.v. rather than s.c. Effects on neutrophil count were again seen, but less marked than for the s.c. administration of Example 3. The time course of the neutrophil count post-dosing at various levels i.v. is shown for LD78 in FIG. 7, for mutant #10 in FIG. 8 and for mutant #26 in FIG. 9.

EXAMPLE 5

Adjuvant Properties of SCIs

The effects of murine MIP-1α on cyctotoxic T lymphocyte (CTL) induction by hybrid Ty-VLPs were examined. Hybrid Ty-VLPs are virus-like particles which comprise an antigenic sequence fused to the C-terminus of the self assembling p1 protein derived from the yeast retrotransposon. Hybrid Ty-VLPs are produced in yeast. Hybrid Ty-VLPs carrying 40 amino acids of the influenza virus nucleoprotein were prepared as previously described in WO-A-9320840. BALB/c mice were immunised intramuscularly with 20 µg flu NP-VLPs with either 250, 25, 2.5 or 0 ng of SCP. 12 days later the spleens were removed and spenocytes restimulated with influenza peptide for 7 days. The cells were then assayed for CTL activity. FIG. 42 shows that SCP at 2.5 ng enhanced CTL levels, assessed by killing of flu NP peptide. The data represent the mean of 32 mice/group. BALB/c mice were also immunised with 1 µg hybrid VLPs carrying a 9 amino acid sequence of the malaria circumsporozoite (CSP) protein with either 250, 25, 2.5 or 0 ng of SCP. Spleens were removed 3 days later and the splenocytes were restimulated for 7 days with a malaria CSP peptide (9 amino acids). The cells were then assayed for CTL activity against malaria CSP peptide-pulsed P815 target cells ($^{51}Cr$ labelled). FIG. 43 shows that all three dose levels of SCP enhanced malaria-specific CTL activity. The data represent 3 mice/group.

EXAMPLE 6

Wild-type LD78 is not Pyrogenic

Recombinant wild-type LD78 was tested for pyrogenicity in rabbits by the European Pharmacopoeia pyrogen test V.2.1.4 (1986). Rabbits were dosed with a 5 mg/ml formulation at 2 ml/kg bodyweight. The mean±SD temperature increase was 0.38° C.±0.024° C. (n=3), from which result the European Pharmacopoeia defines the product as being non-pyrogenic.

EXAMPLE 7

$Ca^{2+}$ Efflux in THP-p1 cells

THP-1 cells at a density of 2 to 3×10⁶ cells/ml were loaded with FURA-2AM™. Cells in logarithmic growth were washed in medium and incubated in the presence of 1 µM FURA-2AM™ at 37° C. for 45 minutes. The cells were washed in Tyrodes buffer to remove excess FURA-2AM . Finally the cells were resuspended in Tyrodes buffer to 2–3×10⁶ cells/ml and the tube wrapped in foil to prevent light bleaching the dye. All experiments were performed within 90 minutes of labelling the cells.

The cells were mixed with $Ca^{2+}$ (final concentration 1 mM) and placed into a PERKIN-ELMER™ LS-50 fluormeter. Wild-type LD78, variant 10 or variant 26 were added (1 µg/ml) and the increase of fluorescence intensity was measured under the following conditions:

$\lambda_{ex}$=340nm, 10 nm bandwidth; $\lambda_{em}$=500nm, 10 nm bandwidth;

1 cm pathlength cell; thermostatted cell holder at 37° C.

Figure 10A:
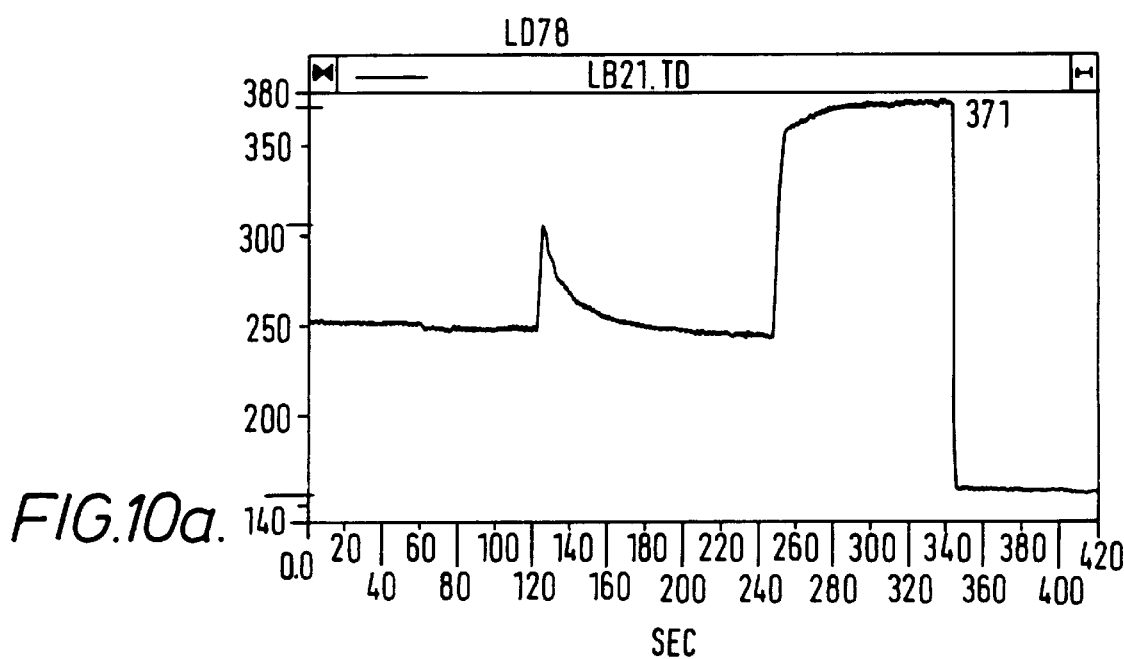
FIGS. 10a, 10b and 10c show the effect of D78, mutant #10 (LD78(Asp26>Ala)) and mutant #26 (LD78 (Phe12>Glu)), respectively SEQ ID NO.2, on calciumn efflux.
Figure 10B:
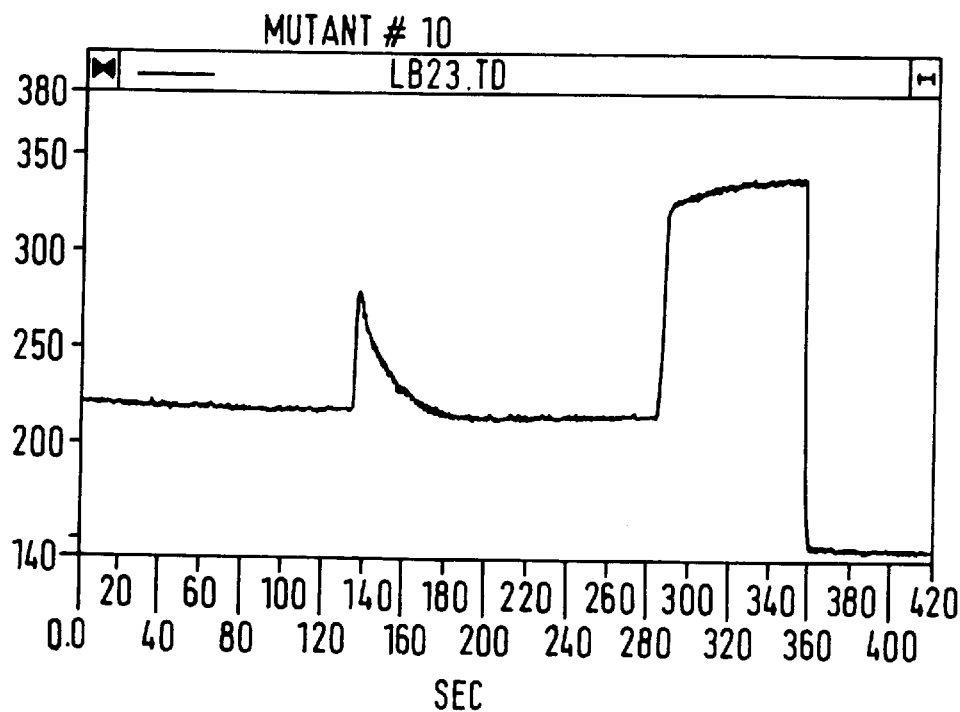
Figure 10C:
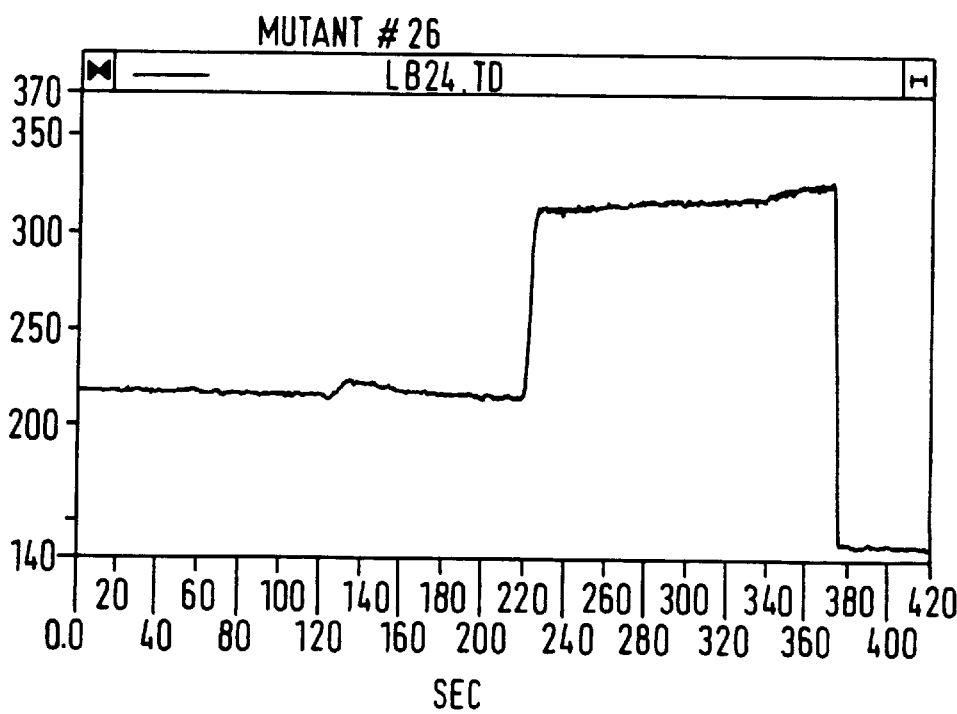
Figure 20:
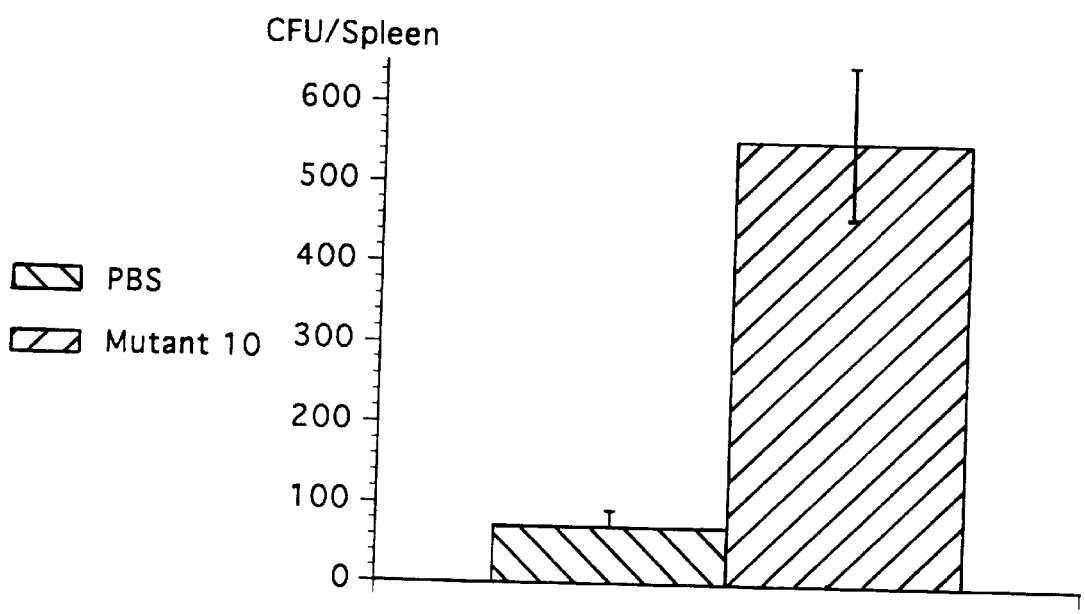
FIG. 20 shows the mobilisation of multipotent haematopoietic progenitor to spleens by mutant 10.

The result is shown in FIG. 20. Estimates of the maximum and minimum fluorescence intensities were made by the addition of digitonin and EGTA, respectively, and are also shown in FIG. 10.

EXAMPLE 8

Neutrophilia Studies in Marmosets by Subcutaneous Infection

Figure 11:
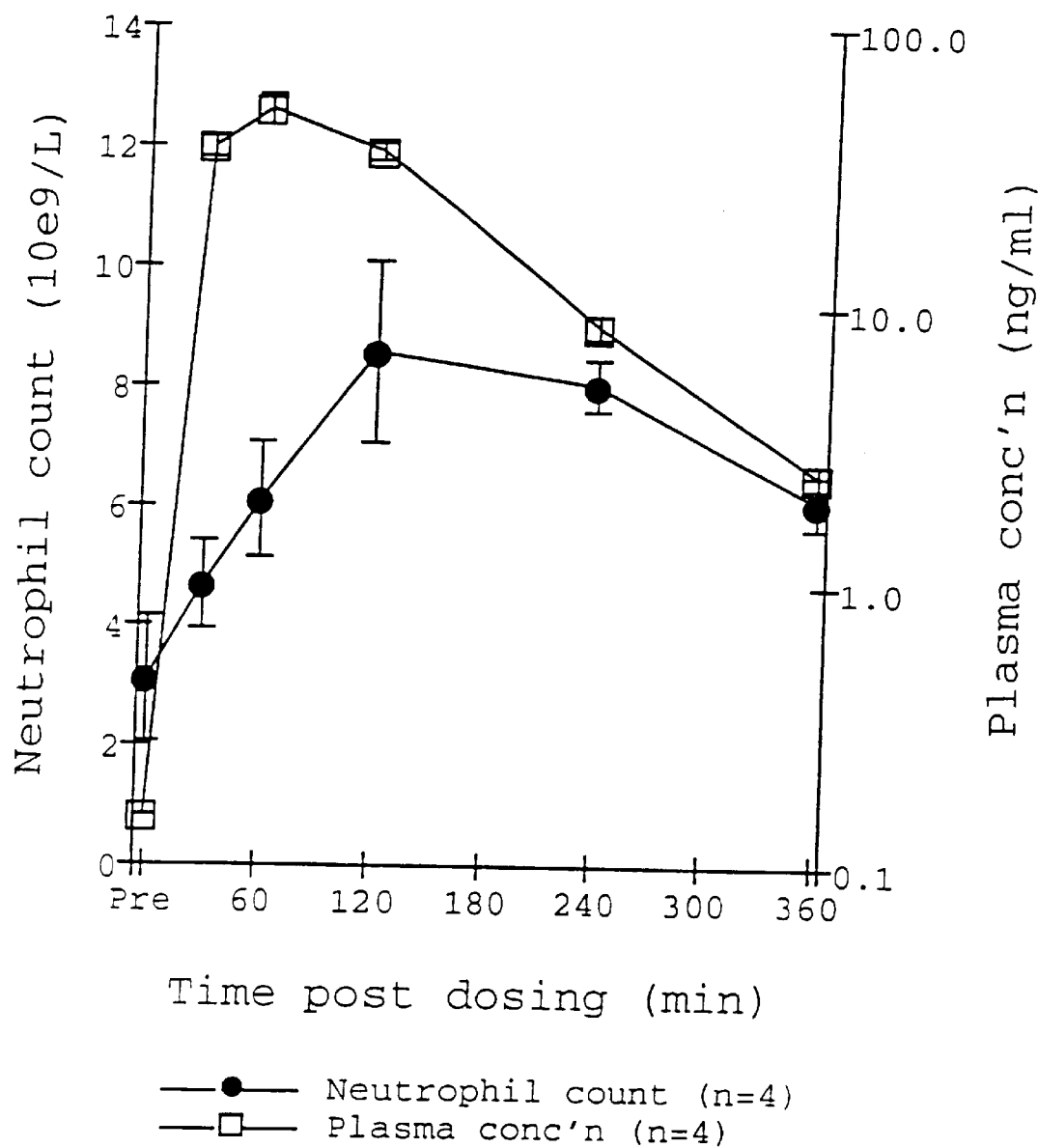
FIG. 11 shows the time course of the neutrophil count post-dosing at various levels s.c. in marmosets.

Marmosets were dosed with mutant #10 at 100 µg/kg s.c. (all 40 µl volume in PBS). Blood samples were taken at and anticoagulated with EDTA and neutrophil counts were performed using a TECHNICON™ H1 blood cell counter (Bayer). The time course of the neutrophil count post-dosing at various levels s.c. is shown in FIG. 11.

EXAMPLE 9

Neutrophilia Studies in Marmosets by Intramuscular Injection

Figure 12:
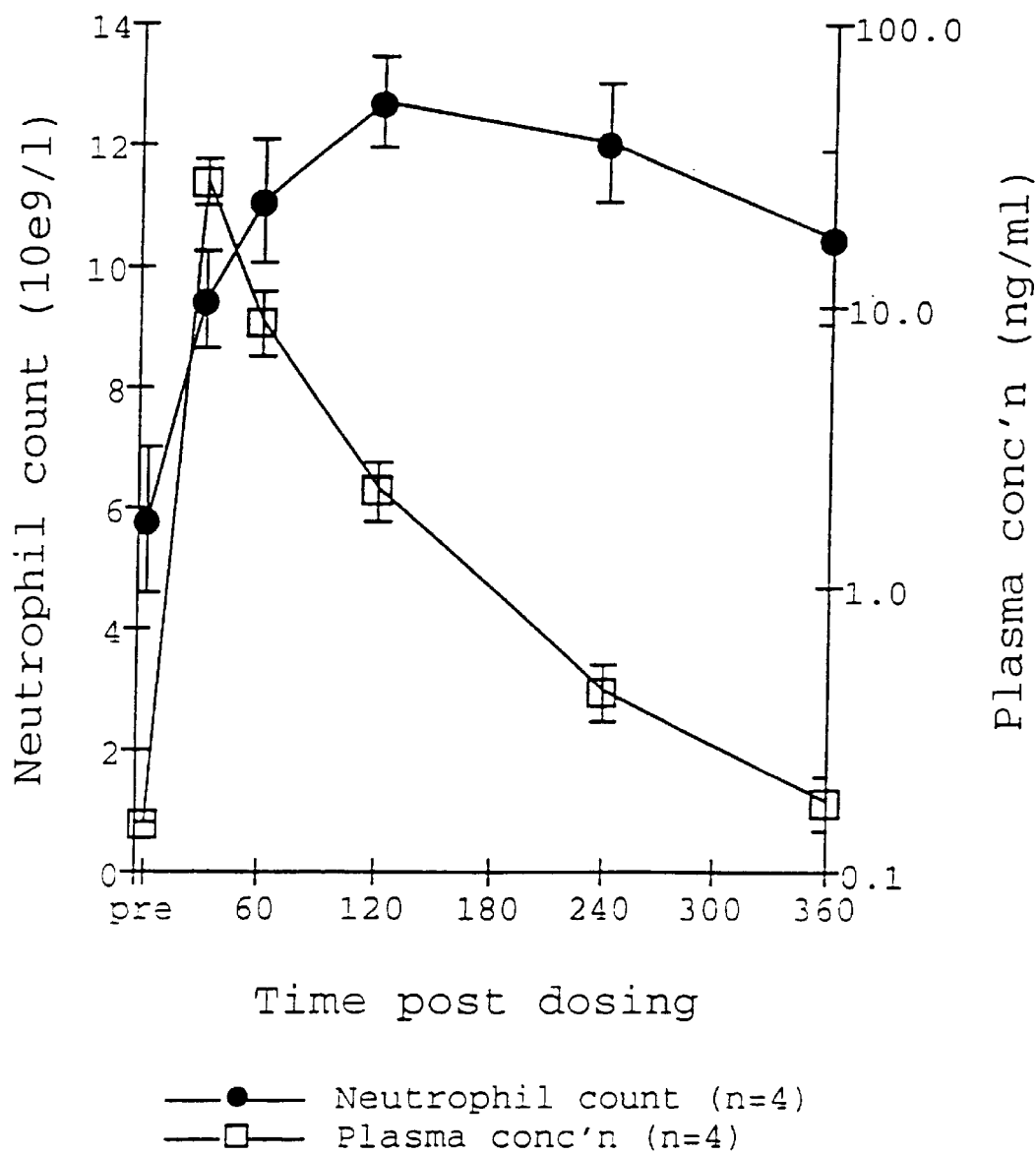
FIG. 12 shows the time course of the neutrophil count post-dosing at various levels i.v. in marmosets.

The procedure of Example 8 was repeated, except that the active compound was administered i.m. rather than s.c. Effects on neutrophil count were again seen. The time course of the neutrophil count post-dosing i.m. is shown for mutant #10 in FIG. 12.

EXAMPLE 10

Mobilisation of Early Progenitor Cells by Mutant #10

Mice were injected s.c. with either 2.5 µg or 10 µg of the tetrameric SCI variant mutant #10. At times 0.5, 1, 2 and 24 hours after injection, groups of three mice were killed and their blood analysed for circulating leukocytes and CFU-S.

Stem cell numbers were measured by injecting blood from test mice into lethally irradiated indicator mice. Stem cells that lodge in the spleen of the recipient mice multiply to give large mixed colonies of haematopoietic cells that form nodules which can be counted after 8–11 days. The number of stem cells in the peripheral blood of the donor mice can be inferred by working back from the number of CFU-S colonies, taking account any dilutions necessary to bring the CFU-s count within an interpretable range (3–30 colonies/spleen).

CFU-S counts were determined in recipient mice that had received lethal doses of γ-irradiation (15.2 Gy $^{60}$Co at 0.84 Gy/h). Spleens were collected after 8 days, preserved in formalin and the colonies were counted to give 8-day CFU-S counts. Appropriate volumes of blood were injected intravenously into 10 recipient mice. CFU-S counts are expressed as the mean number of CFU-S forming cells/ml of bloods, ±standard error. Total leukocyte counts were determined in parallel using a haemocytometer.

Figure 13A:
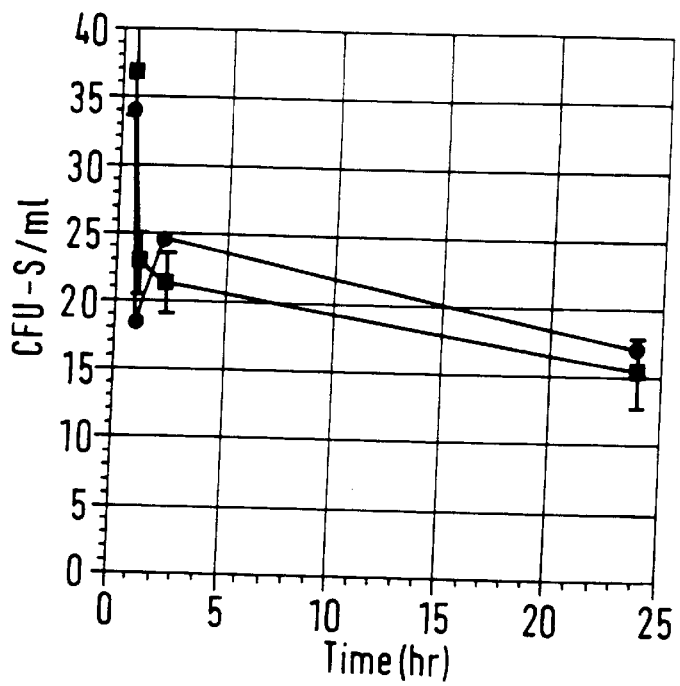
FIG. 13a and 13b show the time course for mobilisation of perpheral CFU-S count and leukocytes, respectively.
Figure 13B:
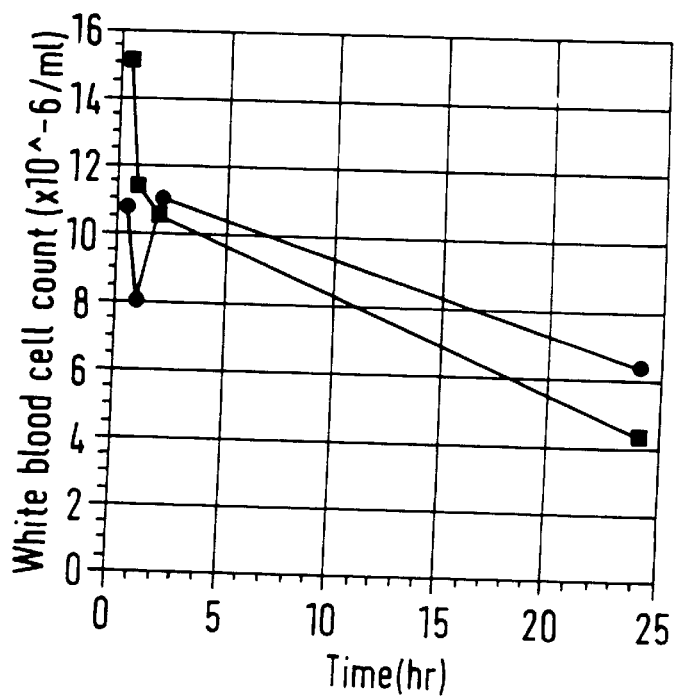

This experiment revealed the expected neutrophila at 30 minutes after administration of mutant #10 at both doses studied. This decayed over 2 hours and leukocyte counts had returned to baseline by 24 hours. This pattern of leukocyte mobilisation was matched by an increase in peripheral CFU-S count from an expected value of 15–20/ml to 35–40/ml, 30 minutes after the administration of munt #10. This also returned to baseline afer 24 hours. The time course for peripheral CFU-S count is shown in FIG. 13.

This experiment shows that mutant #10 is capable of mobilising early progenitors as well as mature leukocytes from the marrow.

EXAMPLE 11

Effect of Co-administration of SCIs and G-CSF on Mature Haematopoietic Cells

Four dosing groups for each strain of mice were employed.
1) PBS Alone

Mice were dosed with PBS 40 µl s.c. between the scapulae. Blood samples were taken 30 minutes later by cardiac puncture from mice under terminal halothane anaesthesia. Blood samples were immediately anticoagulated with EDTA in 0.5 ml sample cups. Differential white blood cells counts were performed on a Technicon H1 blood cell counter with FDA approved software.

2) Mutant #10 Alone

Mice were dosed with mutant #10 100 µg/kg s.c. in PBS (injection vol 40 µl) between the scapulae. Blood samples were taken 30 minutes later and analysed as described.

3) G-CSF and PBS

Mice were dosed with G-CSF, 100 µg/kg s.c. diluted appropriately in PBS (injection vol. 40 µl) b.i.d. at 0 and 7 hour on days 0 and 1. On day 2 mice received PBS 40 µl s.c. and blood samples were taken 30 minutes later and analysed as described.

4) G-CSF and Mutant #10

Mice were dosed with G-CSF, 100 µg/kg s.c. diluted appropriately in PBS (injection vol. 40 µl) b.i.d. at 0 and 7 hour on days 0 and 1. On day 2 mice received mutant #10 100 µg/kg s.c. and blood samples were taken 30 minutes later and analysed as previously described.

Figure 14:
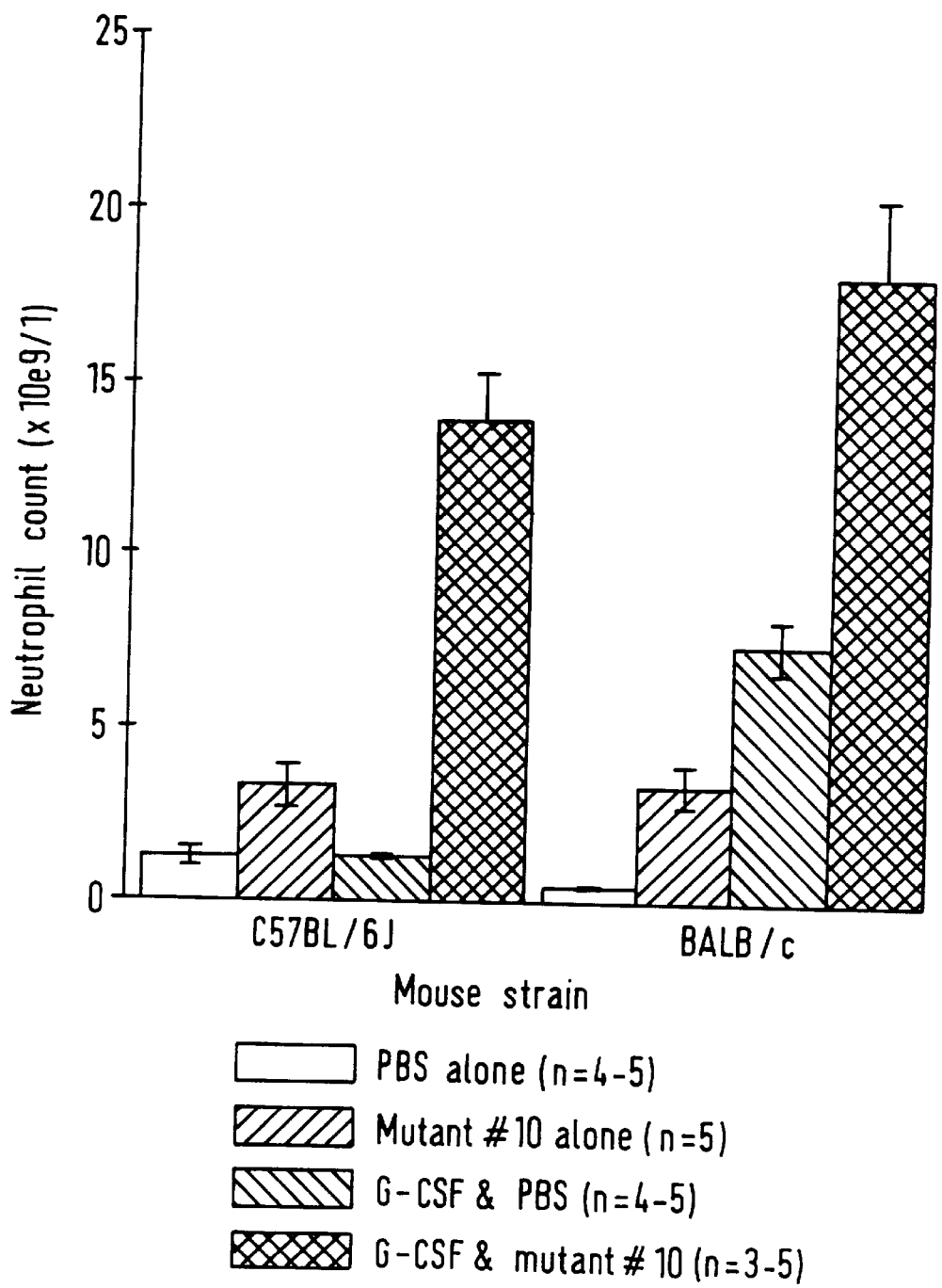
FIG. 14 shows the effects of G-CFS co-administered with mutant #10 (LD78) (Asp26>Ala)) SEQ ID NO.2 on mouse neutrophil count.

(a) Neutrophil count: The effects on neutrophil count are shown in FIG. 14.

In C57BL/6J mice mutant #10 alone caused a 2.6-fold increase in circulating neutrophil count compared to PBS alone, G-CSF and PBS caused no increase in neutrophil count compared to PBS alone. However, G-CSF and mutant #10 caused a 10.9-fold increase in neutrophil count compared to PBS alone. In BALB/c mice mutant #10 alone caused a 7.4-fold increase in circulating neutrophil count compared to PBS alone, G-CSF and PBS treatment caused a 16.1-fold increase and G-CSF and mutant #10 caused a 39.5-fold increase in neutrophil count compared to PBS alone.

Figure 15:
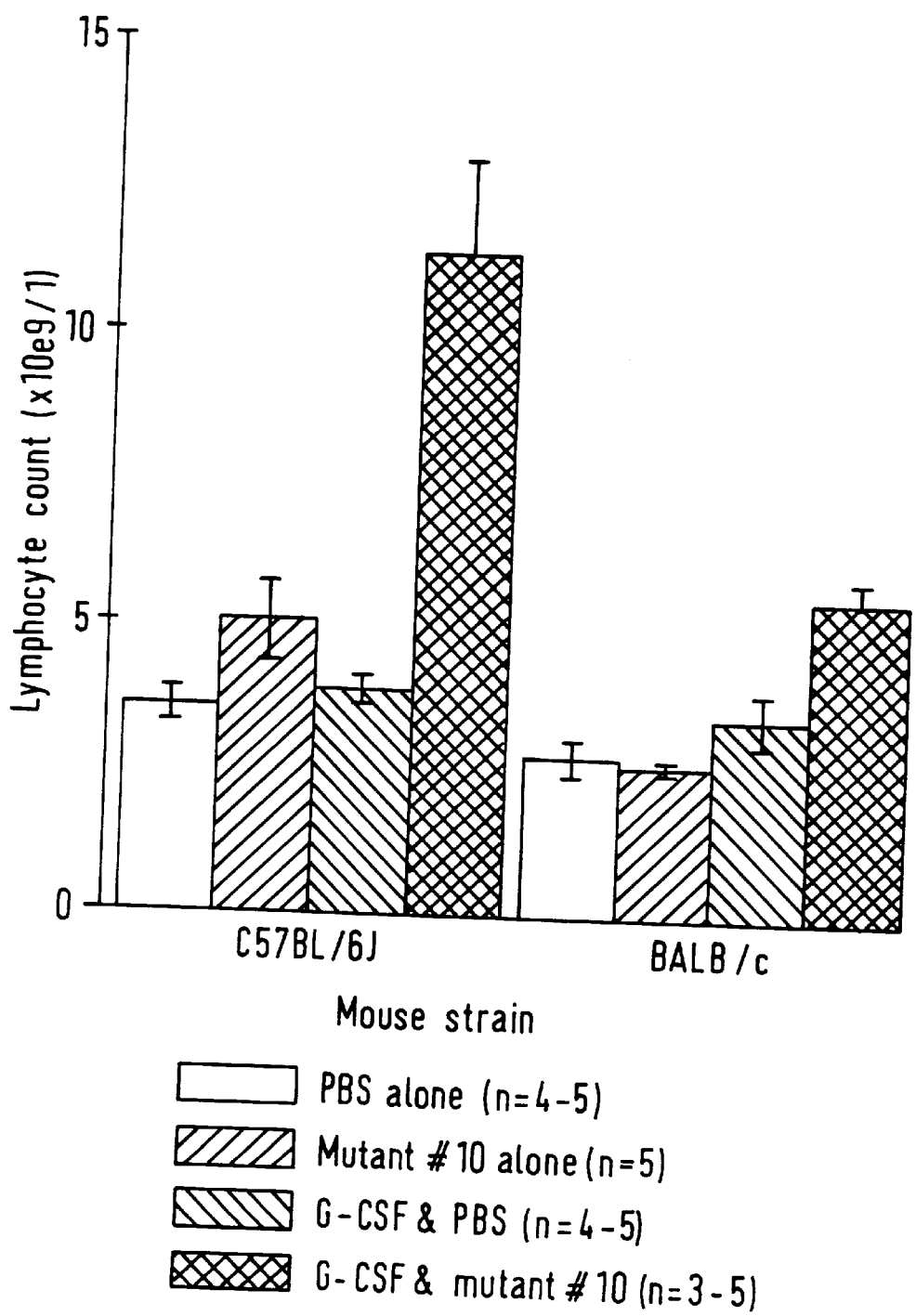
FIG. 15 shows the effects of G-CSF co-administered with mutant #10 (LD78) (Asp26>Ala)) SEQ ID NO.2 on mouse lymphocyte count.

(b) Lymphocyte count: The effects on lymphocyte count are shown in FIG. 15.

In C57BL/6J mice neither mutant #10 alone or G-CSF and PBS treatment groups caused an increase in circulating lymphocyte count, however G-CSF and mutant #10 caused a 3.2-fold increase in circulating lymphocyte count compared to PBS alone. In BALB/c mice neither mutant #10 alone or G-CSF and PBS treatment groups caused any increase in circulating lymphocyte count. However, G-CSF and mutant #10 treatment caused a 2-fold increase in circulating lymphocyte count compared to PBS alone.

Figure 16:
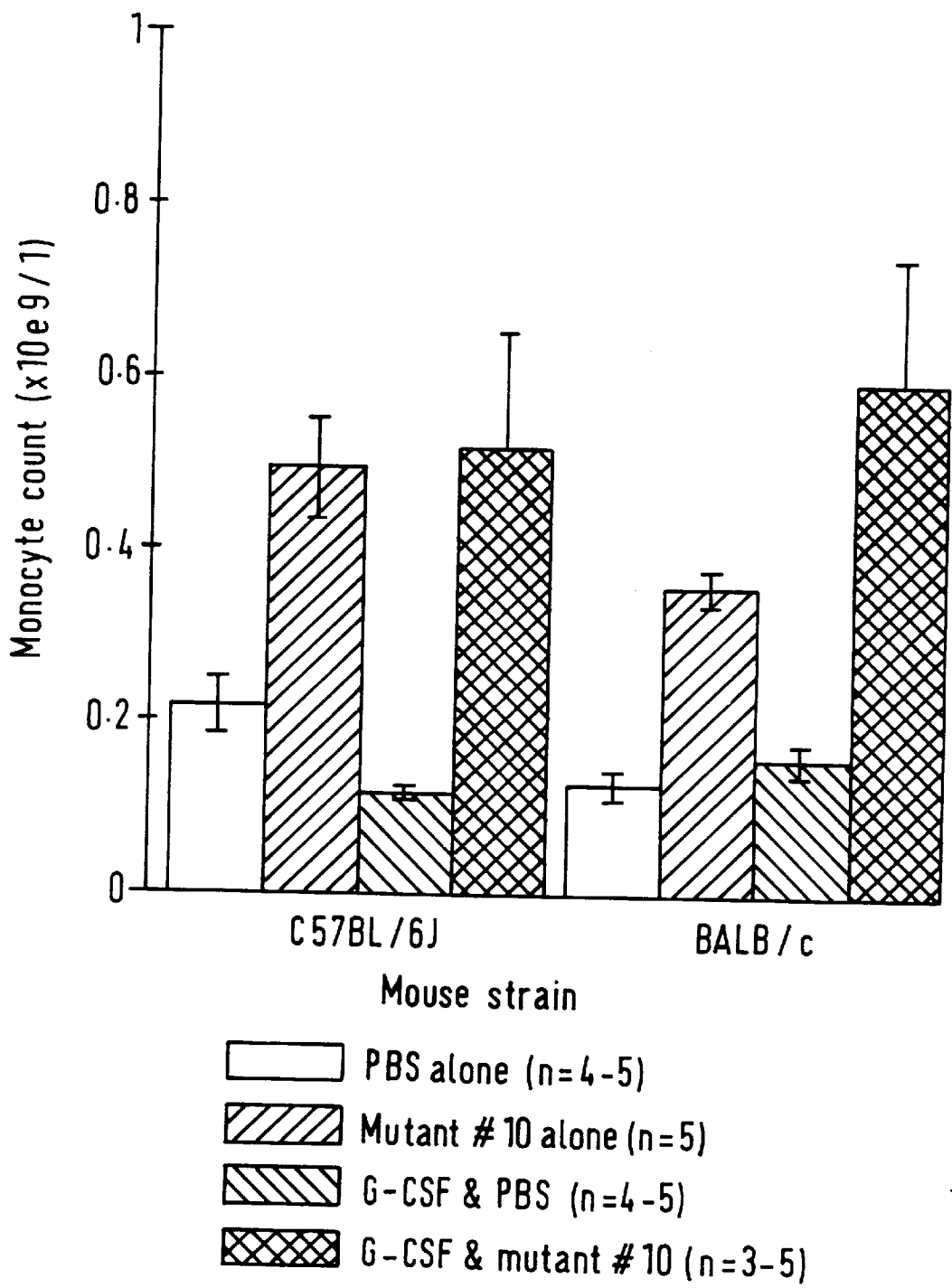
FIG. 16 shows the effects of G-CSF co-administered with mutant #10 (LD78) (Asp26>Ala)) SEQ ID NO.2 on mouse monocyte count.

(c) Monocyte count: The effects on monocyte count are shown in FIG. 16.

In C57BL/6J mice mutant #10 alone caused a 2.3-fold increase in circulating monocyte count compared to PBS alone. G-CSF and PBS caused no increase, with G-CSF and mutant #10 treatment causing a similar increase in monocyte count compared to mutant #10 alone. In BALB/c mice mutant #10 alone caused a 2.9-fold increase in circulating monocyte count compared to PBS. G-CSF and PBS caused no increase, with G-CSF and mutant #10 causing a similiar increase in monocyte count as mutant #10 alone.

Figure 17:
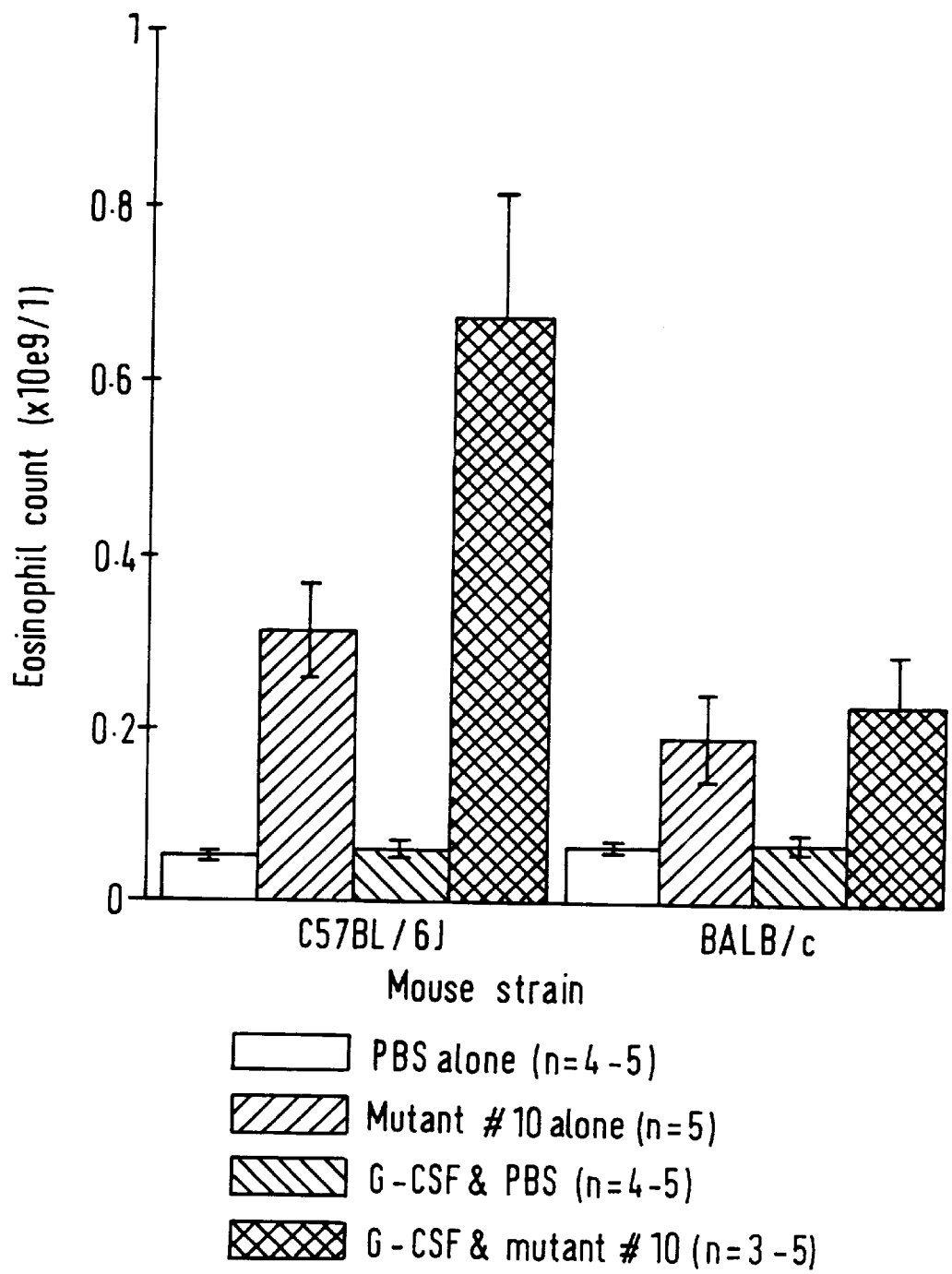
FIG. 17 shows the effects of G-CSF co-administered with mutant #10 (LD78) (Asp26>Ala)) SEQ ID NO.2 on mouse eosinophil count.

(d) Eosinophil count: The effects on eosinophil count are shown in FIG. 17. In C57BL/6J mice mutant #10 alone caused a 6-fold increase in circulating eosinophil count compared to PBS alone. G-CSF and PBS caused no increase, with G-CSF and mutant #10 treatment causing a 12.8-fold increase in circulating eosinophil count compared to PBS alone. In BALB/c mice mutant #10 alone caused a 2.9-fold increase in circulating eosinophil count compared to PBS alone. G-CSF and PBS caused no increase, with CSF and mutant #10 treatment causing a similiar increase in count as mutant #10.

Figure 18:
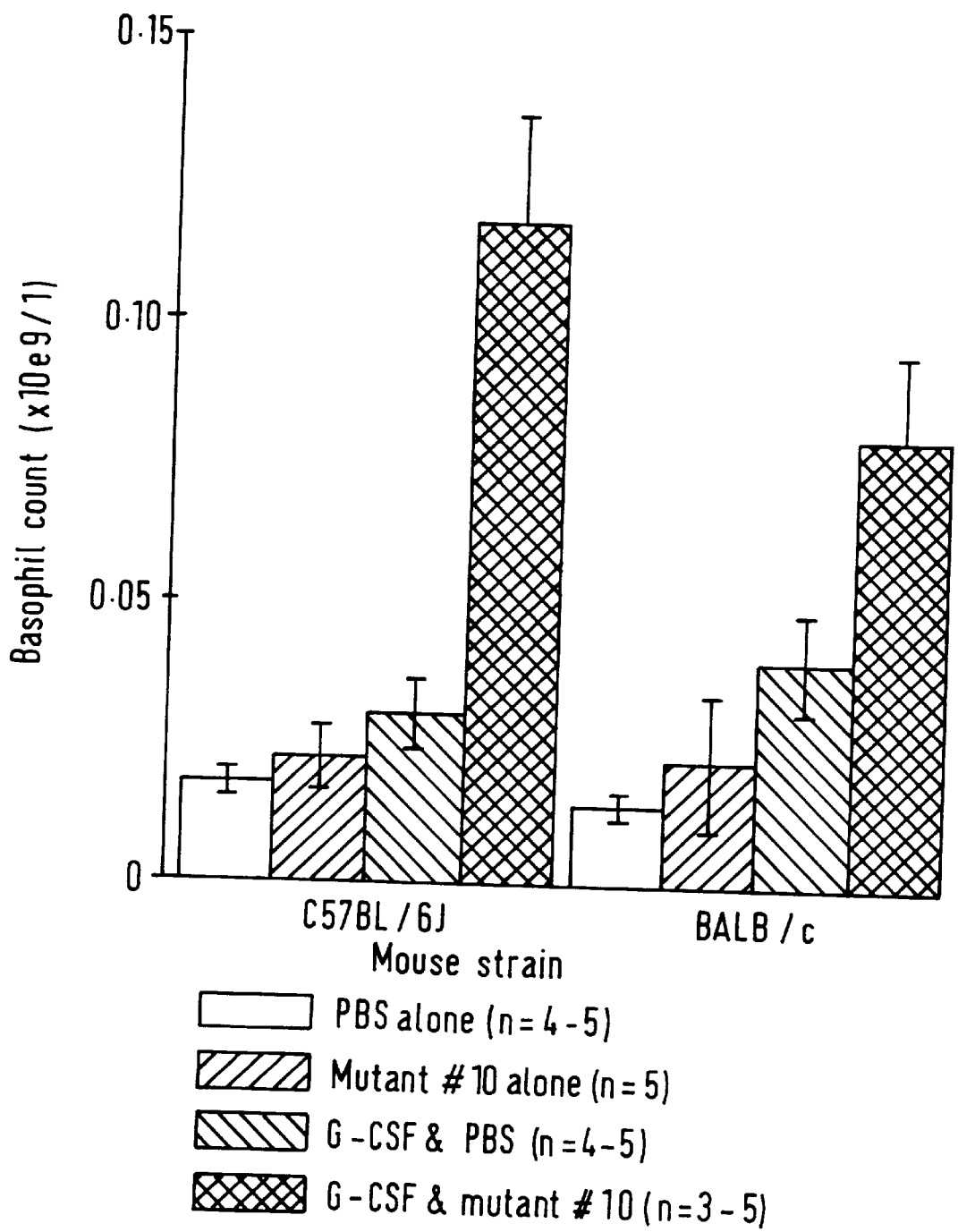
FIG. 18 shows the effects of G-CSF co-administered with mutant #10 (LD78) (Asp26>Ala)) SEQ ID NO.2 on mouse basophil count.

(e) Basophil count: The effects on basophil count are shown in FIG. 18.

In C57BL/6J mice, neither mutant #10 alone or G-CSF and PBS treatment caused any increase in circulating basophil count. However, G-CSF and mutant #10 caused a 6.7-fold increase in circulating basophil count compared to PBS alone. In BALB/c mice mutant #10 alone caused no increase in basophil count, G-CSF and PBS caused a 2.9-fold increase and G-CSF and mutant #10 caused a 5.7-fold increase compared to PBS alone.

EXAMPLE 12

Figure 19:
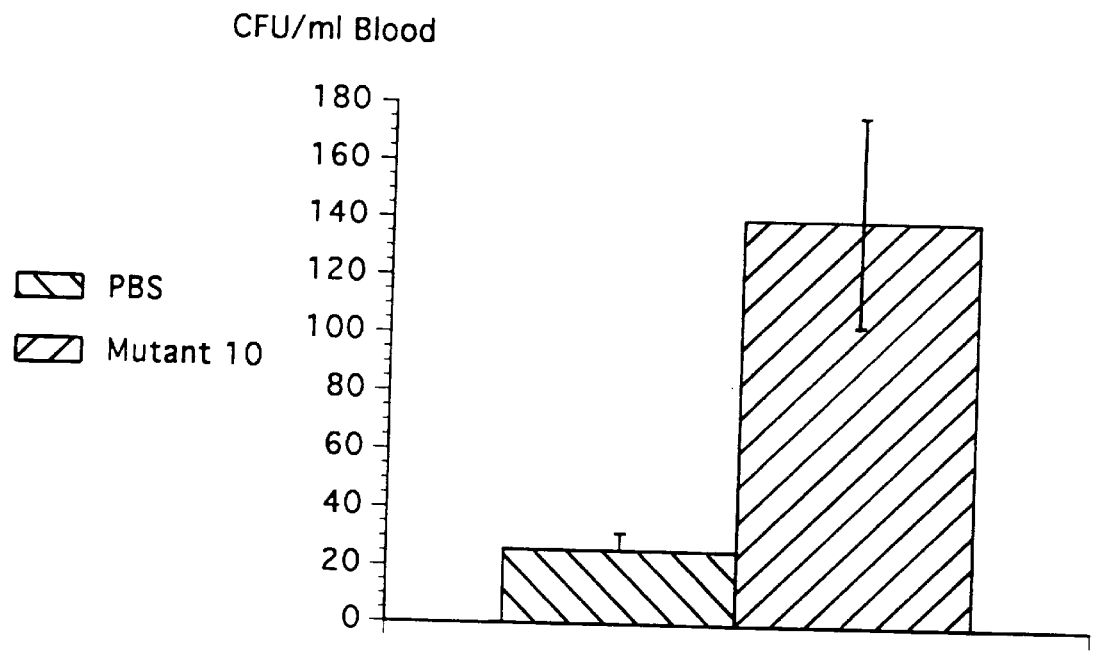
FIG. 19 shows the mobilisation of multipotent haematopoietic progenitors (CFU-mix) to perpheral blood by mutant 10.

Mobilisation of Multipotent Haematopoietic Progenitors (CFU-Mix) by Mutant #10 previous examples have demonstrated the ability of LD78 and Mutant #10 to mobilise mature haematopoietic cells and the early CFU-S to peripheral blood. These experiments were performed to investigate the effects of Stem Cell Inhibitors (SCIs) on the more mature multipotent progenitors able to form colonies in semi-solid media. Groups of C57BL/6J mice (n=5/group) were dosed with PBS 40 µl s.c. or mutant #10 100 µg/kg s.c. in PBS (injection volume 40 µl) via the flank between the scapulae. Blood samples were taken 30 minutes later by cardiac puncture from mice under terminal halothane anaesthesia. Blood samples were immediately pooled and anticoagulated with heparin. At the same time the spleens were removed, disrupted in Iscoves media and pooled. Low density mononuclear cells from both blood and spleens were prepared over ficoll gradients. The number of haematopoietic progenitors in each sample was estimated by plating the low density mononuclear cells in methylcellulose containing appropriate nutrients and growth factors (commercially available from Stem Cell Technologies, Vancouver, Canada). The plates were incubated at 37° C. in 5% $O_2$, 5% $CO_2$ for 7 days and the colonies were scored using a low magnification microscope. The number of progenitors mobilised into the peripheral blood is presented in colony forming units (CFU) per ml (FIG. 19). The number of CFU mobilised to the spleen is presented as CFU/spleen (FIG. 20). In C57BL/6J mice Mutant #10 mobilised progenitors causing a 5.4 fold increase in peripheral blood progenitors and a 7.7 fold increase in spleen progenitors which were able to form colonies in methylcellulose media (CFU-mix).

The progenitors detected by this assay are more mature and distinct from those described as CFU-S in Example 10. Clincally, these types of progenitors may reduce the need for blood transfusions after transplantation.

EXAMPLE 13

Figure 21:
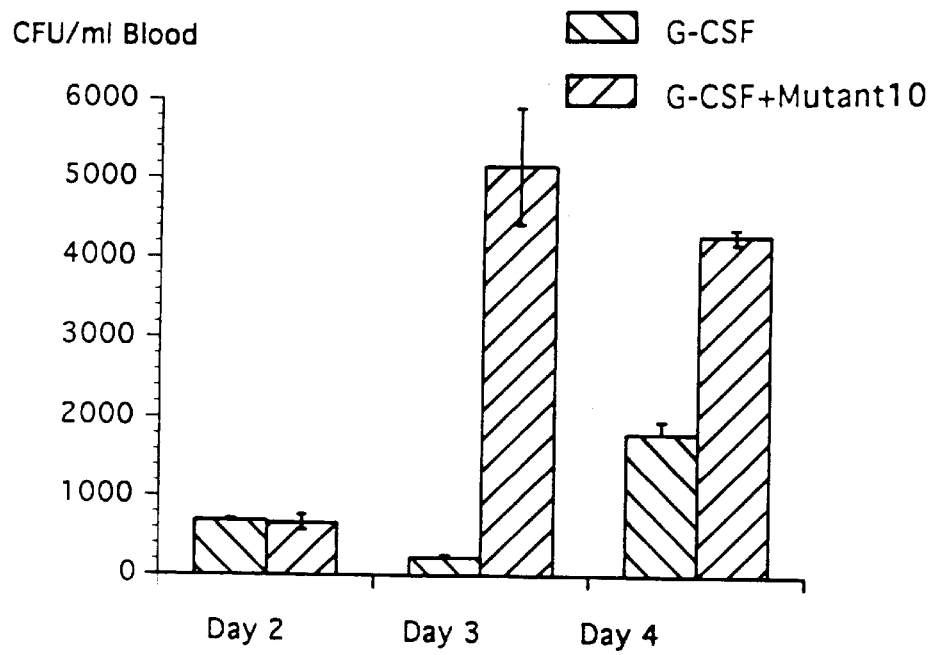
FIG. 21 shows the effect of sequential use of G-CSF and SCI's on multipotent haematopoietic progenitor mobilisation to peripheral blood.
Figure 22:
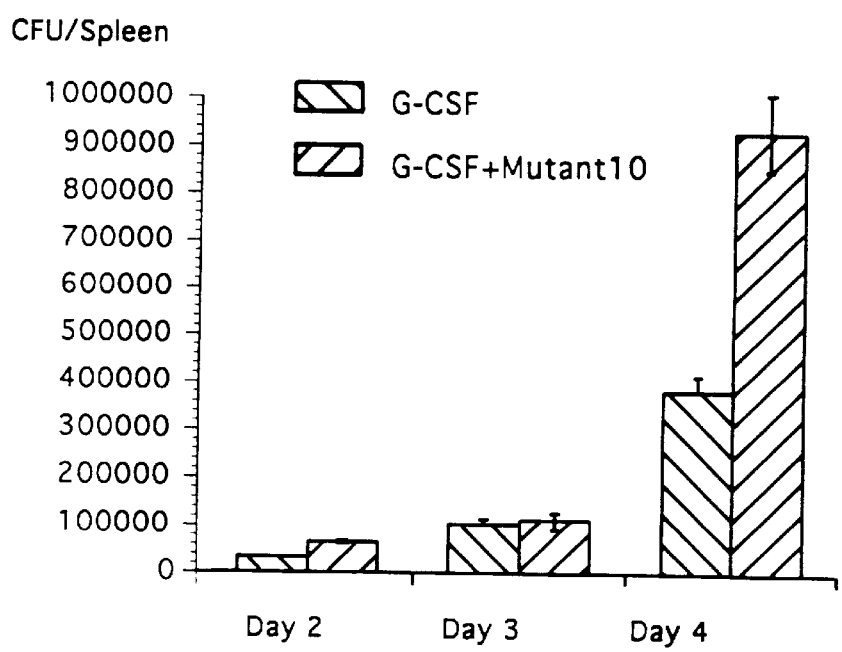
FIG. 22 shows the effect of sequential use of G-CSF; and SCI's on multipotent haematopoietic progenitor mobilisation to the spleen.

Effect of Sequential Use of G-CSF and SCIs on Multi-Potent Haematopoietic Progenitors Several colony stimulating factors such as EPO, G-CSF and GM-CSF are currently used in the clinic to improve the rate of haematological recovery after damage. To begin a study into the interaction of SCIs with other cytokines we investigated the ability of SCIs to augment the effects of G-CSF after 2, 3 or 4 days of C-CSF treatment. Groups of C57BL/6J mice (n=5/group) were dosed with G-CSF 100 µg/kg s.c. diluted appropriately in PBS (injection volume 40 µl) b.i.d. at 0 and 7 hours on days 0 and 1; 0, 1 and 2, or 0, 1, 2 and 3 as appropriate. On the day after the last G-CSF treatment (days +2, 3 and 4) groups received PBS 40 µl s.c. or Mutant #10, 100 µg/kg s.c. Blood and spleens were removed 30 minutes later and the spleens were disrupted. Low density mononuclear cells from blood and spleens were purified over ficoll gradients. The multipotent haematopoietic progenitors were enumerated using methylcellulose assays as described in Example 12. The effect of Mutant #10 on G-CSF primed mobilisation of multi-potent progenitors to peripheral blood is shown in FIG. 21 and to the spleen in FIG. 22. Mutant #10 improves the yield of peripheral blood progenitors after 2 or 3 days of G-CSF priming with 22 fold and 2.4 fold increases over the C-CSF treatment alone. Mutant #10 also enhances 2.4 fold the mobilisation of progenitors to the spleen on day +4 (after 3 days G-CSF priming).

These results are very signifcant and suggest that a two-fold improvement over the currently use G-CSF treatments may be achievable. That tranlates to a reduction in the number of treatments in hospitals to collect progenitors and/or a greater success rate of transplantation. Synergy with other colony stimulating factors, such as GM-CSF, IL3, SCF, may be expected.

EXAMPLE 14

Figure 23:
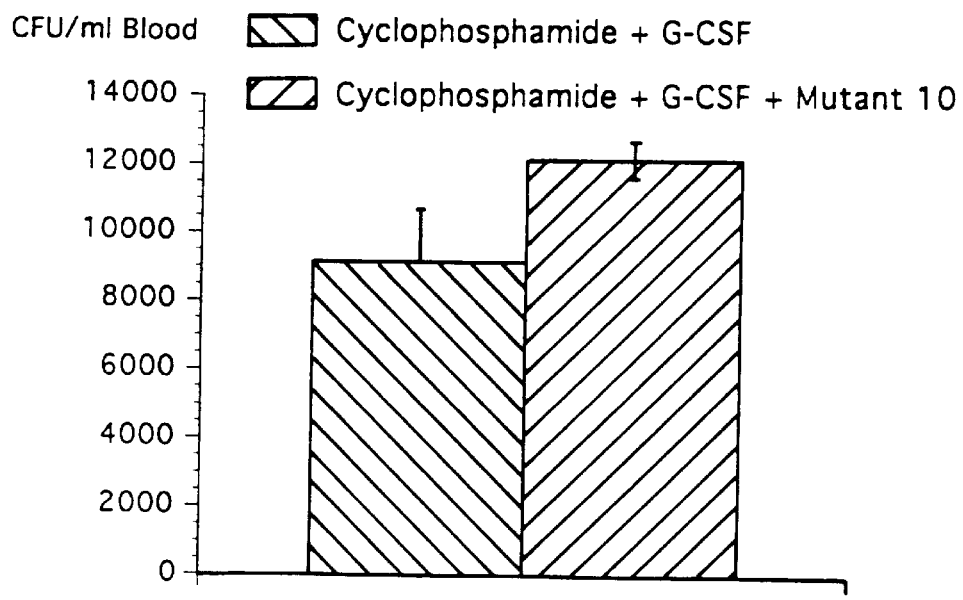
FIG. 23 shows the effect of mutant 10 on the mobilisation of progenitors from cyclophosphamide and G-CSF primed mice to the perpheral blood.
Figure 24:
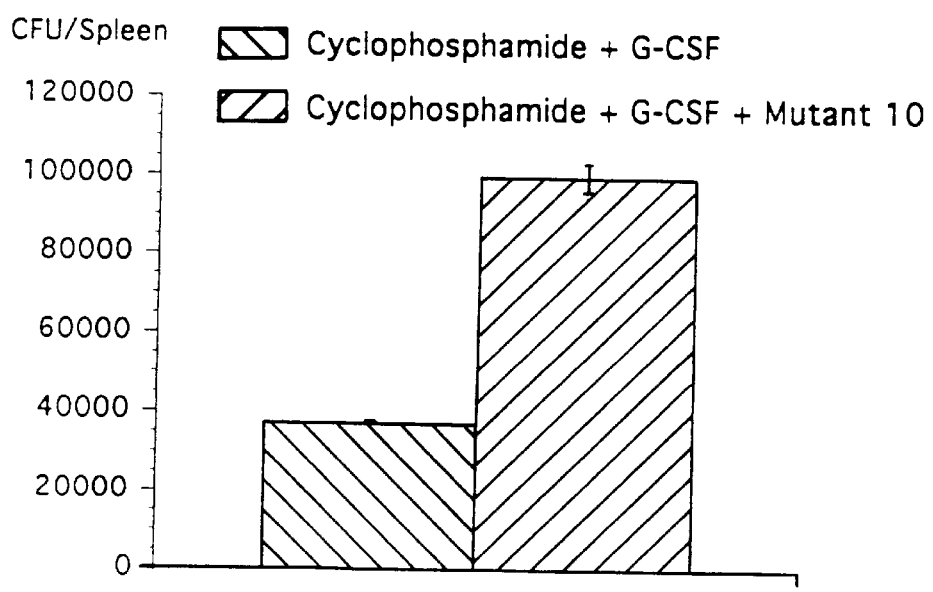
FIG. 24 shows the effect of mutant to on the mobilisation of progenitors from cyclophosphamide and G-CSF primed mice to the spleen.

The Effect of Mutant #10 on the Mobilisation of Progenitors from Cyclophosphamide and G-CSF- Primed Mice Clinically a sub-ablative chemotherapy dose is often used to prepare donor marrow prior to cytokine mobilisation as it make the marrow more responsive to colony stimulating factors. In a murine model of such a progenitor mobilisation protocol C57BL/6J mice were dosed with cyctophosphamide 200 mg/1 kg i.p. day 0 and G-CSF 100 µl/kg b.i.d s.c. for 3 days. On day 4 the mice received Mutant #10 100 µg/kg s.c. or PBS (injection volume 40 µg) and 30 minutes later blood and spleens were sampled. The low density mononuclear cells from both tissues were prepared by ficoll gradients and plated in methylcellulose as described in Example 12. There was a modest increase in the number of peripheral blood progenitors after Mutant #10 treamtent compared to control (FIG. 23). There was substantial (2.7 fold) improvement in progenitors mobilised to the spleen after cyclophosphamide and G-CSF treatment (FIG. 24).

In conclusion, this example shows that Mutant #10 improves mobilisation in a clinically relevant setting using cyctophosphamide and G-CSF priming.

EXAMPLE 15

The Effect of Sequential Use of G-CSF and Mutant #10 on the Mobilisation of Colony Forming Unit Spleen (CFU-S)

Example 13 showed that significantly more multi-potent progenitors were mobilised by the sequential use of G-CSF and Mutant #10 compared to the use of either alone. This example extends this observation to demonstrate that the sequential cytokine regime also enhanced the mobilisation of CFU-S to peripheral blood compared to the use of either agent alone. Groups of BALB/c mice were injected with PBS or G-CSF 100 μg/kg s.c. at 0 and 7 hours on day 0 and +1. On day 2 groups received Mutant #10 100 μg/kg s.c. or PBS and 30 minutes later peripheral blood was harvested. The dosing strategy produced four treatment groups. PBS controls, Mutant #10 alone, G-CSF priming followed by PBS and G-CSF priming+Mutant #10. The number of CFU-S/ml of peripheral blood was estimated using the CFU-S assay as described in example 10. Groups of donor mice were sacrificed on day 8 and 12 after transplantation to yield CFU-$S_{D8}$ (FIG. 25) and CFU-$S_{D12}$ (FIG. 26) results respectively. Mutant #10 induced a 4.2 fold increase in CFU-$S_{D8}$ and a 1.7 fold increase in CFU-$S_{D12}$ compared to PBS control. The 2 days of (G-CSF priming caused a 67 fold and 19.6 fold increase in CFU-$S_{D8}$ and CFU-$S_{D12}$ respectively. The 30 minute treatment with Mutant #10 enhanced G-CSF mobilisation from 67 to 93 fold and from 19.6 to 98.5 fold of CFU-$S_{D8}$ and CFU-$S_{D12}$ respectively.

These results expand those of Example 10 to include the combined use of Mutant #10 and G-CSF. These early progenitors are the type which are important for successful transplantation.

EXAMPLE 16

Examination of the Repopulating Ability of the Peripheral Blood Mobilised CFU-S The CFU-S assay as described in Example 10 measures the number of early progenitors present in a sample but it does not provide an estimate of the ability of the progenitors to provide long-term engagement if they were used in a transplantation experiment. An additional step to the assay provides such an estimate and is called Multiple Repopulation Assay or MRA.

Peripheral blood obtained from each of the four groups of Example 15, control, Mutant #10, G-CSF and G-CSF+ Mutant #10 were injected into lethally irradiated recipients as described in Example 15. Ten days later the were sacrificed and the femurs were harvested. Suspensions of marrow cells were prepared and fractions of the suspensions were injected into a irradiated recipients. Twelve days later the CFU-$S_{D12}$ were count as described in Example 15. The MRA assay measures the ability of donor stem cels which repopulate the primary recipient to form CFU-$S_{D12}$ colonies in the secondary recipient. The results are presented as CFU-Sd12/femur/ml blood (FIG. 27). Compared to control groups, Mutant #10 alone causes a 1.6 fold increase, G-CSF causes a 36.8 fold increase and G-CSF plus Mutant #10 causes a 99.3 fold increase in the mobilisation of the very early progenitors assessed in the MRA assay.

In summary, this assay gives an idea of how good at transplantation the cells would be. Mutant #10 improves G-CSF treatment considerably.

EXAMPLE 17

Mobilisation of Multi-Potent Progenitors by Variants of LD78

The ability of 7 variants of LD78 to enhance the mobilisation of progenitors after 2 days of G-CSF priming was investigated. Alternative wild-type LD78 variants such as mutant #35 and essentially inactive variants such as mutant #26 were included. Groups of C57BL/6J mice (3 mice per group) were dosed with G-CSF 100 μg/kg b.i.d. at 0 and 7 hours on days 0 and 1. On day 2 each group was dosed with a variant of LD78 at 100 μg/kg s.c. or PBS (in an injection volume of 40 μl). Peripheral blood and spleens were harvested 30 minutes later and the number of colony forming units estimated using the methylcellulose assay described in Example 12.

Several of the variants mobilised better than control PBS (FIG. 28). The alternative wild-type variant 35 and mutants 10 and 83 performed equally well. Mutant #2 was also able to mobilise CFU-mix to the spleen.

EXAMPLE 18

Effect of Sequential Use of G-CSF and SCIs on the Mobilisation of Very Early Multipotent Progenitors Expressing Sca1⁺but not Lin⁺cell surface Markers The earliest haematopoietic stem cells are not highly proliferative and they respond poorly to CFU-S or CFU-mix types of assays. They are most accurately enumerated using fluorescence activated cell scoring (FACS). These early stem cells display a specific antigen: stem cell antigen (Sca 1). Due to their immaturity they do not display any differentiation associated antigens and are described as Lineage negative (Lin−). The mobilisation of these early progenitors to the peripheral blood during sequential G-CSF and Mutant #10 administration has been investigated. C57BL/6J mice received 100 μg/kg G-CSF b.i.d. s.c. or a PBS control for 2 days followed by 100 μg/kg Mutant #10 or a PBS control on the third day. Peripheral blood was harvested 30 minutes later by cardiac puncture. Blood from 3 animals per group was pooled and labelled with a panel of lineage specific antibodies couples to fluorescein (CD4, CD8, B220, Gr−1 and Mac-1) and a phycoerythrin conjugated antibody to Sca−1. Samples were then fixed, lysed and resuspended in PBS ready for flow cytometric analysis on a Becton Dickenson FACSan. Electronic gates were set to accept low density cells that expressed Sca−1 antigen (Sca+) but no lineage markers (Lin−). The number of cells displaying the phenotype Lin−, Sca+ was determined for each pooled group and the data plotted. The results (FIG. 29) show an increase in peripheral blood progenitors cells following treatment with G-CSF or Mutant #10 alone and a synergistic effect when the two are used in combination.

The cells used in this example represent a very early murine progenitor population which are capable of long term marrow population following transplantation.

EXAMPLE 19

The Effect of Mutant #10 on the Mobilisation of Very Early Progenitors from Cyclophosphamide and G-CSF Primed Mice To expand the experiment of Example 14, portions of peripheral blood from this experiment were analysed by FACS using the methods of example 1 to enumerate the mobilisation of Sca1+Lin− progenitors. The results (FIG. 30) are for a pool of animals per group and demonstrate at mutant #10 combination with G-CSF has a significant effect, a 4.7 fold increase, on stem cell mobilisation over G-CSF treatment alone. This study extends the previous types results on mature and multipotent progenitors to demonstrate mobilisation of the most primitive progenitors.

In this Example, G-CSF is administrated in a clinical environment following treatment with a cytotoxic drug such as cyctophosphamide in order to mobilise progenitor cells for transplantation. This murine model of mobilisation suggests Mutant #10 greatly enhances the effects of G-CSF.

EXAMPLE 20

Mobilisation of Mature Leukocytes by Variants of LD78

Male C57BL/6J mice (n=5/group) were predosed for 2 days with G-CSF (Amgen, NEUPOGEN™) 100 μg/kg s.c.

B.I.D. (0 and 7 hr). 14 hours following the last G-CSF dose, mice received LD78 variants, 100 μg/kg s.c., or PBS 100 μl s.c. For sampling, mice were terminally anaesthetised with halothane and blood was withdawn by cardiac puncture. Blood samples (0.5 ml) were immediately anticoaglated with EDTA in coated sample cups (Teklab UK). Differential white blood cell counts were performed on a TECHNICON H*1™ with FDA approved software.

FIGS. 31, 32, 33, 34 and 35 Show the effects of various variants of LD78 on the neutrophil, lymphocyte, monocyte, eosinophil and basophil count following 2 days pre-dosing with G-CSF, 100 μg/kg s.c. B.I.D.

(Mutant #2=Lys 44>Glu, Arg 45>Gln

Mutant #26=Phe 28>Glu, Arg 47>Glu

Mutant #35=Leu-Ser-Ala-Ser 1>Pro, Gly 38>Ser and Ser 46>Gly

Mutant #47=Glu 56>Ser

Mutant #52=Glu 66>Ser

Mutant #83=Phe23>Ala)

The data show an order of potency with Mutant #10 being equipotent with mutant #35, mutant #47, mutant #52 and mutant #83 and more potent than mutant #2 with mutant #26 being inactive at producing any mobilisation of mature white blood cells in this assay system.

EXAMPLE 21

Mobilisation of Mature Leukocytes by Sequential Administration of G-CSF and Mutant #10

Male C57BL/6J mice (n=5/group) were pre-dosed with either; G-CSF (Amgen, NEUPOGEN™) 100 μg/kg s.c. B.I.D. (0 and 7 hr) or PBS 100 μl s.c. B.I.D. (0 and 7 hr), for 2, 3 or 4 days. 24 hour following the last G-CSF dose, mice received Mutant #10, 100 μg/kg s.c., or PBS 100 l s.c. Blood samples were taken 30 later. For sampling mice were terminally anaesthetised with halothane and blood was withdrawn by cardiac puncture. Blood samples (0.5 ml) were immediately anticoagulated wih EDTA in coated sample cups (Teklab). Differential white blood cell counts were performed on a TECHNICON H*1™ with FDA approved software.

FIGS. 36, 37, 38, 39 and 40 Show the effects of mutant #10 on the neutrophil, lymphocyte, monocyte, eosinophil and basophil count following 2, 3 and 4 days From FIGS. 36, 37 and 40 (neutrophil, lymphocyte and basophil counts), it can be seen that Mutant #10 alone produces an increase only in neutrophil counts. However, Mutant #10 following 2, 3 or 4 days of C-CSF produces a synergistic release of all these mature cells. G-CSF alone produces increases in circulating counts increasing as the number of days of treatment increases. The data in FIGS. 38 and 39 show, for monocyte and eosinophil counts, that G-CSF alone has no effect on the number of circulating cells; mutant #10 alone causes a release of these cells and the release is not altered by G-CSF pre-treatment.

EXAMPLE 22

The Effect of rhMIP-1β on Neutrophil Count in the BALB/c Mouse (A Comparative Example)

Male BALB/c mice were dosed with rhMIP-1β, 100 μg/kg s.c., control mice received PBS/BAA vehicle control. 30 minutes later blood samples were taken from mice terminally anaesthetised with halothane. Blood samples were immediately anticoagulated with EDTA in coated sample cups (Teklab UK). Neutophil counts were performed on a TECNNICON H*1™ with FDA approved software.

FIG. 41 shows the effect of rhMIP-10β on neutrophil count in the BALB/c mouse. rhMIP-1β, 100 μg/kg s.c., has no effect on circulating neutrophil counts 30 minutes post dosing.

It should be noted that, in the hands of the inventors, MIP-1β is not a stem cell inhibitor. Therefore, this example demonstrates that a molecule which is not a stem cell inhibitor fails to promote neutrophil release. To put it another way, neutrophil appearance may be used as a basis for distinguishing between MIP-1α, which is a stem cell inhibitor, and MIP-1β, which is not.

---

We claim:

1. A method of harvesting hematopoietic cells from an animal, comprising:
   (1) prior to, or in the absence of, chemotherapy or radiotherapy, administering to said animal an effective amount of a stem cell inhibitor to cause the rapid release and mobilization of haematopoietic cells from the marrow, wherein said stem cell inhibitor is wildtype LD78 or a variant thereof having stem cell inhibitory activity, and,
   (2) harvesting the haematopoietic cells from the animal prior to autologous or heterologus transportation.

2. The method of claim 1, wherein said stem cell inhibitor is an LD78 variant containing an amino acid substitution at one or more of the aspartic acid or glutamic acid side-chains.

3. A method of harvesting hematopoietic cells from an animal, comprising:
   (1) prior to, or in the absence of, chemotherapy or radiotherapy, administering to said animal an effective amount of a stem cell inhibitor, wherein said stem cell inhibitor is an LD78 variant having stem cell inhibitory activity and with a sequence corresponding to wildtype LD78 with a mutation at an amino acid residue(s) selected from the group consisting of LD78 (Asp26>Ala), LD78(Glu56>Ser), LD78(Phe12>Gln), LD78(Arg17>Ser), LD78(Glu66>Ser), LD78 (Asp26>Ser), LD78(Phe23>Ala) and LD78 (Lys44>Glu and ARG45>Glu), according to SEQ ID NO.2, wherein said effective amount of said stem cell inhibitor induces the release and mobilization of hematopoietic cells, and,
   (2) harvesting the haematopoietic cells from the animal prior to autologous or heterologous transplantion.

4. The method of any of claims 1 or 3 wherein said haematopoietic cells are white blood cells.

5. The method of any of claims 1 or 3 claim wherein said haematopoietic cells are neutrophils.

6. The method of any of claims 1 or 3 wherein said hematopoietic cells are haematopoietic progenitor cells.

7. The method of any of claims 1 or 3 wherein said hematopoietic cells are haematopoietic stem cells.

8. The method of any of claims 1 or 3 further comprising the administration of a colony-stimulating factor.

9. The method of claim 8, wherein said colony stimulating factor is G-CSF or GM-CSF.

10. The method of claim 8, wherein said administration of said stem cell inhibitor and said colony-stimulating factor is done by, stimulating or sequential administration.

\* \* \* \* \*